(12) United States Patent
Rousso et al.

(10) Patent No.: US 7,872,235 B2
(45) Date of Patent: Jan. 18, 2011

(54) MULTI-DIMENSIONAL IMAGE RECONSTRUCTION AND ANALYSIS FOR EXPERT-SYSTEM DIAGNOSIS

(75) Inventors: Benny Rousso, Rishon-LeZion (IL); Dalia Dickman, Moshav Manof Doar-Na Misgav (IL); Michael Nagler, Tel-Aviv (IL); Shankar Vallabhajosula, Larchmont, NY (US)

(73) Assignee: Spectrum Dynamics LLC, Orangeburg, NY (US)

( * ) Notice: Subject to any disclaimer, the term of this patent is extended or adjusted under 35 U.S.C. 154(b) by 351 days.

(21) Appl. No.: 11/794,799

(22) PCT Filed: Jan. 15, 2006

(86) PCT No.: PCT/IL2006/000059

§ 371 (c)(1),
(2), (4) Date: Jul. 5, 2007

(87) PCT Pub. No.: WO2006/075333

PCT Pub. Date: Jul. 20, 2006

(65) Prior Publication Data

US 2008/0033291 A1 Feb. 7, 2008

Related U.S. Application Data

(63) Continuation-in-part of application No. PCT/IL2005/001215, filed on Nov. 16, 2005, which is a continuation-in-part of application No. PCT/IL2005/001173, filed on Nov. 9, 2005, which is a continuation-in-part of application No. PCT/IL2005/000575, filed on Jun. 1, 2005, which is a continuation-in-part of application No. PCT/IL2005/000572, filed on Jun. 1, 2005, which is a continuation-in-part of application No. PCT/IL2005/000048, filed on Jan. 13, 2005, and a continuation of application No. 11/034,007, filed on Jan. 13, 2005, now Pat. No. 7,176,466.

(60) Provisional application No. 60/691,780, filed on Jun. 20, 2005, provisional application No. 60/700,299, filed on Jul. 19, 2005, provisional application No. 60/700,318, filed on Jul. 19, 2005, provisional application No. 60/700,752, filed on Jul. 20, 2005, provisional application No. 60/700,317, filed on Jul. 19, 2005, provisional application No. 60/700,753, filed on Jul. 20, 2005, provisional application No. 60/702,979, filed on Jul. 28, 2005, provisional application No. 60/720,034, filed on Sep. 26, 2005, provisional application No. 60/720,541, filed on Sep. 27, 2005, provisional application No. 60/720,652, filed on Sep. 27, 2005, provisional application No. 60/741,440, filed on Dec. 2, 2005, provisional application No. 60/750,287, filed on Dec. 13, 2005, provisional application No. 60/750,334, filed on Dec. 15, 2005, provisional application No. 60/750,597, filed on Dec. 15, 2005.

(30) Foreign Application Priority Data

Oct. 10, 2005 (IL) ..................................... 171346
Nov. 27, 2005 (IL) ..................................... 172349

(51) Int. Cl.
*G01T 1/161* (2006.01)
(52) U.S. Cl. ................................................ 250/363.04
(58) Field of Classification Search ............. 250/363.04
See application file for complete search history.

(56) References Cited

U.S. PATENT DOCUMENTS

| | | |
|---|---|---|
| 2,776,377 A | 1/1957 | Anger |
| 3,340,866 A | 9/1967 | Noller |
| 3,684,887 A | 8/1972 | Hugonin |
| 3,690,309 A | 9/1972 | Pluzhnikov et al. |
| 3,719,183 A | 3/1973 | Schwartz |
| 3,739,279 A | 6/1973 | Hollis |

| | | | | | | |
|---|---|---|---|---|---|---|
| 3,971,362 | A | 7/1976 | Pope et al. | 5,880,475 A | 3/1999 | Oka et al. |
| 4,015,592 | A | 4/1977 | Bradley-Moore | 5,891,030 A | 4/1999 | Johnson et al. |
| 4,278,077 | A | 7/1981 | Mizumoto | 5,900,533 A | 5/1999 | Chou |
| 4,364,377 | A | 12/1982 | Smith | 5,916,167 A | 6/1999 | Kramer et al. |
| 4,521,688 | A | 6/1985 | Yin | 5,928,150 A | 7/1999 | Call |
| H000012 | H | 1/1986 | Bennett et al. | 5,932,879 A | 8/1999 | Raylman et al. |
| 4,595,014 | A | 6/1986 | Barrett et al. | 5,939,724 A | 8/1999 | Eisen et al. |
| 4,674,107 | A | 6/1987 | Urban et al. | 5,961,457 A | 10/1999 | Raylman et al. |
| 4,689,041 | A | 8/1987 | Corday et al. | 5,984,860 A | 11/1999 | Shan |
| 4,689,621 | A | 8/1987 | Kleinberg | 5,987,350 A | 11/1999 | Thurston |
| 4,731,536 | A | 3/1988 | Rische et al. | 5,993,378 A | 11/1999 | Lemelson |
| 4,773,430 | A | 9/1988 | Porath | 6,002,480 A | 12/1999 | Izatt et al. |
| 4,828,841 | A | 5/1989 | Porter et al. | 6,076,009 A | 6/2000 | Raylman et al. |
| 4,844,067 | A | 7/1989 | Ikada et al. | 6,082,366 A | 7/2000 | Andra et al. |
| 4,844,076 | A | 7/1989 | Lesho et al. | 6,107,102 A | 8/2000 | Ferrari |
| 4,893,013 | A | 1/1990 | Denen et al. | 6,115,635 A | 9/2000 | Bourgeois |
| 4,928,250 | A | 5/1990 | Greenberg et al. | 6,129,670 A | 10/2000 | Burdette et al. |
| 4,929,832 | A | 5/1990 | Ledley | 6,132,372 A | 10/2000 | Essen-Moller |
| 4,951,653 | A | 8/1990 | Fry et al. | 6,135,955 A | 10/2000 | Madden et al. |
| 4,959,547 | A | 9/1990 | Carroll et al. | 6,147,353 A | 11/2000 | Gagnon et al. |
| 4,995,396 | A | 2/1991 | Inaba et al. | 6,173,201 B1 | 1/2001 | Front |
| 5,014,708 | A | 5/1991 | Hayashi et al. | 6,205,347 B1 | 3/2001 | Morgan et al. |
| 5,032,729 | A | 7/1991 | Charpak | 6,212,423 B1 | 4/2001 | Krakovitz |
| 5,033,998 | A | 7/1991 | Corday et al. | 6,236,880 B1 | 5/2001 | Raylman et al. |
| 5,070,878 | A | 12/1991 | Denen | 6,239,438 B1 | 5/2001 | Schubert |
| 5,088,492 | A | 2/1992 | Takayama et al. | 6,240,312 B1 | 5/2001 | Alfano et al. |
| 5,119,818 | A | 6/1992 | Carroll et al. | 6,242,743 B1 | 6/2001 | DeVito et al. |
| 5,151,598 | A | 9/1992 | Denen | 6,246,901 B1 | 6/2001 | Benaron |
| 5,170,055 | A | 12/1992 | Carroll et al. | 6,261,562 B1 | 7/2001 | Xu et al. |
| 5,170,789 | A | 12/1992 | Narayan et al. | 6,263,229 B1 | 7/2001 | Atalar et al. |
| 5,243,988 | A | 9/1993 | Sieben et al. | 6,271,524 B1 | 8/2001 | Wainer et al. |
| 5,246,005 | A | 9/1993 | Carroll et al. | 6,271,525 B1 | 8/2001 | Majewski et al. |
| 5,249,124 | A | 9/1993 | DeVito | 6,280,704 B1 | 8/2001 | Schutt et al. |
| 5,279,607 | A | 1/1994 | Schentag et al. | 6,324,418 B1 | 11/2001 | Crowley et al. |
| 5,299,253 | A | 3/1994 | Wessels | 6,339,652 B1 | 1/2002 | Hawkins et al. |
| 5,307,808 | A | 5/1994 | Dumoulin et al. | 6,346,706 B1 | 2/2002 | Rogers et al. |
| 5,349,190 | A | 9/1994 | Hines et al. | 6,368,331 B1 | 4/2002 | Front et al. |
| 5,383,456 | A | 1/1995 | Arnold et al. | 6,407,391 B1 | 6/2002 | Mastrippolito et al. |
| 5,386,446 | A | 1/1995 | Fujimoto et al. | 6,415,046 B1 | 7/2002 | Kerut, Sr. |
| 5,395,366 | A | 3/1995 | D'Andrea et al. | 6,420,711 B2 | 7/2002 | Tuemer |
| 5,399,868 | A | 3/1995 | Jones et al. | 6,426,917 B1 | 7/2002 | Tabanou et al. |
| 5,415,181 | A | 5/1995 | Hofgrefe et al. | 6,429,431 B1 | 8/2002 | Wilk |
| 5,441,050 | A | 8/1995 | Thurston et al. | 6,431,175 B1 | 8/2002 | Penner et al. |
| 5,448,073 | A | 9/1995 | Jeanguillaume | 6,438,401 B1 | 8/2002 | Cheng et al. |
| 5,475,219 | A | 12/1995 | Olson | 6,453,199 B1 | 9/2002 | Kobozev |
| 5,484,384 | A | 1/1996 | Fearnot | 6,459,925 B1 | 10/2002 | Nields et al. |
| 5,489,782 | A | 2/1996 | Wernikoff | 6,480,732 B1 | 11/2002 | Tanaka et al. |
| 5,493,595 | A | 2/1996 | Schoolman | 6,484,051 B1 | 11/2002 | Daniel |
| 5,519,221 | A | 5/1996 | Weinberg | 6,490,476 B1 | 12/2002 | Townsend et al. |
| 5,572,999 | A | 11/1996 | Funda et al. | 6,516,213 B1 | 2/2003 | Nevo |
| 5,579,766 | A | 12/1996 | Gray | 6,525,320 B1 | 2/2003 | Juni |
| 5,604,531 | A | 2/1997 | Iddan et al. | 6,525,321 B2 | 2/2003 | Juni |
| 5,617,858 | A | 4/1997 | Taverna et al. | 6,549,646 B1 | 4/2003 | Yeh et al. |
| 5,635,717 | A | 6/1997 | Popescu | 6,560,354 B1 | 5/2003 | Maurer et al. |
| 5,657,759 | A | 8/1997 | Essen-Moller | 6,567,687 B2 | 5/2003 | Front et al. |
| 5,672,877 | A | 9/1997 | Liebig et al. | 6,584,348 B2 | 6/2003 | Glukhovsky |
| 5,682,888 | A | 11/1997 | Olson et al. | 6,587,710 B1 | 7/2003 | Wainer |
| 5,690,691 | A | 11/1997 | Chen et al. | 6,592,520 B1 | 7/2003 | Peszynski et al. |
| 5,694,933 | A | 12/1997 | Madden et al. | 6,602,488 B1 | 8/2003 | Daghighian |
| 5,695,500 | A | 12/1997 | Taylor et al. | 6,607,301 B1 | 8/2003 | Glukhovsky et al. |
| 5,716,595 | A | 2/1998 | Goldenberg | 6,611,141 B1 | 8/2003 | Schulz et al. |
| 5,727,554 | A | 3/1998 | Kalend et al. | 6,614,453 B1 | 9/2003 | Suri et al. |
| 5,729,129 | A | 3/1998 | Acker | 6,628,983 B1 | 9/2003 | Gagnon |
| 5,732,704 | A | 3/1998 | Thurston et al. | 6,628,984 B2 | 9/2003 | Weinberg |
| 5,744,805 | A | 4/1998 | Raylman et al. | 6,632,216 B2 | 10/2003 | Houzego et al. |
| 5,784,432 | A | 7/1998 | Kurtz et al. | 6,633,658 B1 | 10/2003 | Dabney et al. |
| 5,811,814 | A | 9/1998 | Leone et al. | 6,638,752 B2 | 10/2003 | Contag et al. |
| 5,821,541 | A | 10/1998 | Tümer | 6,643,538 B1 | 11/2003 | Majewski et al. |
| 5,833,603 | A | 11/1998 | Kovacs et al. | 6,662,036 B2 | 12/2003 | Cosman |
| 5,842,977 | A | 12/1998 | Lesho et al. | 6,697,660 B1 | 2/2004 | Robinson |
| 5,846,513 | A | 12/1998 | Carroll et al. | 6,728,583 B2 | 4/2004 | Hallett |
| 5,857,463 | A | 1/1999 | Thurston et al. | 6,748,259 B1 | 6/2004 | Benaron et al. |
| 5,871,013 | A | 2/1999 | Wainer et al. | 6,771,802 B1 | 8/2004 | Patt et al. |

| | | | |
|---|---|---|---|
| 6,943,355 B2 | 9/2005 | Shwartz et al. |
| 6,963,770 B2 | 11/2005 | Scarantino et al. |
| 7,043,063 B1 | 5/2006 | Noble et al. |
| 7,142,634 B2 | 11/2006 | Engler et al. |
| 7,176,466 B2 | 2/2007 | Rousso et al. |
| 7,187,790 B2 | 3/2007 | Sabol et al. |
| 7,468,513 B2 | 12/2008 | Charron et al. |
| 7,490,085 B2 | 2/2009 | Walker et al. |
| 2002/0072784 A1 | 6/2002 | Sheppard, Jr. et al. |
| 2002/0085748 A1 | 7/2002 | Baumberg |
| 2002/0087101 A1 | 7/2002 | Barrick et al. |
| 2002/0099295 A1 | 7/2002 | Gil et al. |
| 2002/0103431 A1 | 8/2002 | Toker et al. |
| 2002/0148970 A1 | 10/2002 | Wong et al. |
| 2002/0168317 A1 | 11/2002 | Daighighian et al. |
| 2002/0183645 A1 | 12/2002 | Nachaliel |
| 2003/0001837 A1 | 1/2003 | Baumberg |
| 2003/0013966 A1 | 1/2003 | Barnes et al. |
| 2003/0063787 A1 | 4/2003 | Natanzon et al. |
| 2003/0081716 A1 | 5/2003 | Tumer |
| 2003/0191430 A1 | 10/2003 | D'Andrea et al. |
| 2003/0202629 A1 | 10/2003 | Dunham et al. |
| 2003/0208117 A1 | 11/2003 | Shwartz et al. |
| 2004/0003001 A1 | 1/2004 | Shimura |
| 2004/0010397 A1 | 1/2004 | Barbour et al. |
| 2004/0015075 A1 | 1/2004 | Kimchy et al. |
| 2004/0054248 A1 | 3/2004 | Kimchy et al. |
| 2004/0054278 A1 | 3/2004 | Kimchy et al. |
| 2004/0081623 A1 | 4/2004 | Eriksen et al. |
| 2004/0086437 A1 | 5/2004 | Jackson et al. |
| 2004/0101176 A1 | 5/2004 | Mendonca et al. |
| 2004/0116807 A1 | 6/2004 | Amrami et al. |
| 2004/0153128 A1 | 8/2004 | Suresh et al. |
| 2004/0171924 A1 | 9/2004 | Mire et al. |
| 2004/0204646 A1 | 10/2004 | Nagler et al. |
| 2005/0020915 A1 | 1/2005 | Bellardinelli et al. |
| 2005/0055174 A1 | 3/2005 | David et al. |
| 2005/0205792 A1 | 9/2005 | Rousso et al. |
| 2005/0215889 A1 | 9/2005 | Patterson, II |
| 2005/0253073 A1 | 11/2005 | Joram et al. |
| 2005/0266074 A1 | 12/2005 | Zilberstein et al. |
| 2006/0160157 A1 | 7/2006 | Zuckerman |
| 2006/0237652 A1 | 10/2006 | Kimchy et al. |
| 2007/0156047 A1 | 7/2007 | Nagler et al. |
| 2007/0166227 A1 | 7/2007 | Liu et al. |
| 2007/0194241 A1 | 8/2007 | Rousso et al. |
| 2008/0042067 A1 | 2/2008 | Rousso et al. |
| 2008/0128626 A1 | 6/2008 | Rousso et al. |
| 2008/0230705 A1 | 9/2008 | Rousso et al. |
| 2008/0237482 A1 | 10/2008 | Shahar et al. |
| 2008/0260637 A1 | 10/2008 | Dickman |
| 2008/0277591 A1 | 11/2008 | Shahar et al. |
| 2009/0078875 A1 | 3/2009 | Rousso et al. |
| 2009/0152471 A1 | 6/2009 | Rousso et al. |
| 2009/0190807 A1 | 7/2009 | Rousso et al. |

FOREIGN PATENT DOCUMENTS

| | | |
|---|---|---|
| EP | 0543626 | 5/1993 |
| EP | 0697193 | 2/1996 |
| EP | 0887661 | 12/1998 |
| GB | 2031142 | 4/1980 |
| JP | 06-109848 | 4/1994 |
| WO | WO 92/00402 | 9/1992 |
| WO | WO 99/03003 | 1/1999 |
| WO | WO 99/30610 | 6/1999 |
| WO | WO 99/39650 | 8/1999 |
| WO | WO 00/10034 | 2/2000 |
| WO | WO 00/31522 | 2/2000 |
| WO | WO 00/22975 | 4/2000 |
| WO | WO 00/18294 | 6/2000 |
| WO | WO 01/89384 | 11/2001 |
| WO | WO 02/58531 | 1/2002 |
| WO | WO 02/16965 | 2/2002 |
| WO | WO 2004/042546 | 5/2004 |
| WO | WO 2005/104939 | 11/2005 |
| WO | WO 2005/118659 | 12/2005 |
| WO | WO 2005/119025 | 12/2005 |
| WO | WO 2006/042077 | 4/2006 |
| WO | WO 2006/051531 | 5/2006 |
| WO | WO 2006/054281 | 5/2006 |
| WO | WO 2006/054296 | 5/2006 |
| WO | WO 2006/129301 | 12/2006 |
| WO | WO 2007/010534 | 1/2007 |
| WO | WO 2007/010537 | 1/2007 |
| WO | WO 2007/054935 | 5/2007 |
| WO | WO 2007/074467 | 7/2007 |
| WO | WO 2008/010227 | 1/2008 |

OTHER PUBLICATIONS

International Search Report Dated Jul. 11, 2008 From the International Searching Authority of the Patent Cooperation Treaty Re.: Application No. PCT/IL06/01511.
International Search Report Dated Jul. 25, 2008 From the International Searching Authority of the Patent Cooperation Treaty Re.: Application No. PCT/IL2007/001588.
Official Action Dated Sep. 4, 2008 From the US Patent and Trademark Office Re.: U.S. Appl. No. 10/533,568.
Official Action Dated Oct. 7, 2008 From the US Patent Office Re.: U.S. Appl. No. 10/616,301.
Official Action Dated Jul. 12, 2007 From the US Patent and Trademark Office Re.: U.S. Appl. No. 10/616,301.
Official Action Dated Dec. 13, 2007 From the US Patent and Trademark Office Re.: U.S. Appl. No. 10/616,301.
Official Action Dated Jul. 15, 2008 From the United States Patent and Trademark Office Re.: U.S. Appl. No. 09/641,973.
Official Action Dated Mar. 21, 2008 From the US Patent and Trademark Office Re.: U.S. Appl. No. 10/533,568.
Official Action Dated Jun. 25, 2008 From the US Patent and Trademark Office Re.: U.S. Appl. No. 10/616,301.
Official Action Dated Sep. 25, 2006 From the US Patent and Trademark Office Re.: U.S. Appl. No. 10/616,301.
Official Action Dated Sep. 30, 2008 From the US Patent and Trademark Office Re.: U.S. Appl. No. 10/616,301.
Supplementary Partial European Search Report Dated Nov. 11, 2008 From the European Patent Office Re.: Application No. 01951883.6.
Gugnin et al "Radiocapsule for Recording The Ionizing Radiation in The Gastrointestinal Tract", UDC 615.417:616.34-005.1-073.916-71 (All-Union Scientific-Research Institute of medical Instrument Design, Moscow. Translated from Meditsinskaya Tekhnika, 1:21-25, Jan.-Feb. 1972).
Stoddart et al. "New Multi-Dimensional Reconstructions for the 12-Detector, Scanned Focal Point, Single-Photon Tomograph", Physics in Medicine and Biology, XP020021960, 37(3): 579-586, Mar. 1, 1992. p. 582, § 2-p. 585, § 1.
Hoffman et al. "Intraoperative Probes and Imaging Probes", European Journal of Nuclear Medicine, 26(8): 913-935, 1999.
Pardridge et al. "Tracer Kinetic Model of Blood-Brain Barrier Transport of Plasma Protein-Bound Ligands", Journal of Clinical Investigation, 74: 745-752, 1984.
Reutter et al. "Direct Least Squares Estimation of Spatiotemporal Distributions From Dynamic SPECT Projections Using a Spatial Segmentation and Temporal B-Splines", IEEE Transactions on Medical Imaging, 19(5): 434-450, 2000.
Huesman et al. "Kinetic Parameter Estimation From SPECT Cone-Beam Projection Measurements", Physics in Medicine and Biology, 43(4): 973-982, 1998.
Reutter et al. "Kinetic Parameter Estimation From Attenuated SPECT Projection Measurements", IEEE Transactions on Nuclear Science, 45(6): 3007-3013, 1998.
Garcia et al. "Accuracy of Dynamic SPECT Acquisition for Tc-99m Teboroxime Myocardial Perfusion Imaging: Preliminary Results", American College of Cardiology, 51st Annual Scientific Session, Atlanta, Georgia, USA, 8 P., 2002.

Hassan et al. "A Radiotelemetry Pill for the Measurement of Ionising Radiation Using a Mercuric Iodide Detector", Phys. Med. Biol., 23(2): 302-308, 1978.

Zhang et al. "An Innovative High Efficiency and High Resolution Probe for Prostate Imaging", The Journal of Nuclear Medicine, 68: 18, 2000. Abstract.

Aoi et al. "Absolute Quantitation of Regional Myocardial Blood Flow of Rats Using Dynamic Pinhole SPECT", IEEE Nuclear Science Symposium and Medical Imaging Conference Record, 3: 1780-1783, 2002. Abstract, Figs.

Jeanguillaume et al. "From the Whole-Body Counting to Imaging: The Computer Aided Collimation Gamma Camera Project (CACAO)", Radiation Projection Dosimetry 89(3-4): 349-352, 2000.

Quartuccio et al. "Computer Assisted Collimation Gama Camera: A New Approach to Imaging Contaminated Tissues", Radiation Projection Dosimetry, 89(3-4): 343-348, 2000.

Piperno et al. "Breast Cancer Screening by Impedance Measurements", Frontiers Med. Biol. Engng., 2(2): 11-17, 1990.

Rajshekhar "Continuous Impedance Monitoring During CT-Guided Stereotactic Surgery: Relative Value in Cystic and Solid Lesions", British Journal of Neurosurgery, 6: 439-444, 1992.

Jessup "Tumor Markers—Prognostic and Therapeutic Implications for Colorectal Carcinoma", Surgical Oncology, 7: 139-151, 1998.

Corstens et al. "Nuclear Medicine's Role in Infection and Inflammation", The Lancet, 354: 765-770, 1999.

Mori et al. "Overexpression of Matrix Metalloproteinase-7mRNA in Human Colon Carcinomas", Cancer, 75: 1516-1519, 1995.

Erbil et al. "Use and Limitations of Serum Total and Lipid-Bound Sialic Acid Concentrations as Markers for Colorectal Cancer", Cancer, 55: 404-409, 1985.

Molinolo et al. "Enhanced Tumor Binding Using Immunohistochemical Analyses by Second Generation Anti-Tumor-Associated Glycoprotein 72 Monoclonal Antibodies versus Monoclonal Antibody B72.3 in Human Tissue", Cancer Research, 50: 1291-1298, 1990.

Day et al. "Localization of Radioiodinated Rat Fibrogen in Transplanted Rat Tumors", Journal of the National Cancer Institute, 23(4): 799-812, 1959.

Bromiley et al. "Attenuation Correction in PET Using Consistency Conditions and a Three-Dimensional Template", IEEE Transactions on Nuclear Science, 48(4): 1371-1377, 2001. p. 1376, col. 2, § 2.

Hayakawa et al. "A PET-MRI Registration Technique for PET Studies of the Rat Brain", Nuclear Medicine & Biology, 27: 121-125, 2000. p. 121, col. 1.

Lavallé et al. "Building a Hybrid Patient's Model for Augmented Reality in Surgery: A Registration Problem", Computing in Biological Medicine, 25(2): 149-164, 1995. p. 149-150.

Kojima et al. "Quantitative Planar Imaging Method for Measurement of Renal Activity by Using a Conjugate-Emission Image and Transmission Data", Medical Physics, 27(3): 608-615, 2000. p. 608.

Communication Pursuant to Article 94(3) EPC Dated Jul. 22, 2009 From the European Patent Office Re.: Application No. 06809851.6.

Notice of Allowance Dated Jul. 16, 2009 From the US Patent and Trademark Office Re.: U.S. Appl. No. 12/084,559.

Official Action Dated Jul. 7, 2009 From the US Patent and Trademark Office Re.: U.S. Appl. No. 10/533,568.

Official Action Dated Jul. 15, 2009 From the US Patent and Trademark Office Re.: U.S. Appl. No. 10/616,301.

Official Action Dated Jul. 20, 2009 From the US Patent and Trademark Office Re.: U.S. Appl. No. 11/980,617.

Ogawa et al. "Ultra High Resoultion Pinhole SPECT", IEEE Nuclear Science Symposium, 2: 1600-1604, 1998.

Pellegrini et al. "Design of Compact Pinhole SPECT System Based on Flat Panel PMT", IEEE Nuclear Science Symposium Conference Record, 3: 1828-1832, 2003.

Wu et al. "ECG-Gated Pinhole SPECT in Mice With Millimeter Spatial Resolution", IEEE Transactions on Nuclear Science, 47(3): 1218-1221, Jun. 2000.

Communication Pursuant to Article 94(3) EPC Dated Oct. 21, 2009 From the European Patent Office Re.: Application No. 02716285.8.

Notice of Allowance Dated Sep. 17, 2009 From the US Patent and Trademark Office Re.: U.S. Appl. No. 10/533,568.

Official Action Dated Sep. 2, 2009 From the US Patent and Trademark Office Re.: U.S. Appl. No. 10/343,792.

Official Action Dated Aug. 11, 2009 From the US Patent and Trademark Office Re.: U.S. Appl. No. 09/641,973.

Official Action Dated Sep. 15, 2009 From the US Patent and Trademark Office Re.: U.S. Appl. No. 10/616,307.

Official Action Dated Sep. 15, 2009 From the US Patent and Trademark Office Re.: U.S. Appl. No. 10/836,223.

Official Action Dated Sep. 16, 2009 From the US Patent and Trademark Office Re.: U.S. Appl. No. 09/727,464.

Official Action Dated Sep. 21, 2009 From the US Patent and Trademark Office Re.: U.S. Appl. No. 11/798,017.

Official Action Dated Aug. 28, 2009 From the US Patent and Trademark Office Re.: U.S. Appl. No. 10/240,239.

Official Action Dated Oct. 30, 2009 From the US Patent and Trademark Office Re.: U.S. Appl. No. 11/980,690.

Response Dated Dec. 10, 2009 to Official Action of Aug. 11, 2009 From the US Patent and Trademark Office Re.: U.S. Appl. No. 09/641,973.

Response Dated Oct. 12, 2009 to Notice of Allowance of Jul. 16, 2009 From the US Patent and Trademark Office Re.: U.S. Appl. No. 12/084,559.

Response Dated Oct. 14, 2009 to Official Action of May 14, 2009 From the US Patent and Trademark Office Re.: U.S. Appl. No. 11/656,548.

Response Dated Nov. 16, 2009 to Official Action of Jul. 15, 2009 From the US Patent and Trademark Office Re.: U.S. Appl. No. 10/616,301.

Supplementary Partial European Search Report and the European Search Opinion Dated Oct. 16, 2009 From the European Patent Office Re.: Application No. 06756259.5.

Moore et al. "Quantitative Multi-Detector Emission Computerized Tomography Using Iterative Attenuation Compensation", Journal of Nuclear Medicine, XP002549083, 23(8): 706-714, Aug. 1982. Abstract, p. 707, Section 'The Multi-Detector Scanner', First §.

Qi et al. "Resolution and noise Properties of MAP Reconstruction for Fully 3-D PET", IEEE Transactions on Medical Imaging, XP002549082, 19(5): 493-506, May 2000. p. 493, col. 2, Lines 10-21, p. 495, col.1, Last §.

Wilson et al. "Non-Stationary Noise Characteristics for SPECT Images", Proceedings of the Nuclear Science Symposium and Medical Imaging Conference, Santa Fe, CA, USA, Nov. 2-9, 1991, XP010058168, p. 1736-1740, Nov. 2, 1991. p. 1736, col. 2, Lines 4-6.

Appeal Brief Dated Jan. 19, 2010 to Notice of Appeal of Nov. 16, 2009 From the US Patent and Trademark Office Re.: U.S. Appl. No. 10/616,301.

Communication Pursuant to Article 94(3) EPC Dated Mar. 8, 2010 From the European Patent Office Re.: Application No. 06832278.3.

International Preliminary Report on Patentability Dated Apr. 16, 2009 From the International Bureau of WIPO Re.: Applicaiton No. PCT/IL2007/000918.

International Preliminary Report on Patentability Dated Jun. 21, 2007 From the International Bureau of WIPO Re.: Application No. PCT/IL2005/000575.

International Preliminary Report on Patentability Dated Jan. 22, 2009 From the International Bureau of WIPO Re.: Application No. PCT/IL2006/000834.

International Preliminary Report on Patentability Dated Jan. 22, 2009 From the International Bureau of WIPO Re.: Application No. PCT/IL2006/001511.

International Preliminary Report on Patentability Dated May 22, 2007 From the International Preliminary Examining Authority Re.: Application No. PCT/IL06/00059.

International Preliminary Report on Patentability Dated May 22, 2008 From the International Bureau of WIPO Re.: Application No. PCT/IL2006/001291.

International Preliminary Report on Patentability Dated May 24, 2007 From the International Bureau of WIPO Re.: Application No. PCT/IL2005/001173.

International Preliminary Report on Patentability Dated Apr. 26, 2007 From the International Bureau of WIPO Re.: Application No. PCT/IL2005/000394.

International Preliminary Report on Patentability Dated Jan. 31, 2008 From the International Bureau of WIPO Re.: Application No. PCT/IL2006/000840.
International Search Report Dated Oct. 15, 2008 From the International Searching Authority Re.: Application No. PCT/IL07/00918.
Invitation to Pay Additional Fees Dated Jul. 10, 2008 From the International Searching Authority Re.: Application No. PCT/IL06/01511.
Invitation to Pay Additional Fees Dated Feb. 15, 2007 From the International Searching Authority Re.: Application No. PCT/IL05/00575.
Notice of Allowance Dated Nov. 23, 2009 From the US Patent and Trademark Office Re.: U.S. Appl. No. 12/084,559.
Notice of Appeal and Pre-Appeal Brief Dated Jan. 4, 2010 to Official Action of Sep. 2, 2009 From the US Patent and Trademark Office Re.: U.S. Appl. No. 10/343,792.
Notice of Appeal Dated Nov. 16, 2009 to Official Action of Jul 15, 2009 From the US Patent and Trademark Office Re.: U.S. Appl. No. 10/616,301.
Office Action Dated Jan. 2, 2006 From the Israeli Patent Office Re.: Application No. 154323.
Office Action Dated Sep. 4, 2007 From the Israeli Patent Office Re.: Application No. 157007.
Official Action Dated Mar. 2, 2010 From the US Patent and Trademark Office Re.: U.S. Appl. No. 10/836,223.
Official Action Dated Mar. 2, 2010 From the US Patent and Trademark Office Re.: U.S. Appl. No. 11/980,617.
Official Action Dated Jul. 7, 2009 From the US Patent and Trademark Office Re.: U.S. Appl. No. 10/533,568.
Official Action Dated Dec. 8, 2009 From the US Patent amd Trademark Office Re.: U.S. Appl. No. 11/132,320.
Official Action Dated Jan. 8, 2010 From the US Patent and Trademark Office Re.: U.S. Appl. No. 11/656,548.
Official Action Dated Mar. 11, 2010 From the US Patent and Trademark Office Re.: U.S. Appl. No. 11/607,075.
Official Action Dated May 13, 2009 From the US Patent and Trademark Office Re.: U.S. Appl. No. 11/798,017.
Official Action Dated May 14, 2009 From the US Patent and Trademark Office Re.: U.S. Appl. No. 11/656,548.
Official Action Dated Dec. 16, 2008 From the US Patent and Trademark Office Re.: U.S. Appl. No. 10/343,792.
Official Action Dated Mar. 19, 2010 From the US Patent and Trademark Office Re.: U.S. Appl. No. 10/240,239.
Official Action Dated Dec. 23, 2008 From the US Patent and Trademark Office Re.: U.S. Appl. No. 09/727,464.
Official Action Dated Feb. 23, 2010 From the US Patent and Trademark Office Re.: U.S. Appl. No. 09/641,973.
Official Action Dated Nov. 26, 2008 From the US Patent and Trademark Office Re.: U.S. Appl. No. 10/240,239.
Official Action Dated Apr. 29, 2009 From the US Patent and Trademark Office Re.: U.S. Appl. No. 11/980,690.
Response Dated Apr. 7, 2009 to Official Action of Oct. 7, 2008 From the US Patent and Trademark Office Re.: U.S. Appl. No. 10/616,301.
Response Dated Mar. 13, 2008 to Official Action of Dec. 13, 2007 From the US Patent and Trademark Office Re.: U.S. Appl. No. 10/616,301.
Response Dated Aug. 14, 2008 to Official Action of Apr. 15, 2008 From the US Patent and Trademark Office Re.: U.S. Appl. No. 09/727,464.
Response Dated Jan. 14, 2010 to Official Action of Sep. 15, 2009 From the US Patent and Trademark Office Re.: U.S. Appl. No. 10/616,307.
Response Dated Jan. 14, 2010 to Official Action of Sep. 15, 2009 From the US Patent and Trademark Office Re.: U.S. Appl. No. 10/836,223.
Response Dated Mar. 15, 2007 to Official Action of Dec. 15, 2006 From the US Patent and Trademark Office Re.: U.S. Appl. No. 10/616,301.
Response Dated Jan. 21, 2010 to Official Action of Sep. 21, 2009 From the US Patent and Trademark Office Re.: U.S. Appl. No. 11/798,017.

Response Dated Feb. 22, 2010 to Communication Pursuant to Article 94(3) EPC of Oct. 21, 2009 From the European Patent Office Re.: Application No. 02716285.8.
Response Dated Sep. 22, 2008 to Official Action of Jun. 25, 2008 From US Patent and Trademark Office Re.: U.S. Appl. No. 10/616,301.
Response Dated Nov. 25, 2005 to Office Action of May 13, 2005 From the Patent Office of the People's Republic of China Re.: Application No. 1817689.5.
Response Dated Dec. 28, 2009 to Official Action of Aug. 28, 2009 From the US Patent and Trademark Office Re.: U.S. Appl. No. 10/240,239.
Response Dated Dec. 30, 2009 to Official Action of Sep. 1, 2009 From the US Patent and Trademark Office Re.: U.S. Appl. No. 11/794,799.
Response Dated Dec. 30, 2009 to Official Action of Oct. 30, 2009 From the US Patent and Trademark Office Re.: U.S. Appl. No. 11/980,690.
Response Dated Oct. 31, 2007 to Official Action of Jul. 12, 2007 From the US Patent and Trademark Office Re.: U.S. Appl. No. 10/616,301.
Response to the International Search Report and the Written Opinion of Oct. 10, 2006 From the International Searching Authority Re.: Application No. PCT/IL06/00059.
Second International Search Report Dated Jun. 1, 2009 From the International Searching Authority Re.: Application No. PCT/IL07/00918.
Supplementary Partial European Search Report and the European Search Opinion Dated Dec. 15, 2009 From the European Patent Office Re.: Application No. 06832278.3.
Translation of Office Action Dated May 13, 2005 From the Patent Office of the People's Republic of China Re.: Application No. 01817689.5.
Written Opinion Dated Oct. 15, 2008 From the International Searching Authority Re.: Application No. PCT/IL07/00918.
Bloch et al. "Application of Computerized Tomography to Radiation Therapy and Surgical Planning", Proceedings of the IEEE, 71(3): 351-355, Mar. 1983.
Gilland et al. "A 3D Model of Non-Uniform Attenuation and Detector Response for Efficient Iterative Reconstruction in SPECT", Physics in Medicine and Biology, XP002558623, 39(3): 547-561, Mar. 1994. p. 549-550, Section 2.3 'Active Voxel Reconstruction', p. 551, Lines 4-8.
Gilland et al. "Simultaneous Reconstruction and Motion Estimation for Gated Cardiac ECT", IEEE Transactions on Nuclear Science, XP011077797, 49(5): 2344-2349, Oct. 1, 2002. p. 2344, Section 'Introduction', First §.
Kadrmas et al. "Static Versus Dynamic Teboroxime Myocardial Perfusion SPECT in Canines", IEEE Transactions on Nuclear Science, 47(3): 1112-1117, Jun. 2000.
Li et al. "A HOTLink/Networked PC Data Acquisition and Image Reconstruction System for a High Resolution Whole-Body PET With Respiratory or ECG-Gated Performance", IEEE Nuclear Sience Symposium and Medical Imaging Conference, Norfolk, VA, USA, Nov. 10-16, 2002, XP010663724, 2: 1135-1139, Nov. 10, 2002. p. 1137, First col., 2nd §.
Official Action Dated Apr. 9, 2010 From the US Patent and Trademark Office Re.: U.S. Appl. No. 11/798,017.
Communication Pursuant to Article 93(3) EPC Dated Mar. 8, 2010 From the European Patent Office Re.: Application No. 06832278.3.
Official Action Dated Apr. 8, 2010 from the US Patent and Trademark Office Re.: U.S. Appl. No. 11/980,690.
Official Action Dated Apr. 28, 2010 From the US Patent and Trademark Office Re.: U.S. Appl. No. 10/616,301.
Response Dated May 10, 2010 to Official Action Apr. 8, 2010 From the US Patent and Trademark Office Re.: U.S. Appl. No. 11/980,690.
Response Dated May 10, 2010 to Official Action of Jan. 8, 2010 From the US Patent and Trademark Office Re.: U.S. Appl. No. 11/656,548.
Response Dated May 11, 2010 to Official Action of Mar. 11, 2010 From the US Patent and Trademark Office Re.: U.S. Appl. No. 11/607,075.

Response Dated May 26, 2010 to Official Action of Mar. 19, 2010 From the US Patent and Trademark Office Re.: U.S. Appl. No. 10/240,239.

Communication Pursuant to Article 94(3) EPC Dated Apr. 16, 2010 From the European Patent Office Re. Application No. 01951883.6.

Response Dated Jun. 3, 2010 to Notice of Appeal and Pre-Appeal Brief of Jan. 4, 2010 to Official Action of Sep. 2, 2009 From the U.S. Patent and Trademark Office Re.: U.S. Appl. No. 10/343,792.

Response Dated Jul. 1, 2010 to Official Action of Mar. 2, 2010 From the US Patent and Trademark Office Re.: U.S. Appl. No. 11/980,617.

Official Action Dated Jul. 19, 2010 From the US Patent and Trademark Office Re.: U.S. Appl. No. 11/607,705.

Official Action Dated Jul. 19, 2010 From the US Patent and Trademark Office Re.: U.S. Appl. No. 11/656,548.

Response Dated Jul. 1, 2010 to Official Action of Mar. 2, 2010 From the US Patent and Trademark Office Re.: U.S. Appl. No. 10/836,223.

Response Dated Jul. 8, 2010 to Official Action of Apr. 9, 2010 From the US Patent and Trademark Office Re.: U.S. Appl. No. 11/798,017.

Response Dated Jun. 23, 2010 to Official Action of Feb. 23, 2010 From the US Patent and Trademark Office Re.: U.S. Appl. No. 09/641,973.

*Primary Examiner*—Constantine Hannaher

(57) ABSTRACT

An electronic storage medium that comprises at least one radiopharmaceutical identity, SPECT measured values of at least one radiopharmaceutical kinetic parameter of a flow rate across a tissue membrane, for the radiopharmaceutical, and a set of instructions for associating the at least one radiopharmaceutical kinetic parameter with a disease signature.

22 Claims, 94 Drawing Sheets
(23 of 94 Drawing Sheet(s) Filed in Color)

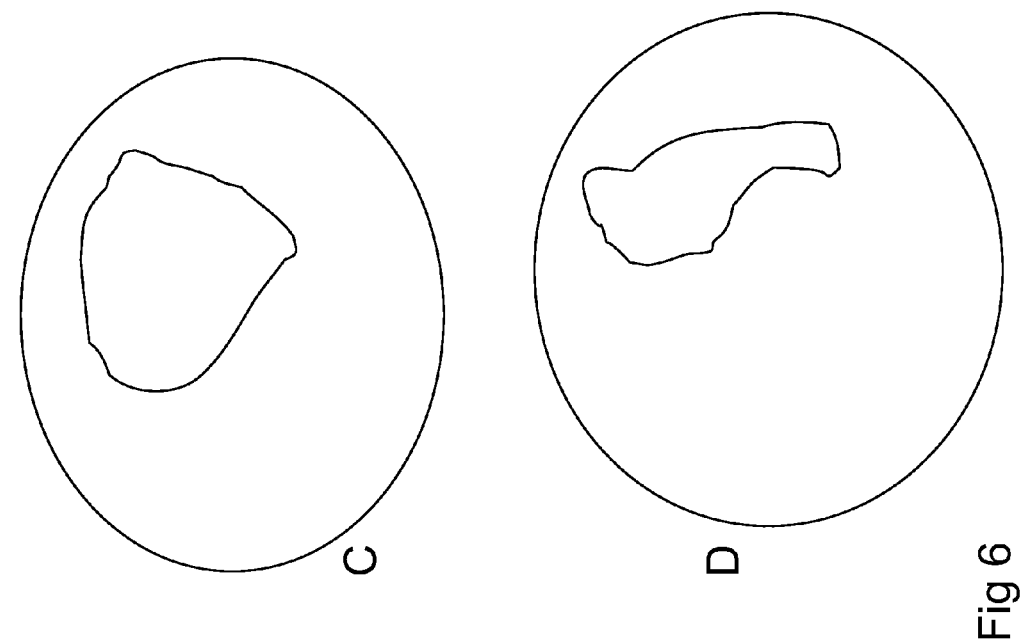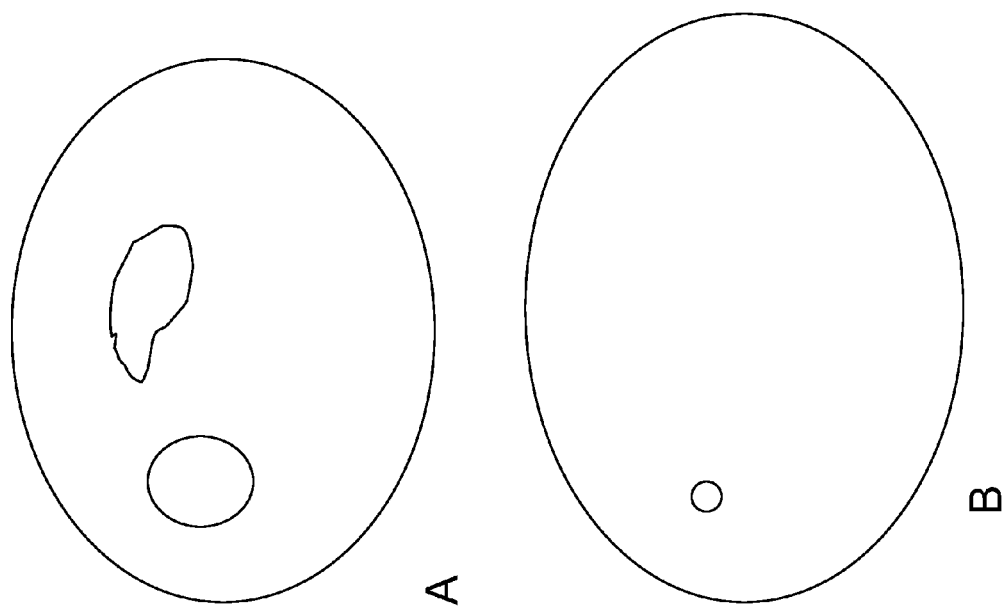
Fig 6

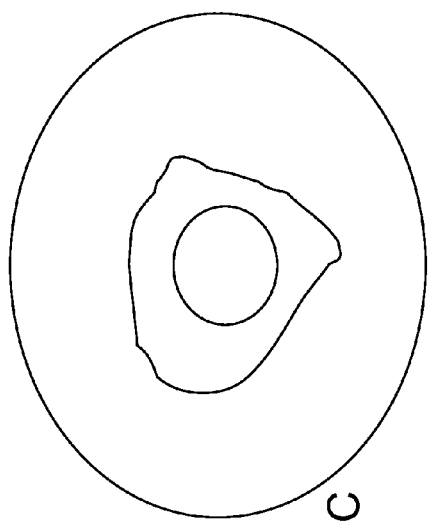
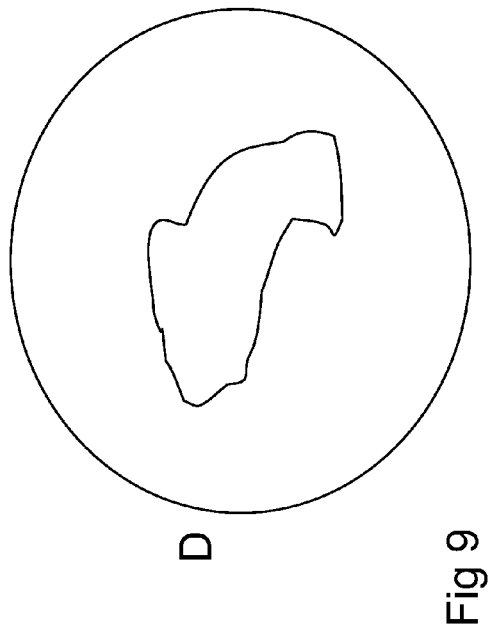
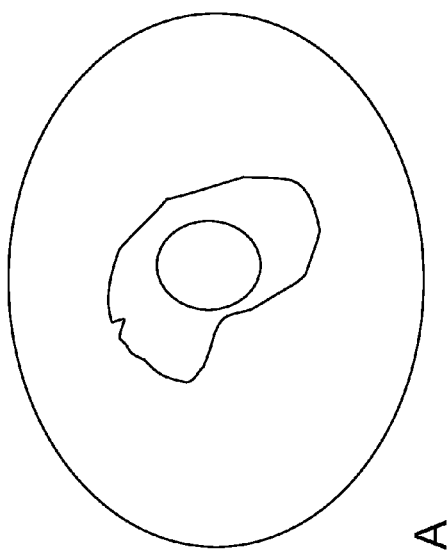
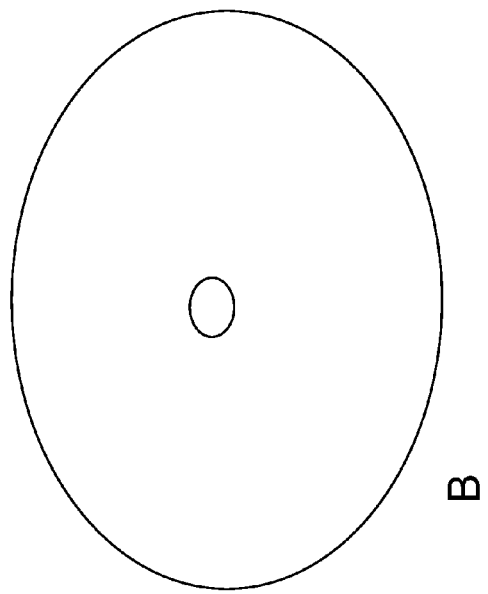
Fig 9

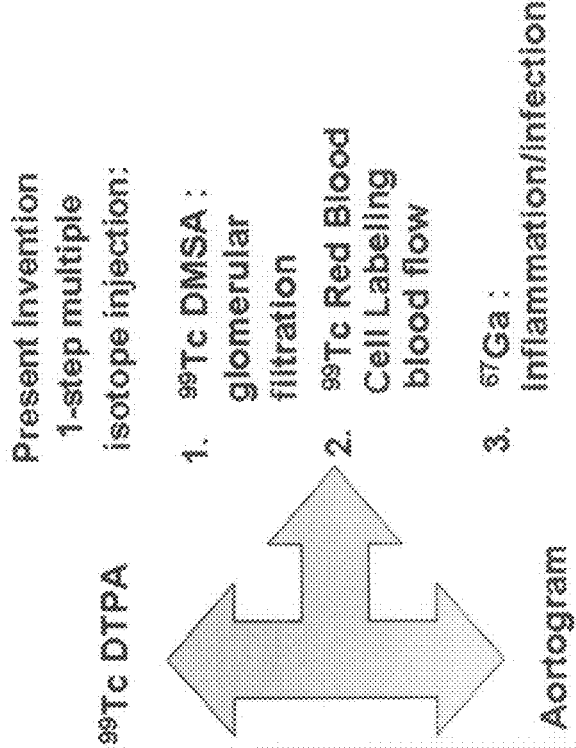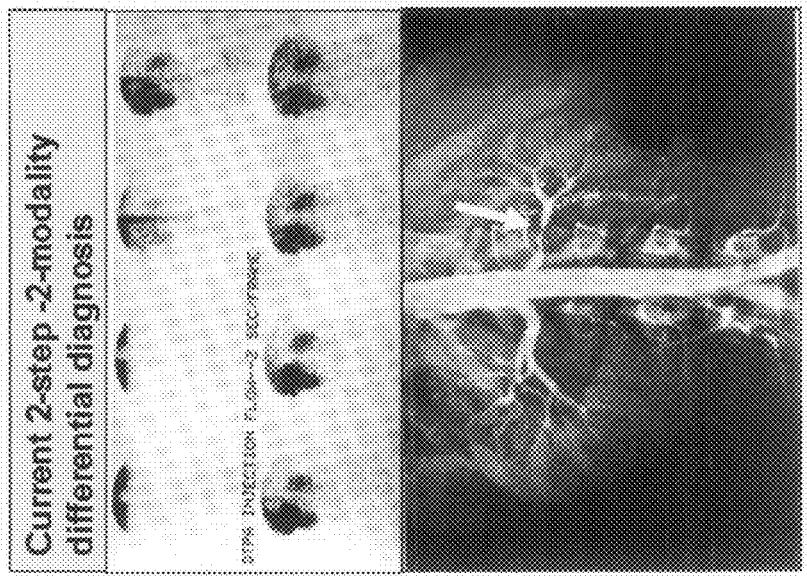
Figure 10B

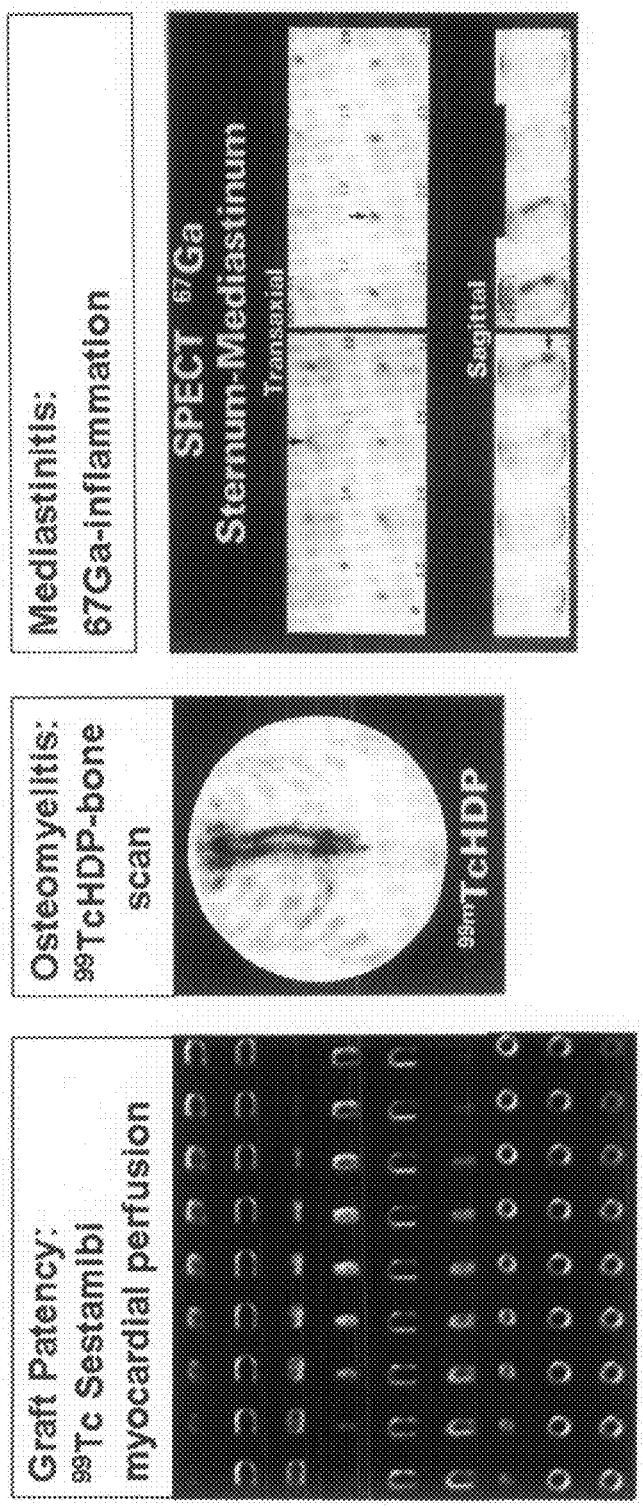

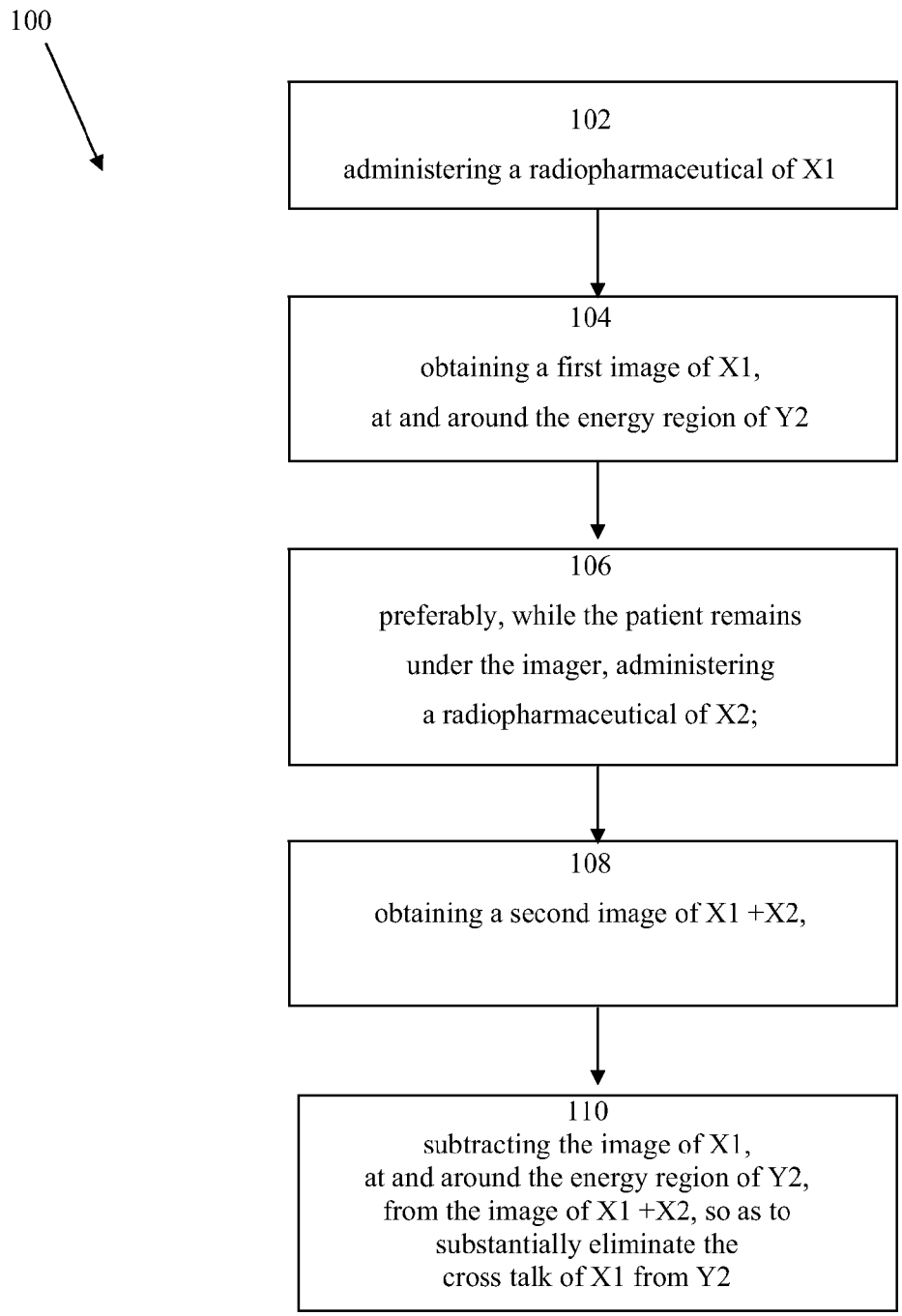

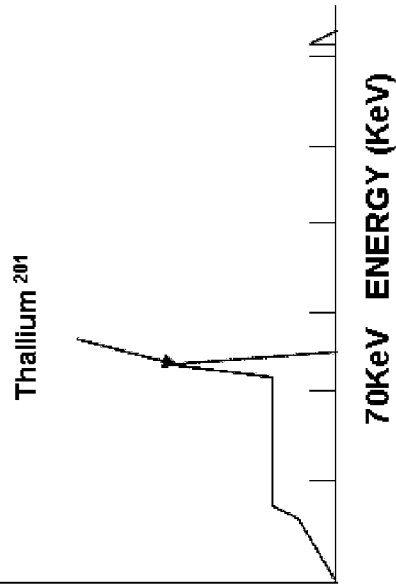
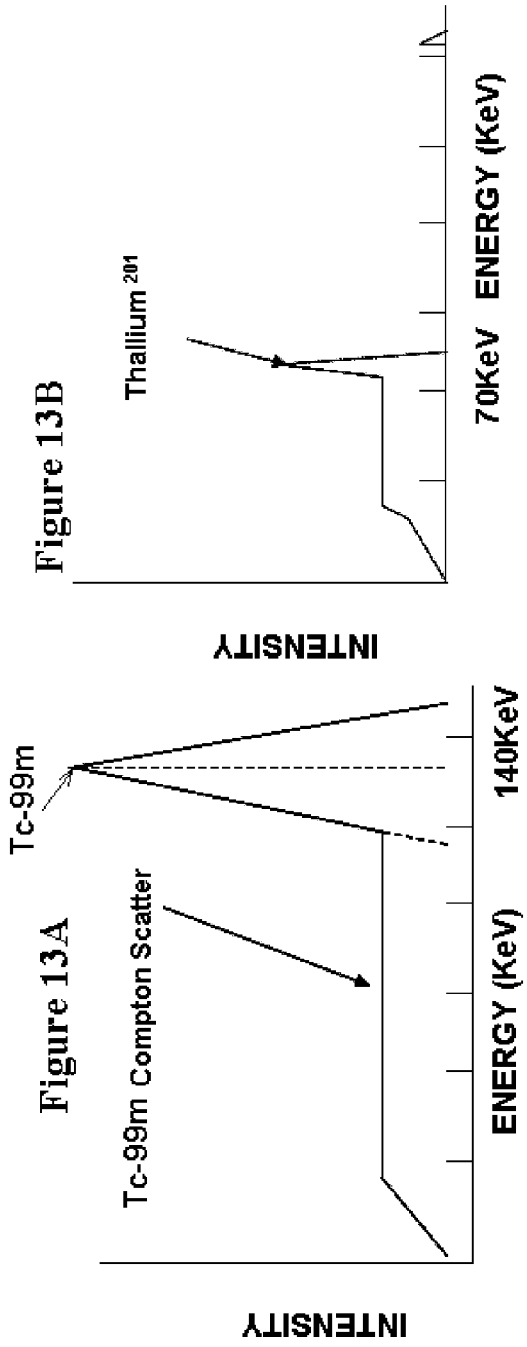
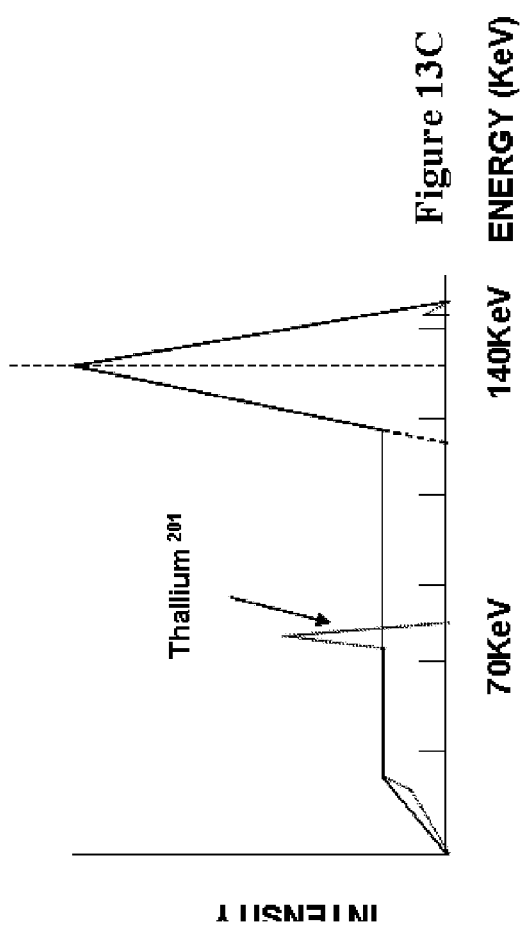

Figure 36 A

| Protocol | Rest injection | | Waiting time | Rest imaging | Stress |
|---|---|---|---|---|---|
| Standard protocol dual isotope-fast imaging | Tl | 3mCi | 10-15 min | 2 min | treadmill |
| Standard protocol-single isotope- fast imaging | Tc-MIBI | 8-10mCi | 30 min | 3 min | treadmill |
| Ultra-Fast dual-isotope Protocol | Tl | 3mCi | 2 min | 2 min | pharma |
| Ultra-Fast Single Isotope Protocol | Tc-MIBI | 8-10mCi | | 0.2min | pharma |
| Simultaneous dual-isotope Thallium stress perfusion | Tl | 3mCi | | | treadmill |
| Fast Thallium stress perfusion | Tc-MIBI | 3mCi | 30 min | 2 min | treadmill |
| Ultra-fast Thallium stress perfusion | Tc-MIBI | 3mCi | 30 min | 2min | pharma |
| Simultaneous Thallium stress perfusion | Tc-MIBI | 3mCi | 30 min | 0.2min | pharma |
| Teboroxime | Tc-MIBI | 3mCi | | 2min- then wait 0-10 min | exercise/ pharma |
| | Teboroxime | 8-10mCi | | | pharma |
| ***ALL STUDIES ARE GATED | | | | | |

Figure 30 B

| Protocol | Stress injection | | Waiting time | Post-stress gated imaging |
|---|---|---|---|---|
| Standard protocol-dual isotope-fast imaging | Tc-MIBI | 20-30mCi | 30 ~ 60 min | 2 min |
| Standard protocol-single isotope-fast imaging | Tc-MIBI | 20-30mCi | 30 ~ 60 min | 2 min |
| Ultra-Fast dual-isotope Protocol | Tc-MIBI | 20-30mCi | immediate | 2 min |
| Ultra-Fast Single Isotope Protocol | Tc-MIBI | 20-30mCi | immediate | 2 min |
| Simultaneous dual-isotope Thallium stress perfusion | Tc-MIBI | 20-30mCi | 30-60 min | 2 min |
|  | Tl | 3 mCi | 10-15 min | 4 min |
| Fast Thallium stress perfusion | Tl | 3 mCi | immediate | 4 min |
| Ultra-Fast Thallium stress perfusion | Tl | 3 mCi | 2 min | 0.4 min |
| Simultaneous Thallium stress perfusion | Tl | 3 mCi |  | 4 min |
| Teboroxime | Teboroxime | 20-30mCi |  | 0.2 min |
| ALL STUDIES ARE GATED | | | | |

Figure 30 C

| Protocol | Total Camera Time | Total Patient Time |
|---|---|---|
| Standard protocol- dual isotope-fast imaging | 4 min | 60-90 min |
| Standard protocol- single isotope-fast imaging | 4 min | 90 min |
| Ultra-Fast dual-isotope Protocol | 4 min | 20-30 min |
| Ultra-Fast Single Isotope Protocol | 4 min | 20-30 min |
| Simultaneous dual-isotope Thallium stress perfusion | 2 min | 60-90 min |
| Post Thallium stress perfusion | 6 min | 45-60 min |
| Ultra-Fast Thallium stress perfusion | 6 min | 20-30 min |
| Simultaneous Thallium stress perfusion | 6 min | 10-20 min |
| Teboroxime | 6 min | 10-20 min |
| *ALL STUDIES ARE GATED* | | |

Figure 30 D

| Protocol | Benefit | D-SPECT Requirements |
|---|---|---|
| Standard protocol- dual-isotope-fast imaging | rapid imaging (better resolution) | |
| Standard protocol- single-isotope-fast imaging | rapid imaging (better resolution) | |
| Ultra-Fast dual-isotope Protocol | rapid imaging; less binding by liver | pharmacological stress; all injections while positioned under the camera |
| Ultra-Fast Single Isotope Protocol | rapid imaging; less binding by liver one acquisition | pharmacological stress; all injections while positioned under the camera |
| Simultaneous dual-isotope | better registration of images- shortened overall imaging time | |
| Thallium stress perfusion | better flow linearity; ability to detect smaller lesions; viability | |
| Fast Thallium stress perfusion | better flow linearity; ability to detect smaller lesions; viability | pharmacological stress; all injections while positioned under the camera |
| Ultra-Fast Thallium stress perfusion | better flow linearity; ability to detect smaller lesions; viability;one acquisition | SD camera is not effected by liver uptake;pharmacological stress; all injections while positioned under the camera |
| Simultaneous Thallium stress perfusion | better registration of images- shortened overall imaging time | |
| Teboroxime | | |
| ALL STUDIES ARE GATED | | |

Figure 31 A

| Protocol | Clinical Significance | Radioisotope | Radiopharmaceutical |
|---|---|---|---|
| Lung V/P- DTPA aerosol and macro-aggregated albumin (lung perfusion agent) | Perfusion described by quantitative parameters (ml/min/gr) ; | Tc-99m I-123 | |
| MDP-bone scan-whole body scan | routinely performed to look for bone tumors or inflammatory processes of the bone (e.g. osteomyelitis) | Tc-99m | MDP |

Figure 31 B

| Protocol | Total Injected Dose | Time to acquisition |
|---|---|---|
| Lung V/P- DTPA aerosol and macro-aggregated albumin (lung perfusion agent) | MAA up to 5mCi (up to 1M particles) | immediate acquisition immediately after DTPA; MAA in injected and the immediate acquisition |
| MDP-bone scan-whole body scan | 20-30mCi | 0-60 min |

Figure 31 C

| Protocol | Acquisition protocol | Acquisition Time | Benefit |
|---|---|---|---|
| Lung V/P- DTPA aerosol and macro-aggregated albumin (lung perfusion agent) | energy window- anywhere between 3-15% | up to 6 min | fast |
| MDP-bone scan-whole body scan | energy window- anywhere between 3-15% | up to 6 min | fast |

Figure 32 A

| Protocol | Rest injection | | Waiting time | Rest imaging |
|---|---|---|---|---|
| Cardiac Standard protocol-dual isotope-low dose | Tl | 0.3mCi | 10-15 min | 15 min |
| Cardiac Standard protocol-single isotope-low dose | Tc-MIBI | 0.3mCi | 30 min | 15min |
| Cardiac Simultaneous dual-isotope-low dose | Tl | 0.3mCi | | |
| Cardiac Fast dual-isotope Protocol-low dose | Tl | 0.3mCi | 2 min | 15 min |
| Cardiac Fast Single Isotope Protocol-low dos | MIBI | 0.3mCi | | 0 15min |

Figure 32 B

| Protocol | Stress | Stress injection | |
|---|---|---|---|
| Cardiac Standard protocol-dual isotope-low dose | treadmill | Tc-MIBI | 3mCi |
| Cardiac Standard protocol-single isotope-low dose | treadmill | Tc-MIBI | 3mCi |
| Cardiac Simultaneous dual-isotope-low dose | treadmill/ pharma | Tc-MIBI | 3-5 mCi |
| Cardiac Fast dual-isotope Protocol-low dose | pharma | Tc-MIBI | 20-30mCi |
| Cardiac Fast Single Isotope Protocol-low dose | pharma | Tc-MIBI | 3mCi |

Figure 32 C

| Protocol | Waiting time | Post-stress gated imaging |
|---|---|---|
| Cardiac Standard protocol-dual isotope-low dose | 30 - 60 min | 15 min |
| Cardiac Standard protocol-single isotope-low dose | 30 - 60 min | 15 min |
| Cardiac Simultaneous dual-isotope-low dose | 30-60 min | 5-15 min |
| Cardiac Fast dual-isotope Protocol-low dose | 0 | 2 min |
| Cardiac Fast Single Isotope Protocol-low dose | 0 | 15 min |

Figure 32 D

| Protocol | Acquisition protocol | Benefit |
|---|---|---|
| Cardiac Standard protocol- dual isotope-low dose | energy window- anywhere between 3-15 | low dose (better resolution) |
| Cardiac Standard protocol- single isotope-low dose | energy window- anywhere between 3-15 | low dose (better resolution) |
| Cardiac Simultaneous dual-isotope-low dose | energy window- anywhere between 3-15 | one acquisition; low dose- better registration of images- shortened overall imaging time |
| Cardiac Fast dual-isotope Protocol-low dose | energy window- anywhere between 3-15% | |
| Cardiac Fast Single Isotope Protocol-low dose | energy window- anywhere between 3-15% | |

| Protocol | Comments 1 | Comments 2 |
|---|---|---|
| Cardiac Standard protocol-dual isotope-low dose | | |
| Cardiac Standard protocol-single isotope-low dose | | |
| Cardiac Simultaneous dual-isotope-low dose | | |
| Cardiac Fast dual-isotope Protocol-low dose | rapid imaging; less blinding by liver | pharmacologicol stress; all injections while positioned under the camera |
| Cardiac Fast Single Isotope Protocol-low dose | rapid imaging; less blinding by liver | pharmacologicol stress; all injections while positioned under the camera |

| Protocol | Clinical Significance | Radioisotope | Radiopharmaceutical | Total Injected Dose | Time to acquisition |
|---|---|---|---|---|---|
| Brain - Perfusion - Perfusion Mapping | Perfusion described by quantitative parameters (ml/min/gr) ; Cerebral Flow Reserve (in stress protocols using pharmacological stress agents); parametric quantitation; disease signature (Alzheimer's, depression, schizophrenia, etc.....) | Tc-99m I-123 | HMPAO ECD (neurolite) IMP (spectamine) | up to 3mCi for Tc-99m labeled up to 0.5mCi for I-123 | wait up to one hour after injection |
| Hepatobiliary - Tc99m sulfur colloid | routinely is done to look a the liver structure (hemangiomas, abcesses, liver enlargement, | Tc-99m I-123 | choletec | up to 0.5mCi | immediate acquisition |

Figure 33 A2

| Protocol | Acquisition protocol | Acquisition Time | Benefit |
|---|---|---|---|
| Brain - Perfusion - Perfusion Mappin | energy window- anywhere between 3-15% | 0-30 min | can show stroke at early stages |
| Hepatobiliary - Tc99m sulfur colloid | energy window- anywhere between 3-15% | 0-30 min | Study:<br>o Fluid flow<br>o Tracer rate of uptake (passive or active)<br>o Tracer accumulation/redistribution<br>o Tracer metabolism<br>o Tracer/metabolites secretion and/or washout (active or passive) |

Figure 33 B1

| Protocol | Clinical Significance | Radioisotope | Radiopharmaceutical | Total Injected Dose | Time to acquisition |
|---|---|---|---|---|---|
| Lung V/P- DTPA aerosol and macro-aggregated albumin (lung perfusion agent) | Perfusion described by quantitative parameters (ml/min/gr) ; | Tc-99m In-111 | | MAA up to 3mCi Tc-99m or 0.5mCi In-111 (up to 1M particles) | immediate acquisition immediately after DTPA; MAA in injected and the immediate acquisition |
| MDP-bone scan-whole body scan | routinely performed to look for bone tumors or inflammatory processes of the bone (e.g. osteomyelitis) | Tc-99m | MDP | 2-3mCi | 0-60 min |
| Kidney - Renal Function- Dynamic Flow Study 111In- DTPA & 99mTc- MAG3 | Assessment of filtration and tubular secretion; Perfusion described by quantitative parameters (ml/min/gr) parametric quantitation | Tc-99 In-111 | DTPA MAG3 | 0.2mCi In-111 up to 1mCi Tc-99m | 0 or before |

Figure 33 B2

| Protocol | Acquisition protocol | Acquisition Time | Benefit |
|---|---|---|---|
| Lung V/P- DTPA aerosol and macro-aggregated albumin (lung perfusion agent) | energy window- anywhere between 3-15% | 0-30 min | fast |
| MDP-bone scan-whole body scan | energy window- anywhere between 3-15% | up to 60 min | fast |
| Kidney - Renal Function- Dynamic Flow Study 111In- DTPA & 99mTc- MAG3 | energy window- anywhere between 3-15% | up to 30 min | Study:<br>o Fluid flow<br>o Tracer rate of uptake (passive or active)<br>o Tracer accumulation/redistribution<br>o Tracer metabolism<br>o Tracer/metabolites secretion and/or washout (active or passive) |

Figure 33 C1

| Protocol | Clinical Significance | Radioisotope | Radiopharmaceutical | Total Injected Dose | Time to acquisition |
|---|---|---|---|---|---|
| Kidney - Renal Function- Dynamic Flow Study 111In- DTPA & Hippuran I-123 | Assessment of filtration and tubular secretion; Perfusion described by quantitative parameters (ml/min/gr) parametric quantitation | Tc-99 I-123 | DTPA Hippuran | 0.3mCi I-123 up to 1mCi Tc-99m | |

Figure 33 C2

| Protocol | Acquisition protocol | Acquisition Time | Benefit |
|---|---|---|---|
| Kidney - Renal Function- Dynamic Flow Study 111In- DTPA & Hippuran I-123 | energy window- anywhere between 3-15% | up to 30 min | Study:<br>o Fluid flow<br>o Tracer rate of uptake (passive or active)<br>o Tracer accumulation/redistribution<br>o Tracer metabolism<br>o Tracer/metabolites secretion and/or washout (active or passive ) |

Figure 34 A1

| Protocol | Clinical Significance | Radioisotope | Radiopharmaceutical | Total Injected Dose |
|---|---|---|---|---|
| Cardiac-Perfusion 1 (Thallium rest) | Perfusion described by quantitative parameters (ml/min/gr) ; Coronary Flow Reserve; parametric quantitation | Tl-201 | Thallous Chloride - 201 | up to 4mCi |
| Cardiac-Perfusion 2 (Thallium stress) | Perfusion described by quantitative parameters (ml/min/gr) ; Coronary Flow Reserve; parametric quantitation | Tl-201 | Thallous Chloride - 201 | up to 4mCi |
| Cardiac-Perfusion 3 (Teboroxime rest) | Perfusion described by quantitative parameters (ml/min/gr) ; Coronary Flow Reserve; parametric quantitation | Tc-99m | Teboroxime | up to 30mCi |

Figure 34 A2

| Protocol | Time to acquisition | Acquisition protocol | Acquisition Time | Benefit |
|---|---|---|---|---|
| Cardiac-Perfusion 1 (Thallium rest) | 0 or before | energy window-anywhere between 3-15% | 2-20 minutes | Study:<br>o Fluid flow<br>o Tracer rate of uptake (passive or active)<br>o Tracer accumulation/redistribution<br>o Tracer metabolism<br>o Tracer/metabolites secretion and/or washout (active or passive) |
| Cardiac-Perfusion 2 (Thallium stress) | 0 or before | energy window-anywhere between 3-15% | 2-20 minutes | Study:<br>o Fluid flow<br>o Tracer rate of uptake (passive or active)<br>o Tracer accumulation/redistribution<br>o Tracer metabolism<br>o Tracer/metabolites secretion and/or washout (active or passive) |
| Cardiac-Perfusion 3 (Teboroxime rest) | 0 or before | energy window-anywhere between 3-15% | 0-15 minutes | Study:<br>o Fluid flow<br>o Tracer rate of uptake (passive or active)<br>o Tracer accumulation/redistribution<br>o Tracer metabolism<br>o Tracer/metabolites secretion and/or washout (active or passive) |

Figure 34 B1

| Protocol | Clinical Significance | Radioisotope | Radiopharmaceutical | Total Injected Dose |
|---|---|---|---|---|
| Cardiac-Perfusion 4 (Teboroxime stress) | Perfusion described by quantitative parameters (ml/min/gr) ; Coronary Flow Reserve; parametric quantitation | Tc-99m | Teboroxime | up to 30mCi |
| Cardiac-Perfusion 5 (Sestamibi rest) | Perfusion described by quantitative parameters (ml/min/gr) ; Coronary Flow Reserve; parametric quantitation | Tc-99m | Sestamibi | up to 30mCi |
| Cardiac-Perfusion 6 (Sestamibi stress) | Perfusion described by quantitative parameters (ml/min/gr) ; Coronary Flow Reserve; parametric quantitation | Tc-99m | Sestamibi | up to 30mCi |

Figure 34 B2

| Protocol | Time to acquisition | Acquisition protocol | Acquisition Time | Benefit |
|---|---|---|---|---|
| Cardiac-Perfusion 4 (Teboroxime stress) | 0 or before | energy window- anywhere between 3-15% | 0-15 minutes | Study:<br>o Fluid flow<br>o Tracer rate of uptake (passive or active)<br>o Tracer accumulation/redistribution<br>o Tracer metabolism<br>o Tracer/metabolites secretion and/or washout (active or passive) |
| Cardiac-Perfusion 5 (Sestamibi rest) | 0 or before | energy window- anywhere between 3-15% | 0-15 minutes | Study:<br>o Fluid flow<br>o Tracer rate of uptake (passive or active)<br>o Tracer accumulation/redistribution<br>o Tracer metabolism<br>o Tracer/metabolites secretion and/or washout (active or passive) |
| Cardiac-Perfusion 6 (Sestamibil stress) | 0 or before | energy window- anywhere between 3-15% | 0-15 minutes | Study:<br>o Fluid flow<br>o Tracer rate of uptake (passive or active)<br>o Tracer accumulation/redistribution<br>o Tracer metabolism<br>o Tracer/metabolites secretion and/or washout (active or passive) |

Figure 34 C1

| Protocol | Clinical Significance | Radioisotope | Radiopharmaceutical | Total Injected Dose |
|---|---|---|---|---|
| Cardiac-Perfusion 5 (Tetrofosmin rest) | Perfusion described by quantitative parameters (ml/min/gr); Coronary Flow Reserve; parametric quantitation | Tc-99m | Tetrofosmin | up to 30mCi |
| Cardiac-Perfusion 6 (Tetrofosmin stress) | Perfusion described by quantitative parameters (ml/min/gr); Coronary Flow Reserve; parametric quantitation | Tc-99m | Tetrofosmin | up to 30mCi |
| Cardiac-Perfusion 5 (Tc-99m-phosfurimine rest) | Perfusion described by quantitative parameters (ml/min/gr); Coronary Flow Reserve; parametric quantitation | Tc-99m | | up to 30mCi |

Figure 34 C2

| Protocol | Time to acquisition | Acquisition protocol | Acquisition Time | Benefit |
|---|---|---|---|---|
| Cardiac-Perfusion 5 (Tetrofosmin rest) | 0 or before | energy window-anywhere between 3-15% | 0-15 minutes | Study:<br>o Fluid flow<br>o Tracer rate of uptake (passive or active)<br>o Tracer accumulation/redistribution<br>o Tracer metabolism<br>o Tracer/metabolites secretion and/or washout (active or passive) |
| Cardiac-Perfusion 6 (Tetrofosmin stress) | 0 or before | energy window-anywhere between 3-15% | 0-15 minutes | Study:<br>o Fluid flow<br>o Tracer rate of uptake (passive or active)<br>o Tracer accumulation/redistribution<br>o Tracer metabolism<br>o Tracer/metabolites secretion and/or washout (active or passive) |
| Cardiac-Perfusion 5 (Tc-99m-phosfurimine rest) | 0 or before | energy window-anywhere between 3-15% | 0-15 minutes | Study:<br>o Fluid flow<br>o Tracer rate of uptake (passive or active)<br>o Tracer accumulation/redistribution<br>o Tracer metabolism<br>o Tracer/metabolites secretion and/or washout (active or passive) |

Figure 34 D1

| Protocol | Clinical Significance | Radioisotope | Radiopharmaceutical | Total Injected Dose |
|---|---|---|---|---|
| Cardiac-Perfusion 6 (Tc-99m-phosfurimine stress) | Perfusion described by quantitative parameters (ml/min/gr) ; Coronary Flow Reserve; parametric quantitation | Tc-99m | | up to 30mCi |
| BMIPP rest | Perfusion described by quantitative parameters (ml/min/gr) ; Coronary Flow Reserve; parametric quantitation; myocardial fatty acid metabolim | Tc-99m | | up to 30mCi |
| BMIPP stress | Perfusion described by quantitative parameters (ml/min/gr) ; Coronary Flow Reserve; parametric quantitation | Tc-99m | | up to 30mCi |

Figure 34 D2

| Protocol | Time to acquisition | Acquisition protocol | Acquisition Time | Benefit |
|---|---|---|---|---|
| Cardiac-Perfusion 6 (Tc-99m-phosfurimine stress) | 0 or before | energy window-anywhere between 3-15% | 0-15 minutes | Study:<br>o Fluid flow<br>o Tracer rate of uptake (passive or active)<br>o Tracer accumulation/redistribution<br>o Tracer metabolism<br>o Tracer/metabolites secretion and/or washout (active or passive ) |
| BMIPP rest | 0 or before | energy window-anywhere between 3-15% | | Study:<br>o Fluid flow<br>o Tracer rate of uptake (passive or active)<br>o Tracer accumulation/redistribution<br>o Tracer metabolism<br>o Tracer/metabolites secretion and/or washout (active or passive ) |
| BMIPP stress | 0 or before | energy window-anywhere between 3-15% | | Study:<br>o Fluid flow<br>o Tracer rate of uptake (passive or active)<br>o Tracer accumulation/redistribution<br>o Tracer metabolism<br>o Tracer/metabolites secretion and/or washout (active or passive ) |

Figure 34 E1

| Protocol | Clinical Significance | Radioisotope | Radiopharmaceutical | Total Injected Dose |
|---|---|---|---|---|
| Any one of the above combinations of rest and stress protocols | Perfusion described by quantitative parameters (ml/min/gr) ; Coronary Flow Reserve; parametric quantitation | | | |
| All PET radiopharmaceuticals within the currently used PET protocols used with our SPECT camera | Perfusion described by quantitative parameters (ml/min/gr) ; Coronary Flow Reserve; parametric quantitation | | | |
| Cancer - Tumor Perfusion. Evaluation of tumors by single isotope (nedd to expand on breast) SPECT with Teboroxime-Tc99m or 99mTc-MIBI or Tl-201 | Image tumor blood supply w/ 201Tl in combination with MIBI uptake and washout which is affected by the MDR complex showing therapeutic response to chemo. Perfusion described by quantitative parameters (ml/min/gr) ; parametric quantitation | Tc-99m | sestamibi | up to 30mCi for MIBI |

Figure 34 E2

| Protocol | Time to acquisition | Acquisition protocol | Acquisition Time | Benefit |
|---|---|---|---|---|
| Any one of the above combinations of rest and stress protocols | 0 or before | energy window- anywhere between 3-15% | | Study:<br>o Fluid flow<br>o Tracer rate of uptake (passive or active)<br>o Tracer accumulation/redistribution<br>o Tracer metabolism<br>o Tracer/metabolites secretion and/or washout (active or passive) |
| All PET radiopharmaceuticals within the currently used PET protocols used with our SPECT camera | 0 or before | energy window- anywhere between 3-15% | | Study:<br>o Fluid flow<br>o Tracer rate of uptake (passive or active)<br>o Tracer accumulation/redistribution<br>o Tracer metabolism<br>o Tracer/metabolites secretion and/or washout (active or passive) |
| Cancer - Tumor Perfusion. Evaluation of tumors by single isotope (need to expand on breast) SPECT with Teboroxime-Tc99m or 99mTc-MIBI or Tl-201 | 0 or before | energy window- anywhere between 3-15% | | Study:<br>o Fluid flow<br>o Tracer rate of uptake (passive or active)<br>o Tracer accumulation/redistribution<br>o Tracer metabolism<br>o Tracer/metabolites secretion and/or washout (active or passive) |

Figure 34 F1

| Protocol | Clinical Significance | Radioisotope | Radiopharmaceutical | Total Injected Dose |
|---|---|---|---|---|
| Cancer - Tumor Perfusion. Evaluation of tumors by simultaneous dual isotope SPECT with 201Tl-chloride and 99mTc-MIBI | Tumor imaging; Image tumor blood supply w/ 201Tl in combination with MIBI uptake and washout which is affected by the MDR complex showing therapeutic response to chemo. Perfusion described by quantitative parameters (ml/min/gr) ; parametric quantitation | Tl-201 Tc-99m | thallous chloride sestamibi | up to 4mCi for Tl-201 up to 30mCi for MIBI simultaneous injection |
| Kidney - Renal Function- Dynamic Flow Study 111In- DTPA & 99mTc-MAG3 | Assessment of filtration and tubular secretion; Perfusion described by quantitative parameters (ml/min/gr) parametric quantitation | Tc-99 In-111 | DTPA MAG3 | 0.2mCi-mCi In-111 up to 10mCi |
| Kidney - Renal Function- Dynamic Flow Study 111In- DTPA & Hippuran I-123 | Assessment of filtration and tubular secretion; Perfusion described by quantitative parameters (ml/min/gr) parametric quantitation | Tc-99 I-123 | DTPA Hippuran | 0.3mCi-1mCi I-123 up to 10mCi |

Figure 34 F2

| Protocol | Time to acquisition | Acquisition protocol | Acquisition Time | Benefit |
|---|---|---|---|---|
| Cancer - Tumor Perfusion. Evaluation of tumors by simultaneous dual isotope SPECT with 201Tl-chloride and 99mTc-MIBI | 0 or before | energy window- anywhere between 3-15% | | Study:<br>o Fluid flow<br>o Tracer rate of uptake (passive or active)<br>o Tracer accumulation/redistribution<br>o Tracer metabolism<br>o Tracer/metabolites secretion and/or washout (active or passive) |
| Kidney - Renal Function- Dynamic Flow Study 111In- DTPA & 99mTc-MAG3 | 0 or before | energy window- anywhere between 3-15% | | Study:<br>o Fluid flow<br>o Tracer rate of uptake (passive or active)<br>o Tracer accumulation/redistribution<br>o Tracer metabolism<br>o Tracer/metabolites secretion and/or washout (active or passive) |
| Kidney - Renal Function- Dynamic Flow Study 111In- DTPA & Hippuran I-123 | | | | Study:<br>o Fluid flow<br>o Tracer rate of uptake (passive or active)<br>o Tracer accumulation/redistribution<br>o Tracer metabolism<br>o Tracer/metabolites secretion and/or washout (active or passive) |

Figure 34 G1

| Protocol | Clinical Significance | Radioisotope | Radiopharmaceutical | Total Injected Dose |
|---|---|---|---|---|
| Brain - Perfusion - Perfusion Mapping | Perfusion described by quantitative parameters (ml/min/gr) ; Cerebral Flow Reserve (in stress protocols using pharmacological stress agents); parametric quantitation; disease signature (Alzheimer's, depression, schizophrenia, etc.....) | Tc-99m I-123 | HMPAO ECD (neurolite) IMP (spectamine) | up to 20mCi for Tc-99m labeled up to 5mCi for I-123 |
| Brain - Perfusion - Perfusion Mapping | Perfusion described by quantitative parameters (ml/min/gr) ; Cerebral Flow Reserve (in stress protocols using pharmacological stress agents); parametric quantitation; disease signature (Alzheimer's, depression, schizophrenia, etc.....) | Tc-99m | Teboroxime | up to 20mCi for Tc-99m labeled up to 5mCi |
| Hepatobiliary - Tc99m sulfur colloid | routinely is done to lok a the liver structure (hemangiomas, abcesses, liver enlargement, | | | up to 5mCi |

Figure 34 G2

| Protocol | Time to acquisition | Acquisition protocol | Acquisition Time | Benefit |
|---|---|---|---|---|
| Brain - Perfusion - Perfusion Mapping | 0 or before | energy window-anywhere between 3-15% | 0-30 min | Study:<br>o Fluid flow<br>o Tracer rate of uptake (passive or active)<br>o Tracer accumulation/redistribution<br>o Tracer metabolism<br>o Tracer/metabolites secretion and/or washout (active or passive) |
| Brain - Perfusion - Perfusion Mapping | 0 or before | energy window-anywhere between 3-15% | 0-30 min | Study:<br>o Fluid flow<br>o Tracer rate of uptake (passive or active)<br>o Tracer accumulation/redistribution<br>o Tracer metabolism<br>o Tracer/metabolites secretion and/or washout (active or passive) |
| Hepatobiliary - Tc99m sulfur colloid | immediate acquisition | | | Study:<br>o Fluid flow<br>o Tracer rate of uptake (passive or active)<br>o Tracer accumulation/redistribution<br>o Tracer metabolism<br>o Tracer/metabolites secretion and/or washout (active or passive) |

Figure 34 H1

| Protocol | Clinical Significance | Radioisotope | Radiopharmaceutical | Total Injected Dose |
|---|---|---|---|---|
| Liver function study | | Tc-99m | Disida (disulfenine) Choletec HIDA (all bind to bilirubin sites) | up to 10 mCi |

Figure 34 H2

| Protocol | Time to acquisition | Acquisition protocol | Acquisition Time | Benefit |
|---|---|---|---|---|
| Liver function study | 0 min. or less | | first 5 minutes should be a real dynamic study and then every 5 minutes for up to an hour; if no activity is seen in intestine a pharmocologicagent is used for gall bladder contraction | Study:<br>o Fluid flow<br>o Tracer rate of uptake (passive or active)<br>o Tracer accumulation/redistribution<br>o Tracer metabolism<br>o Tracer/metabolites secretion and/or washout (active or passive) |

Figure 35 A

| Protocol | Clinical Significance | Radioisotope | Radiopharmaceutical | Total Injected Dose |
|---|---|---|---|---|
| Dual phase gastric emptying o Ventricular function (ejection fraction w/*smart gating for DV/DT* | solid food : Tc99m-S-colloid labeled, liquid food: In-111-DTPA labeled | Tc-99m In-111 | Tc-Colloid DTPA | 3MBq 0.5 MBq |
| | see all cardiac protocols | see all cardiac protocols | see all cardiac protocols | see all cardiac protocols |

Figure 35 B

| Protocol | Time to acquisition | Acquisition protocol | Acquisition Time | Benefit |
|---|---|---|---|---|
| Dual phase gastric emptying | 1 day after DTPA injection and immediately after Tc99m injection | | | |
| o Ventricular function (ejection fraction w/ *smart gating for DV/DT* | | see all cardiac protocols | see all cardiac protocols | see all cardiac protocols |

Figure 35 C

| Protocol | Clinical Significance | Radioisotope | Radiopharmaceutical |
|---|---|---|---|
| vulnerable plaque-111In-Annexin and /or 99mTc-AcuTec | 99mTc-AcuTec attaches to activated platelets and shows thrombus, the Annexin attaches to apoptotic cells | In-111<br>Tc-99m | Annexin<br>Accutec |
| Prostascint | imaging of prostate metastasis and possibly primary cancer | In-111 | Prostascint |
| Octreotide | In-111-Octreotide (tumor imaging agent for SST-receptor expressing tumors) | In-111 | Octreotide |
| 99mTc-P829, Neotec® | Neuroendocrine tumors (Somatostatin receptors) | Tc99m | Neotec |
| 99mTc-P280, Acutect® | Thrombus detection; DVT and intratererial thromus in coronary and carotid arteries (GP IIb/IIIa receptors on platelets). | Tc99m | Acutect |
| 123I-MIBG (meta-iodo benzyl guanidine) | Tumor imaging (Pheochromocytoma) and or Myocardial failure;Adrenergic tissue uptake,Presynaptic adrenergic receptors | I-123 | MIBG |

Figure 35 D

| Protocol | Total Injected Dose |
|---|---|
| vulnerable plaque-111In-Annexin and /or 99mTc-AcuTec | |
| Prostascint | up to 5mCi |
| Octreotide | up to 5mCi |
| 99mTc-P829, Neotec® | up to 20mCi |
| 99mTc-P280, Acutect® | up to 20mCi |
| 123I-MIBG (meta-iodo benzyl guanidine) | up to 5mCi |

Figure 36 A1

| Protocol | Clinical Significance | Radioisotope | Radiopharmaceutical | Total Injected Dose | Time to acquisition |
|---|---|---|---|---|---|
| Gated Cardiac study during pharmacological stress | this will be a dynamic study to investigate the effects of stress ( adenosine -ice-water- etc.... Vasodilation) on the flow kinetics with Thallium | SEE ALL THALLIUM STUDIES IN CARDIAC SECTION | | | |
| Kidney function | this will be a dynamic study to investigate the effects of stress ( captopril; fusides etc....) on the flow kinetics with MA3 | | SEE ALL THALLIUM STUDIES IN CARDIAC SECTION | SEE ALL THALLIUM STUDIES IN CARDIAC SECTION | SEE ALL THALLIUM STUDIES IN CARDIAC SECTION |
| Gallbladder | cholesystochinin is administered when gallbladder shows activity but cannot empty - this is for differential diagnosis | | | | |

Figure 36 A2

| Protocol | Acquisition protocol | Acquisition Time | Benefit |
|---|---|---|---|
| Gated Cardiac study during pharmacological stress | SEE ALL THALLIUM STUDIES IN CARDIAC SECTION | SEE ALL THALLIUM STUDIES IN CARDIAC SECTION | SEE ALL THALLIUM STUDIES IN CARDIAC SECTION |
| Kidney function | | | |
| Gallbladder | | | |

Figure 36 B

| Protocol | Clinical Significance | Radioisotope | Radiopharmaceutical | Total Injected Dose | Time to acquisition |
|---|---|---|---|---|---|
| CNS | stimulate the brain (rapid blinking; flashlights) and study blood flow;epilepsy; etc..... | | | | |
| Comments | These should be standard protocols as performed today or in fast or low-dose protocols. What is important here is that this will be analyzed in a quantitative manner to studty the respose of the tissue to pharmacologic, mechanic or any other type of stress or stimulus to characterize the physiological response of the tissue in a dynamic and quantitative manner. This information will be used to identify disease signature, personalize patient therapy. | | | | |

| Protocol | Clinical Significance | Radioisotope | Radiopharmaceutical | Total Injected Dose |
|---|---|---|---|---|
| Bexaar dosimetry | determine the dose required to inject in order to administer an effective dose of 75 REM | I-131 | Bexaar | 5mCi/35mg protein |

Figure 37 A

| Protocol | Time to acquisition | Acquisition protocol | Acquisition Time | Benefit |
|---|---|---|---|---|
| Bexaar dosimetry | 3 acquisitions during the week to produce a graph of metabolism | energy window- anywhere between 3-15% | each scan up to 5 min | |

| Protocol | Clinical Significance |
|---|---|
| Cocktails for pathology and anatomy | |
| Tl-201 (parathyroid avid agent) and Tc99m pertechnetate (thyroid agent) | parathyroid adenoma imaging-anatomical differentiation of parathyroid from thyroid |
| Tc99m-MIBI (parathyroid avid agent) and I-123 (thyroid agent) | parathyroid adenoma imaging-anatomical differentiation of parathyroid from thyroid |
| I-131 with Tc99m-MDP or Tc99m-RBC | for imaging of thyroid cancer with anatomical registration of location (Tc99m-MDP - bone imaging agent visualizing the skeleton as anatomical landmark or Tc99m-RBC - blood pool imaging agent visualizing the larger blood vessels as anatomical landmark) |
| In-111-Octreotide with Tc99m-MDP | In-111-Octreotide (tumor imaging agent for SST-receptor expressing tumors) with Tc99m-MDP (bone imaging agent visualizing the skeleton as anatomical landmark) to optimally localize some endocrine tumors. |

Figure 38 A2

| Protocol<br>Cocktails for pathology and anatomy | Radioisotope | Radiopharmaceutical | Total Injected Dose |
|---|---|---|---|
| Tl-201 (parathyroid avid agent) and Tc-99m pertechnetate (thyroid agent) | Tl-201<br>Tc-99m | Thallous chloride<br>pertechnetate | up to 1mCi Tl-201<br>up to 15mCi Tc-99m |
| Tc-99m-MIBI (parathyroid avid agent) and I-123 (thyroid agent) | Tc-99m<br>I-123 | Sestamibi<br>Iodide | up to 15mCi Tc-99m<br>up to 100microCi I-123 |
| I-131 with Tc99m-MDP or Tc99m-RBC | I-131<br>Tc-99m | Iodide<br>MDP | up to 4mCi I-131<br>up to 10mCi MDP/RBC |
| In-111-Octreotide with Tc99m-MDP | In-111<br>Tc-99m | Octreotide<br>MDP | up to 3mCi In-111<br>up to 15mCi Tc-99m |

Figure 38 A3

| Protocol Cocktails for pathology and anatomy | Time to acquisition | Acquisition protocol | Acquisition Time |
|---|---|---|---|
| Tl-201 (parathyroid avid agent) and Tc99m pertechnetate (thyroid agent) | 10 min | energy window- anywhere between 2-10% | 5min |
| Tc99m-MIBI (parathyroid avid agent) and I-123 (thyroid agent) | 10 min | energy window- anywhere between 2-10% | 5min |
| I-131 with Tc99m-MDP or Tc99m-RBC | up to 2 hours up to 3 days after In-111 injection but not more than 2 hours after MDP injection | energy window- anywhere between 2-10% | up to 30 min |
| In-111-Octreotide with Tc99m-MDP | | energy window- anywhere between 2-10% | up to 30 min |

Figure 38 A4

| Protocol<br>Cocktails for pathology and anatomy | Benefit |
|---|---|
| Tl-201 (parathyroid avid agent) and Tc-99m pertechnetate (thyroid agent) | simultaneous acquisition saves time; no problems with registration; no questions of anatomical location |
| Tc99m-MIBI (parathyroid avid agent) and I-123 (thyroid agent) | simultaneous acquisition saves time; no problems with registration; no questions of anatomical location |
| I-131 with Tc99m-MDP or Tc99m-RBC | |
| In-111-Octreotide with Tc99m-MDP | |

Figure 38 B1

| Protocol | Clinical Significance |
|---|---|
| Prostascint and Tc99m-RBC | In-111 labeled monoclonal anti-tumoral antibodies (Prostascint - prostate specific membrane antigen (PMSA), with Tc99m-labeled RBC delineating vascular structures of the pelvis/abdomen and enabling the clinician to distinguish the blood vessels from the lymph nodes with pathologic uptake of antibodies. |
| Tc-99m-colloid In-111 WBC | Tc99m-colloid (bone-marrow imaging agent) and In-111 WBC (for bone infection |
| Tl-201 and Tc99m-MDP | Tl-201 (tumor imaging agent) and Tc99m-MDP (bone scan agent) SPECT to evaluate bone or cartilage invasion by head and neck cancer |
| Cocktails for multiple pathologies. Non-invasive biopsy | |
| Tl-201, MIBI, In-11 WBC. | This will be a very general multi-isotope for assessing most common medical problems: cardiac; tumor; infection |

Figure 38 B2

| Protocol | Radioisotope | Radiopharmaceutical | Total Injected Dose |
|---|---|---|---|
| Prostascint and Tc99m-RBC | In-111<br>Tc-99m | Prostascint<br>Tc-99m-RBC | up to 3mCi In-111<br>up to 15mCi Tc-99m |
| Tc-99m-colloid<br>In-111 WBC | Tc-99m<br>In-111 | Colloid<br>In-111 WBC | up to 3mCi In-111<br>up to 15mCi Tc-99m |
| Tl-201 and Tc99m-MDP | Tl-201<br>Tc-99m | Thallous chloride<br>MDP | up to 2mCi for Tl-201<br>up to 15mCi MDP |
| Cocktails for multiple pathologies: Non-invasive biopsy | | | |
| Tl-201, MIBI, In-111 WBC | Tl-201<br>Tc-99m<br>In-111 | Thallous chloride<br>MIBI<br>In-111 WBC | up to 1mCi for Tl-201<br>up to 10mCi for MIBI<br>up to 2mCi In-111 WBC |

Figure 38 B3

| Protocol | Time to acquisition | Acquisition protocol | Acquisition Time |
|---|---|---|---|
| Prostascint and Tc99m-RBC | up to 3 days after In-111 injection but not more than 2 hours after RBC injection | energy window- anywhere between 2-10% | up to 30 min |
| Tc-99m-colloid In-111WBC | up to 3 days after In-111 injection but not more than 2 hours after colloid injection?? | energy window- anywhere between 2-10% | up to 30 min |
| Tl-201 and Tc99m-MDP | up to 2 hours | energy window- anywhere between 2-10% | up to 30 min |
| Cocktails for multiple pathologies- Non-invasive biopsy | | | |
| Tl-201, MIBI, In-111WBC | up to 24 hours | energy window- anywhere between 2-10% | up to 30 min |

Figure 38 B4

| Protocol | Benefit |
|---|---|
| Prostascint and Tc99m-RBC | |
| Tc-99m-colloid In-111 WBC | |
| Tl-201 and Tc99m-MDP | |
| Cocktails for multiple pathologies- Non-invasive biopsy | non-invasive biopsy-one-stop diagnosis – many pathologies may be identified and characterized by a single scan |
| Tl-201, MIBI, In-111 WBC | |

Figure 38 C1

| Protocol | Clinical Significance |
|---|---|
| Tl-201; MDP; In-11WBC. Cocktails for different pathological processes of the same organ | This will be a very general multi-isotope for assessing most common medical problems: cardiac, tumor, infection |
| Tl-201/ OR Teboroxime, MIBI, BMIPP-I-123 | acute myocardial ischemia |
| NeutroSpect Tc-99m; WBC In-111 | Fever of Unknown Origin |
| I231-IBZM, Ceretec | Schizophrenia, Parkinson |
| In-111 ab Tc-MIBI/CEA, Tl | Tumor characterization- identification and perfusion |

Figure 38 C2

| Protocol | Radioisotope | Radiopharmaceutical | Total Injected Dose |
|---|---|---|---|
| Tl-201, MDP, In-111 WBC | Tl-201<br>Tc-99m<br>In-111 | Thallous chloride<br>MDP<br>In-111 WBC | up to 1mCi for Tl-201<br>up to 10mCi for MDP<br>up to 2mCi In-111 WBC |
| Cocktails for different pathological processes of the same organ | | | |
| Tl-201/ OR Teboroxime, MIBI, BMIPP, I-123 | Tl-201<br>Tc-99m<br>I-123 | Thallous chloride<br>MIBI<br>BMIPP | up to 1mCi for Tl-201<br>up to 10mCi for MIBI or teboroxime<br>up to 2mCi I-123 |
| NeuroSpect Tc-99m; WBC-In-111 | Tc-99m;<br>In-111 | NeuroSpect Tc-99m;<br>WBC-In-111 | up to 15mCi Tc-99m;<br>up to 2 mCi In-111 |
| I23I-IBZM, Ceretec | 123I; Ceretec | 123I-IBZM; Ceretec | up to 2mCi 123I;<br>up to 15 mCi Ceretec |
| In-111 ab Tc-MIBI/CEA, Tl | In-111 ab<br>Tc<br>Tl | In-111 ab Tc-MIBI/CEA, Tl | up to 2 mCi<br>up to 1mCi In-111 ab<br>up to 10mCiTc<br>up yo 1 mCi Tl |

Figure 38 C3

| Protocol | Time to acquisition | Acquisition protocol | Acquisition Time |
|---|---|---|---|
| Tl-201, MDP, In-111 WBC; Cocktails for different pathological processes of the same organ | up to 24 hours | energy window - anywhere between 2-10% | up to 30 min |
| Tl-201/ OR Teboroxime, MIBI, BMIPP-I-123 | up to 48 hours | energy window - anywhere between 2-10% | up to 30 min |
| NeutroSpect Tc-99m; WBC-In-111 | up to 24 hours | energy window - anywhere between 2-10% | up to 30 min |
| 123I-IBZM, Ceretec | up to 48 hours | energy window - anywhere between 2-10% | up to 30 min |
| In-111 ab Tc-MIBI/CEA, Tl | up to 24 hours | energy window - anywhere between 2-10% | up to 30 min |

Figure 38 C4

| Protocol | Benefit |
|---|---|
| Tl-201; MDP; In-11WBC; Cocktails for different pathological processes of the same organ | non-invasive biopsy;one-stop diagnosis-- many pathologies may be identified and characterized by a single scan |
| Tl-201 / OR Tebaroxime, MIBI, BMIPP-I-123 | comprehensive diffrential diagnosis in one step/ one scan |
| NeutraSpect Tc-99m; WBC-In-111 | comprehensive diffrential diagnosis in one step/ one scan |
| 123I-IBZM, Ceretec | comprehensive diffrential diagnosis in one step/ one scan |
| In-111 ab Tc-MIBI,CEA, Tl | comprehensive diffrential diagnosis in one step/ one scan |

Figure 38 D1

| Protocol | Clinical Significance |
|---|---|
| 111In- DTPA & 99mTc- MAG3 | Renal Function- Dynamic Flow Study |
| 201Tl or 99mTc-Teboroxime & 99mTc-MIBI | Tumor Perfusion & Therapeutic response (MDR): |
| 99mTc-sulfor colloid & 111In-WBC | Infection vs. bone marrow activation |
| 99mTc-MDP & 111In-WBC. | Acute Osteomyelitis vs. "old": |
| Ga67 & 111In-WBC | Acute vs. chronic Inflammation: |
| 99mTc-Teboroxine / OR Tl 111In-Annexin | Myocardial perfusion and Apoptosis |
| 201Tl Myocardial perfusion 99mTc-PYP Infarct Imagin | Myocardial perfusion and infarct |

Figure 38 D2

| Protocol | Radioisotope | Radiopharmaceutical | Total Injected Dose |
|---|---|---|---|
| 111In- DTPA & 99mTc- MAG3 | 111In- 99mTc- | 111In- DTPA & 99mTc- MAG3 | up to 2mCi 111In- up to 15 mCi 99mTc- |
| 201Tl or 99mTc-Teboroxime & 99mTc-MIBI | 201Tl or 99mTc 99mTc-MIBI | 201Tl or 99mTc-Teboroxime & 99mTc-MIBI | up to 1 mCi 201Tl or up to 15 mCi 99mTc teboroxime OR 99mTc-MIBI |
| 99mTc-sulfor colloid & 111In-WBC | 99mTc-sulfor colloid 111In-WBC | 99mTc-sulfor colloid & 111In-WBC | up to 15mCi 99mTc-sulfor colloid up to 2mCi 111In-WBC |
| 99mTc-MDP & 111In-WBC. | 99mTc 111In | 99mTc-MDP & 111In-WBC. | up to 15mCi 99mTc-MDP up to 2mCi 111In-WBC |
| Ga67 & 111In-WBC | Ga67 111In | Ga67 & 111In-WBC | up to 5mCi Ga67 up to 2mCi 111In |
| 99mTc-Teboroxine / OR Tl 111In-Annexin | 99mTc In-111 | 99mTc-Teboroxine / OR Tl 111In-Annexin | up to 2mCi 111In- up to 15 mCi 99mTc- |
| 201Tl Myocardial perfusion 99mTc-PYP Infarct Imagin | Tl-201 99m-Tc | 201Tl 99mTc-PYP | up to 2mCi Tl-201 up to 15 mCi 99mTc- |

Figure 38 D3

| Protocol | Time to acquisition | Acquisition protocol | Acquisition Time |
|---|---|---|---|
| 111In- DTPA & 99mTc- MAG3 | up to 24 hours | energy window- anywhere between 2-10% | up to 30 min |
| 201Tl or 99mTc-Teboroxime & 99mTc-MIBI | up to 1 hour | energy window- anywhere between 2-10% | up to 30 min |
| 99mTc-sulfor colloid & 111In-WBC | up to 24 hours | energy window- anywhere between 2-10% | up to 30 min |
| 99mTc-MDP & 111In-WBC. | up to 24 hours | energy window- anywhere between 2-10% | up to 30 min |
| Ga67 & 111In-WBC | up to 72 hours | energy window- anywhere between 2-10% | up to 30 min |
| 99mTc-Teboroxine / OR Tl 111In-Annexin | up to 24 hours | energy window- anywhere between 2-10% | up to 30 min |
| 201Tl Myocardial perfusion 99mTc-PYP Infarct Imagin | up to 1 hour | energy window- anywhere between 2-10% | up to 30 min |

Figure 38 D4

| Protocol | Benefit |
|---|---|
| 111In- DTPA & 99mTc- MAG3 | comprehensive diffrential diagnosis in one step/ one scan |
| 201Tl or 99mTc-Teboroxime & 99mTc-MIBI | comprehensive diffrential diagnosis in one step/ one scan |
| 99mTc-sulfor colloid & 111In-WBC | comprehensive diffrential diagnosis in one step/ one scan |
| 99mTc-MDP & 111In-WBC. | comprehensive diffrential diagnosis in one step/ one scan |
| Ga67 & 111In-WBC | comprehensive diffrential diagnosis in one step/ one scan |
| 99mTc-Teboroxine / OR Tl 111In-Annexin | comprehensive diffrential diagnosis in one step/ one scan |
| 201Tl  Myocardial perfusion 99mTc-PYP  Infarct Imagin | comprehensive diffrential diagnosis in one step/ one scan |

MULTI-DIMENSIONAL IMAGE RECONSTRUCTION AND ANALYSIS FOR EXPERT-SYSTEM DIAGNOSIS

RELATED APPLICATIONS

This Application is a National Phase of PCT Patent Application No. PCT/IL2006/000059 having International Filing Date of Jan. 15, 2006, which is a Continuation-in-Part of U.S. patent application Ser. No. 11/034,007 filed on Jan. 13, 2005.

This Application is also a Continuation-in-Part of PCT Patent Application Nos. PCT/IL2005/001215 filed on Nov. 16, 2005, PCT/IL2005/001173 filed on Nov. 9, 2005, PCT/IL2005/000575 filed on Jun. 1, 2005, PCT/IL2005/000572 filed on Jun. 1, 2005 and PCT/IL2005/000048 filed on Jan. 13, 2005.

This Application claims the benefit of Israel Patent Application Nos. 172349 filed on Nov. 27, 2005 and 171346 filed on Oct. 10, 2005.

This Application claims the benefit of U.S. Provisional Patent Application Nos. 60/750,597 filed on Dec. 15, 2005, 60/750,334 filed on Dec. 15, 2005, 60/750,287 filed on Dec. 13, 2005, 60/741,440 filed on Dec. 2, 2005, 60/720,652 filed on Sep. 27, 2005, 60/720,541 filed on Sep. 27, 2005, 60/720,034 filed on Sep. 26, 2005, 60/702,979 filed on Jul. 28, 2005, 60/700,753 filed on Jul. 20, 2005, 60/700,752 filed on Jul. 20, 2005, 60/700,318 filed on Jul. 19, 2005, 60/700,317 filed on Jul. 19, 2005, 60/700,299 filed on Jul. 19, 2005 and 60/691,780 filed on Jun. 20, 2005. The contents of the above Applications are all incorporated herein by reference.

FIELD AND BACKGROUND OF THE INVENTION

The present invention relates to multi-dimensional image reconstruction and analysis, and more particularly, but not exclusively to such image reconstruction of radioactive source or sources, directed to expert-system diagnosis.

Radionuclide imaging aims at obtaining an image of a radioactively labeled substance, that is, a radiopharmaceutical, within the body, following administration, generally, by injection. The substance is chosen so as to be picked up by active pathologies to a different extent from the amount picked up by the surrounding healthy tissue; in consequence, the pathologies are operative as radioactive-emission sources and may be detected by radioactive-emission imaging. A location of pathology may appear as a concentrated source of high radiation, that is, a hot region, as may be associated with a tumor, or as a region of low-level radiation, which is nonetheless above the background level, as may be associated with carcinoma.

A reversed situation is similarly possible. Dead tissue has practically no pick up of radiopharmaceuticals, and is thus operative as a cold region.

The mechanism of localization of a radiopharmaceutical in a particular organ of interest depends on various processes in the organ of interest such as antigen-antibody reactions, physical trapping of particles, receptor-site binding, removal of intentionally damaged cells from circulation, and transport of a chemical species across a cell membrane and into the cell by a normally operative metabolic process.

The particular choice of a radionuclide for labeling antibodies depends upon the chemistry of the labeling procedure and the isotope nuclear properties, such as the number of gamma rays emitted, their respective energies, the emission of other particles such as beta or positrons, the isotope half-life, and the decay scheme.

In PET imaging, positron emitting radio-isotopes are used for labeling, and the imaging camera detects coincidence photons, the gamma pair of 0.511 Mev, traveling in opposite directions. Each coincidence detection defines a line of sight, along which annihilation takes place. As such, PET imaging collects emission events, which occurred in an imaginary tubular section enclosed by the PET detectors. A gold standard for PET imaging is PET $NH_3$ rest myocardial perfusion imaging with N-13-ammonia ($NH_3$), at a dose level of 740 MBq, with attenuation correction. Yet, since the annihilation gamma is of 0.511 Mev, regardless of the radio-isotope, PET imaging does not provide spectral information, and does not differentiate between radio-isotopes.

In SPECT imaging, primarily gamma emitting radio-isotopes are used for labeling, and the imaging camera is designed to detect the actual gamma emission, generally, in an energy range of approximately 11-511 KeV. Generally, each detecting unit, which represents a single image pixel, has a collimator that defines the solid angle from which radioactive emission events may be detected.

Because PET imaging collects emission events, in the imaginary tubular section enclosed by the PET detectors, while SPECT imaging is limited to the solid collection angles defined by the collimators, generally, PET imaging has a higher sensitivity and spatial resolution than does SPECT. Therefore, the gold standard for spatial and time resolutions in nuclear imaging is defined for PET.

The radiopharmaceutical behavior in vivo is a dynamic process. Some tissues absorb radiopharmaceuticals faster than others or preferentially to others, and some tissues flush out the radiopharmaceuticals faster than others or preferentially to others, so the relative darkness of a given tissue is related to a time factor. Since the uptake clearance of such a radiopharmaceutical by the various tissues (target and background) varies over time, standard diagnosis protocols usually recommend taking an image at the time at which the ratio of target emission versus background emission is the highest.

Yet, this approach produces a single parameter per voxel of the reconstructed image, a level of gray, at a specific time, and ignores the information that could be obtained from the behavior of a radiopharmaceutical as a function of time.

Dynamic imaging, on the other hand, attempts to acquire the behavior of a radiopharmaceutical as a function of time, for example, to measure perfusion in myocardial tissue. Dynamic imaging is advantageous to static imaging, as it provides a better measure of blood flow, it is more sensitive to ischemia than static imaging, and both perfusion and myocardial viability may be obtained from a single imaging session.

Garcia et al. (Am. J. Cardiol. 51$^{st}$ Annual Scientific Session, 2002) describe a dynamic SPECT acquisition, using Tc-99m-teboroxime as a myocardial perfusion tracer. Dual, 90° detectors were fanned 180° every 36 seconds, for up to 4 minutes. All the fanned projections were mathematically combined to yield a "static" acquisition to reduce artifacts by accounting for both changing myocardial concentration and increasing liver activity. The purpose of the investigation was to test the quality and accuracy of images from this protocol.

Ronald H. Huesmany, Bryan W. Reuttery, G. Larry Zengz and Grant T. Gullberg (Kinetic Parameter Estimation from SPECT Cone-Beam Projection Measurements, 1997 International Meeting on Fully 3-D Image Reconstruction Conference Record, pages 121-125) describe a method for obtaining radiopharmaceutical kinetic parameters from SPECT. The kinetic parameters are commonly estimated from dynamically acquired nuclear medicine data by reconstructing a dynamic sequence of images and subsequently fitting the parameters to time activity curves generated from regions of interest overlaid upon the reconstructed image sequence. Since SPECT data acquisition involves movement of the detectors, and the distribution of radiopharmaceutical changes during the acquisition, the image reconstruction step can produce erroneous results that lead to biases in the estimated kinetic parameters. If the SPECT data are acquired using cone-beam collimators, wherein the gantry rotates so that the focal point of the collimators always remains in a plane, the additional problem of reconstructing dynamic images from insufficient projection samples arises. The reconstructed intensities will also have errors due to insufficient acquisition of cone-beam projection data, thus producing additional biases in the estimated kinetic parameters.

To overcome these problems, the authors investigated the estimation of the kinetic parameters directly from the projection data by modeling the data acquisition process of a time-varying distribution of radiopharmaceutical detected by a rotating SPECT system with cone-beam collimation. To accomplish this it was necessary to parameterize the spatial and temporal distribution of the radiopharmaceutical within the SPECT cone-beam field of view. The authors hypothesized that by estimating directly from cone-beam projections instead of from reconstructed time-activity curves, the parameters which describe the time-varying distribution of radiopharmaceutical could be estimated without bias.

In a private communication, on Nov. 2, 2005, Gullberg reports:

"In the 90s we had some success with obtaining measurements of flow-times-extraction and distribution volume with dynamic SPECT using the radiopharmaceutical Tc-99m-teboroxime. This agent has a fast washin and washout from the myocardial tissue. A 3 detector PRISM 300XP SPECT system (Picker) was able to acquire 128×128×120 views ever 5 seconds. This gave good timing resolution but the photon statistics were low even with an injection of 20 to 30 mCi of $^{99m}$Tc-teboroxime. However, even with these low statistics, one was able to show improved contrast for lesion detection as compared with static imaging using $^{201}$Tl. Also, one was able to obtain values of coronary flow reserve; however, these values were lower than the gold standard of dynamic PET using $^{13}$NH$_3$. The low statistics produced bias in our estimates of flow-times-extraction and increased the variance in the estimated parameters, especially for the nonlinear parameter that measured the washout from the tissue. The detector efficiency and speed of rotation limits the photon yield and timing resolution for measuring a dynamic agent. The SPECT systems of today have moved away from systems that can acquire any type of dynamic data. These are large rotating gamma cameras that are designed to perform static cardiac SPECT and whole body imaging in a single system. The timing resolution is very poor, approximately 14 seconds as compared with our previous 5 seconds. Added to this is the fact that good flow agents such as $^{99m}$Tc-teboroxime are no longer on the market because these systems cannot adequately image the fast turnover in the tissue."

Multiple-isotopes analysis is known. For example, U.S. Pat. No. 5,249,124, to DeVito, issued on September 1993, "Multi-isotope imaging using energy-weighted acquisition for, e.g., myocardial perfusion studies," describes a study, carried out imaging a plurality of imaging agents, simultaneously. The information obtained was weighted using as many energy weighting functions as there were isotopes. The weighting reduces "crosstalk" between each of the single-isotope images, thus producing improved results, for example, in dual-isotope (Tc-99m and Tl-201) myocardial perfusion studies.

Radiopharmaceutical imaging, while providing functional information regarding tissue viability and function, provides little structural information. In essence, two types of medical images may be distinguished:

1. functional body images, such as may be produced by gamma camera, SPECT, and PET scans, after the injection of a radiopharmaceutical, to provide physiological information; and
2. structural images, such as may be produced by as x-ray, CT, ultrasound, and (or) MRI scans, to provide anatomic, or structural maps of the body, for example, by distinguishing bones, fat, and muscle tissue.

Techniques for registering functional and structural images on a same system of coordinates, to produce a combined or fused image, are known, and are disclosed, for example in the publication to D. A. Weber and M. Ivanovic, "Correlative image registration", Sem. Nucl. Med., vol. 24 pp. 311-323 (1994), as well as in K. Kneöaurek, M. Ivanovic, J. Machac, and D. A. Weber, "Medical image registration," Europhysics News (2000) Vol. 31 No. 4, in U.S. Pat. No. 6,212,423, to Krakovitz, dated, Apr. 3, 2001, and entitled Diagnostic hybrid probes, in U.S. Pat. No. 5,672,877, to Liebig, et al., dated Sep. 30, 1997 and entitled, "Coregistration of multi-modality data in a medical imaging system," in U.S. Pat. No. 6,455,856, to Gagnon, dated, Sep. 24, 2002 and entitled, "Gamma camera gantry and imaging method," and in commonly owned U.S. Pat. No. 6,567,687, to Front et al., issued on May 20, 2003, and entitled, "Method and system for guiding a diagnostic or therapeutic instrument towards a target region inside the patient's body," all of whose disclosures are incorporated herein by reference.

These techniques may be used, for example, in order to identify features seen on the functional map, based on their anatomic location in the structural map.

Additionally, they may be used to provide attenuation correction to the radiopharmaceutical image. Attenuation refers to the loss of information due to the interaction of emitted photons with matter, through photon absorption by the photoelectric effect, photon scatter by the Compton effect, and pair production involving photons of energies greater than 1.02 Mev. Attenuation decreases the number of photon counts from that which would have been recorded in vacuum.

Various methods of attenuation corrections are known.

Emission-transmission imaging combines anatomical (structural) information from x-ray transmission images with physiological (functional) information from radiopharmaceutical emission images. By correlating the emission and transmission images, an observer may identify and delineate the location of the radiopharmaceutical source. In addition, the quantitative accuracy of measurement of radiopharmaceutical source is improved through use of iterative reconstruction methods.

For example, PCT Application PCT/US90/03722, to Kaplan, describes an emission-transmission system in which the emission data from a radiopharmaceutical to and transmission data from an x-ray source are acquired with the same detector (single or multiple heads). An alternative emission-transmission imaging system, disclosed in SU-1405-819-A, uses x-ray transmission data and two detectors for determining the direction of the photons to improve detection efficiency. However, an exact method of correcting emission data based on transmission data is not described by either Kaplan or in SU-1405-819-A.

Commonly owned PCT Publication WO2004/042546, whose disclosure is incorporated herein by reference, describes systems for radiopharmaceutical or x-ray imaging, with attenuation correction by another modality, of a completely different nature, for example, MRI or ultrasound, thus avoiding the iterative process when correcting emission information by transmission information—both being information of similar nature. PCT Publication WO2004/042546 describes a system comprising, a first device, for obtaining a first image, by a first modality, such as gamma scan or x-ray, a second device, for obtaining a second, structural image, by a second modality, such as MRI or ultrasound, and a computerized system, configured to display an attenuation-corrected first image and a superposition of the attenuation-corrected first image and the second, structural image. Furthermore, the system is operative to guide an in-vivo instrument based on the superposition.

SUMMARY OF THE INVENTION

The present invention relates to the capabilities of a highly sensitive radioactive-emission camera, a result of a meticulous search for the many different effects that combine synergistically to increase sensitivity and spatial, spectral, and time resolutions. The new camera opens a new realm in SPECT-type imaging, making it viable for dynamic studies, the use of radiopharmaceutical cocktails, molecular imaging, dosimetry and other studies requiring the high sensitivity and resolutions. In particular, the new camera opens the door to SPECT expert system, examples for which are provided.

The expert system relates to defining disease signatures for automatic diagnosis, preferably, based on a multi-parameter vector, preferably, based on kinetic radiopharmaceutical values. Additionally or alternatively, based on simultaneous administration of multiple isotopes.

The effects, which were combined to increase the camera's sensitivity and resolutions, are as follows:

1. solid collection angles greater than 0.1 or 0.15 steradians;
2. close proximity of the detectors to the body, in order to increase both:
   i. detection efficiency, which falls as a proportionally to the square of the distance from an object; and
   ii. resolution, where the number of detector pixels which view an object also falls proportionally to the square of the distance from the object;
3. windshield-wiper sweeping motions, with a center of rotation outside the patient's body, to maximize the information obtained from each x;y;z detector position;
4. trio-vision of each voxel, wherein each voxel is viewed with x, y, and z, components, as opposed to stereo vision in a plane, with only x and y components of state-of-the-art cameras;
5. Focus on a region of interest, by:
   i. prescanning;
   ii. independent motion of detectors, for independent focusing on ROI, by each detector;
   iii. applying algorithm which select a preferred set of views to for ROI focusing, based on the geometry of the organ to be imaged;
   iv. zooming in, by a second algorithmtic iteration, to select a preferred set of views based on earlier findings;
   v. active vision, which ensures that each detector obtains the maximum information from any position;
6. calibration sources, which may be placed on the body, within a body lumen, or near the camera;
7. 
11. the use of the calibration sources of (6) to obtain an attenuation map;
12. ultrasound-based, or MRI based attenuation correction (our 26137);
13. ultrasound-based attenuation correction using ultrasound patches, such as patch-sensor devices, described in U.S. Pat. Nos. 5,807,268; 5,913,829 and 5,885,222, all of which are assigned to MedAcoustics, Inc., Raleigh, N.C., USA, both for structural mapping, for correlating the structural map with the functional map, and for attenuation correction. The ultrasound patches may be incorporated with the radiopharmaceutical calibration sources;
14. minimal multiplexing between the detectors and the analyzer, to prevent saturation;
15. customizing to the patient imaging parameters such as overall camera configuration, angular travel of each sweep, sweeping speed, translational travel, angular and (or) translational steps, total imaging time, and the like.

The camera sensitivity may be determined by at least one of the following:

1. a sensitivity in terms of speed of data collection and spatial resolution, at least as good as a gold standard for PET imaging for at rest myocardial perfusion with N-13-ammonia ($NH_3$);
2. a sensitivity sufficient for reconstructing an image under a Cobalt wire Nema test of a line source of 5 mCi cobalt with a line spread function of less than 7 mm Full Width Half Maximum (FWHM) through air at a distance of at least 100 mm;
3. a sensitivity sufficient for resolving through air at a distance of at least 100 mm under a Nema Bar Phantom test of gaps formed between 1 mm wide led bars positioned less than 7 mm apart from one another over a uniform cobalt disc;
4. a sensitivity operative for image acquisition of a full organ in less than 10 seconds at a spatial resolution, capable of identifying objects not greater than about 7 mm×7 mm×7 mm with a signal-to-noise ratio of at least 4 to 1 or better;
5. a sensitivity for detecting at least 1 out of every 5000 emitted photons while allowing a reconstructions of a 3D image with a resolution of not more than 5 mm and energy resolution of not more than 15%; and
6. having a sensitivity to image a volume of about 5 cm diameter located about 150 mm from the detectors, with a total sensitivity of about 1 photons detected out of 65 emitted.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a simplified diagram showing a single detector detecting over a target region;

FIG. 2 is a simplified diagram showing two detector positions (not necessarily simultaneously) allowing three-dimensional information to be obtained from a target region, in accordance with some embodiments of the present invention;

FIGS. 3A-3D show a series of four time absorption characteristics for different radiopharmaceuticals within different tissues in accordance with some embodiments of the present invention;

FIG. 4 is a simplified schematic diagram showing a device for driving an imaging head and allowing control of the imaging head by the image analyzer device in accordance with some embodiments of the present invention;

FIG. 5 is a simplified flow chart illustrating the image analysis process carried out by the analyzer in FIG. 4 in the case of a single radiopharmaceutical in accordance with some embodiments of the present invention;

FIGS. 6A-6D illustrate two sets of successive images of the same target area taken using two different radiopharmaceuticals respectively, according to a preferred embodiment of the present invention in accordance with some embodiments of the present invention;

FIG. 7A is a simplified flow chart illustrating a procedure according to a preferred embodiment of the present invention using two or more radiopharmaceuticals for first, identifying an organ, and second determining the presence or otherwise of a pathology within that organ in accordance with some embodiments of the present invention;

FIG. 7B is a simplified flow chart showing a generalization of FIG. 7A for the general case of two specific patterns in accordance with some embodiments of the present invention;

FIG. 8 is a simplified flow chart illustrating a procedure according to a preferred embodiment of the present invention using two or more radiopharmaceuticals for identifying a region of low emissivity within a target area and using that identification to control imaging resources to better image the identified region in accordance with some embodiments of the present invention;

FIGS. 9A-9D illustrate two sets of successive images of the same target area taken using two different radiopharmaceuticals, in a similar way to that shown in FIG. 6, except that this time the regions of interest are one inside the other in accordance with some embodiments of the present invention;

FIGS. 10A-10J illustrate differential diagnosis effected by simultaneous imaging of at least two radiopharmaceuticals, in accordance with some embodiments of the present invention;

Figure 12:
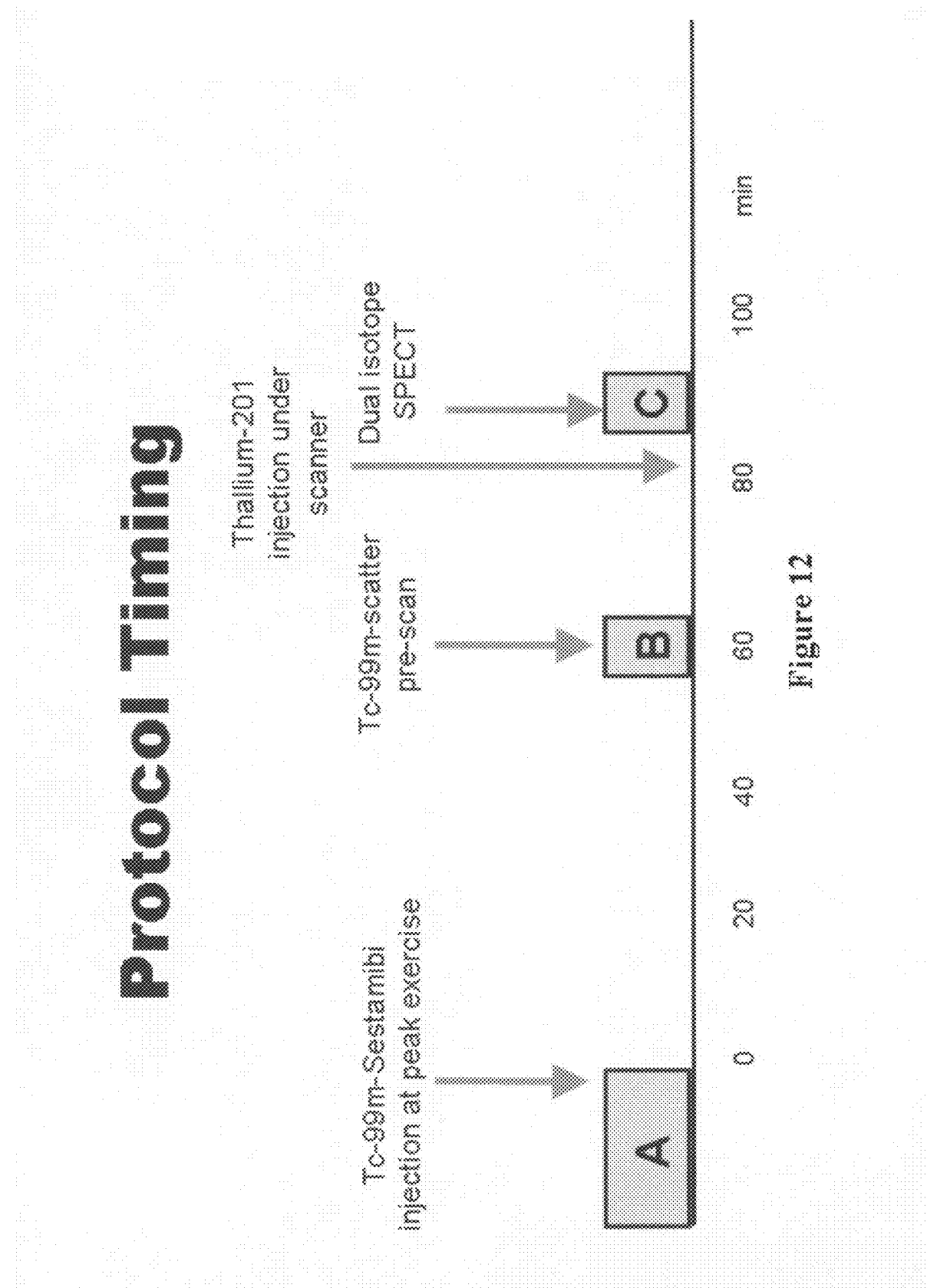
Figure 15:
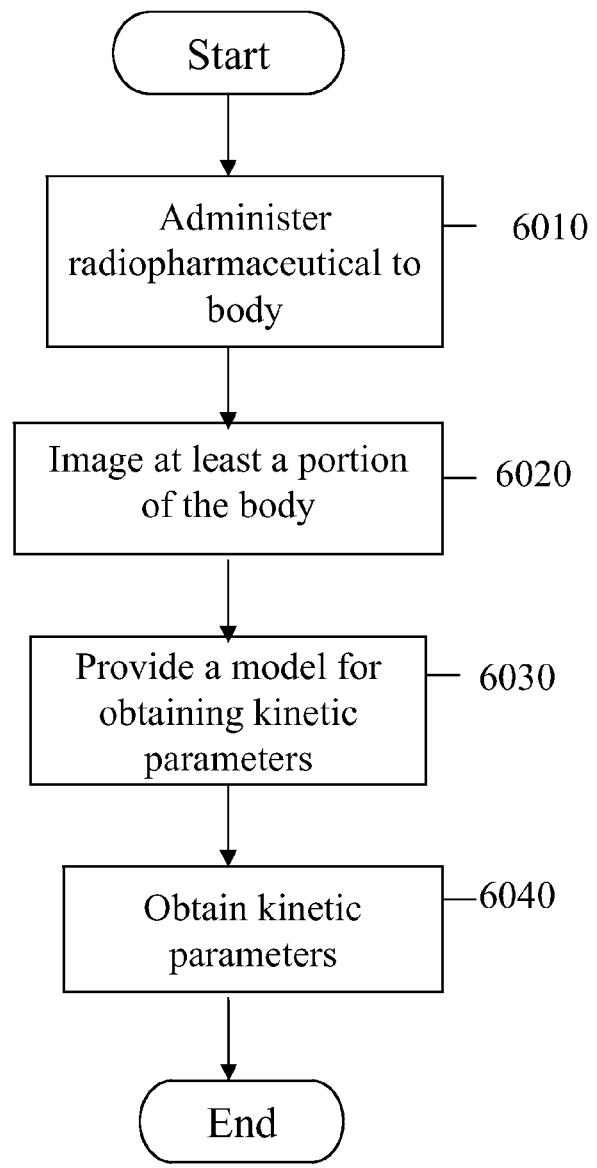
Figure 16:
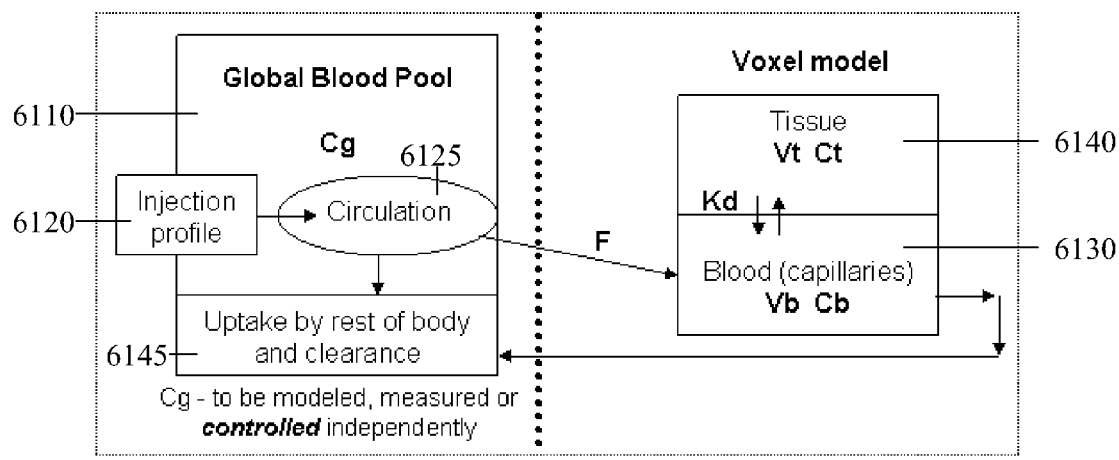
Figure 17:
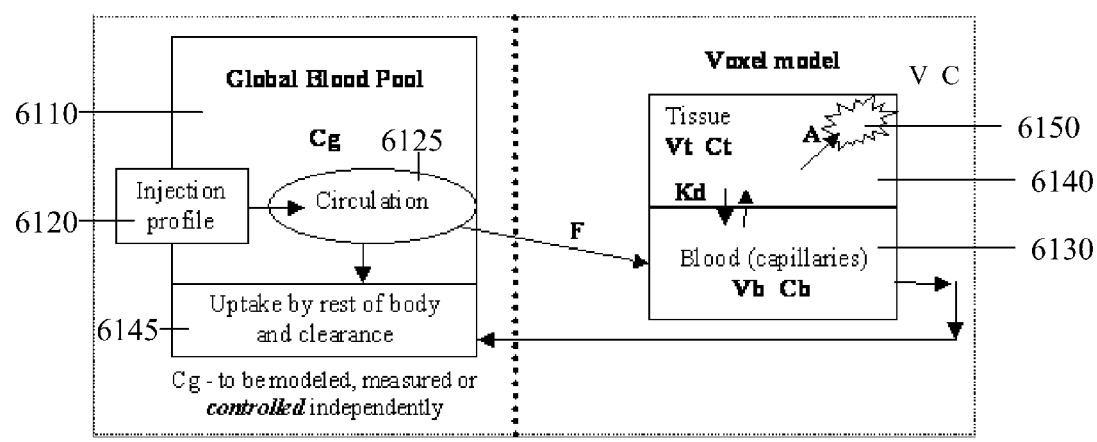
Figure 18:
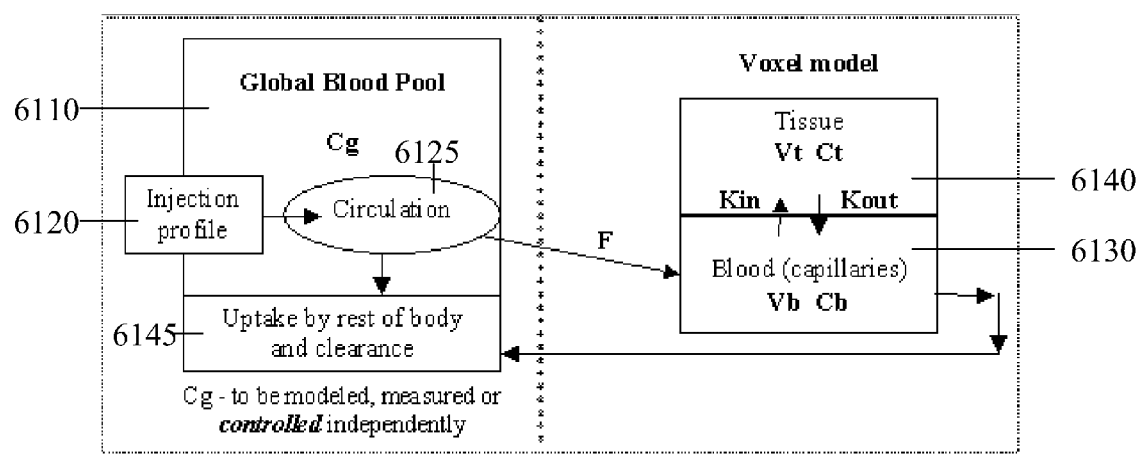
Figure 19:
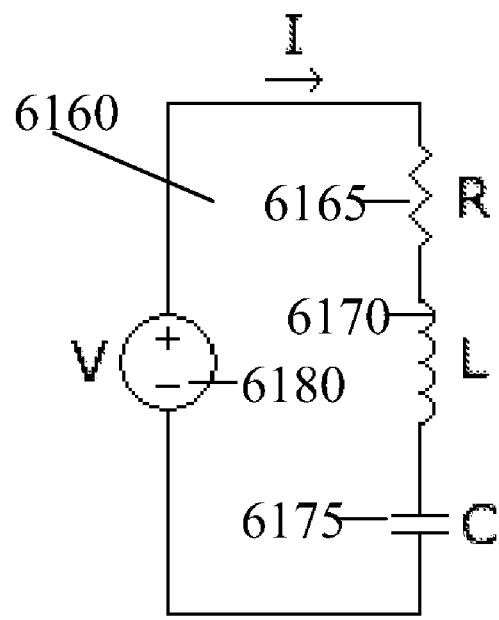
Figure 20:
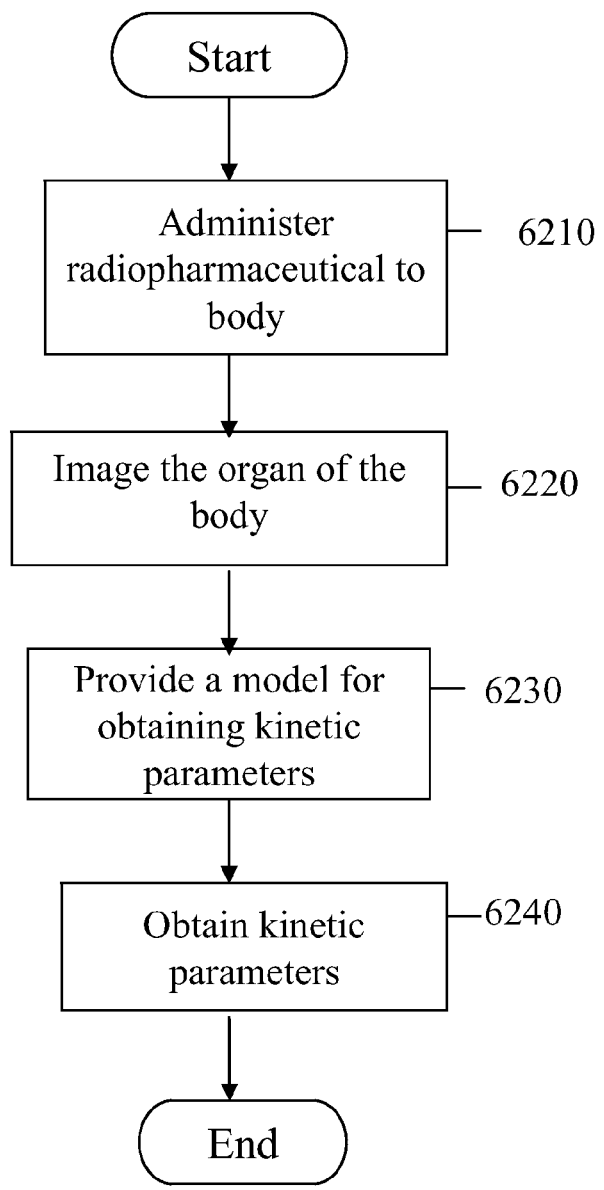
Figure 21:
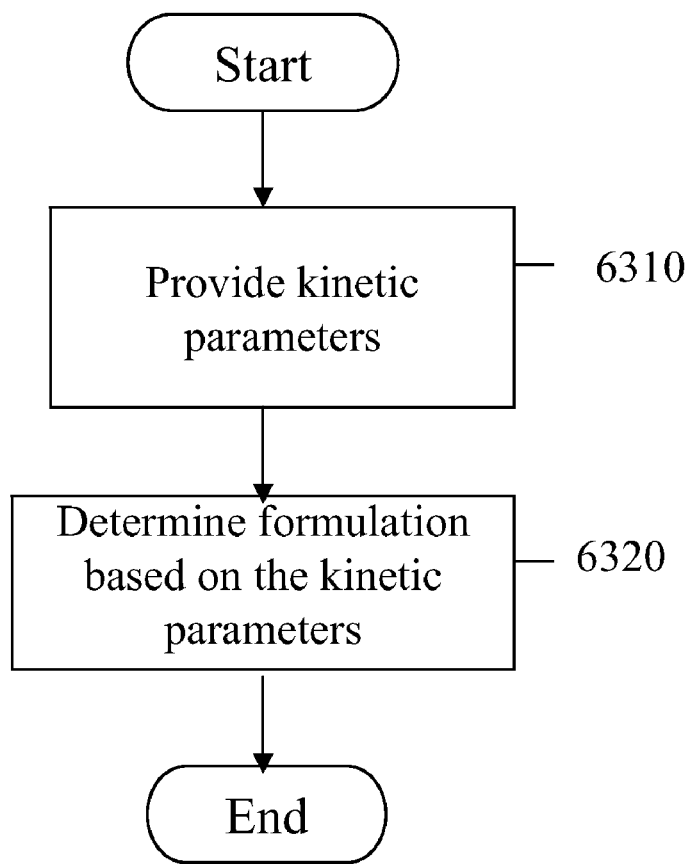
Figure 22:
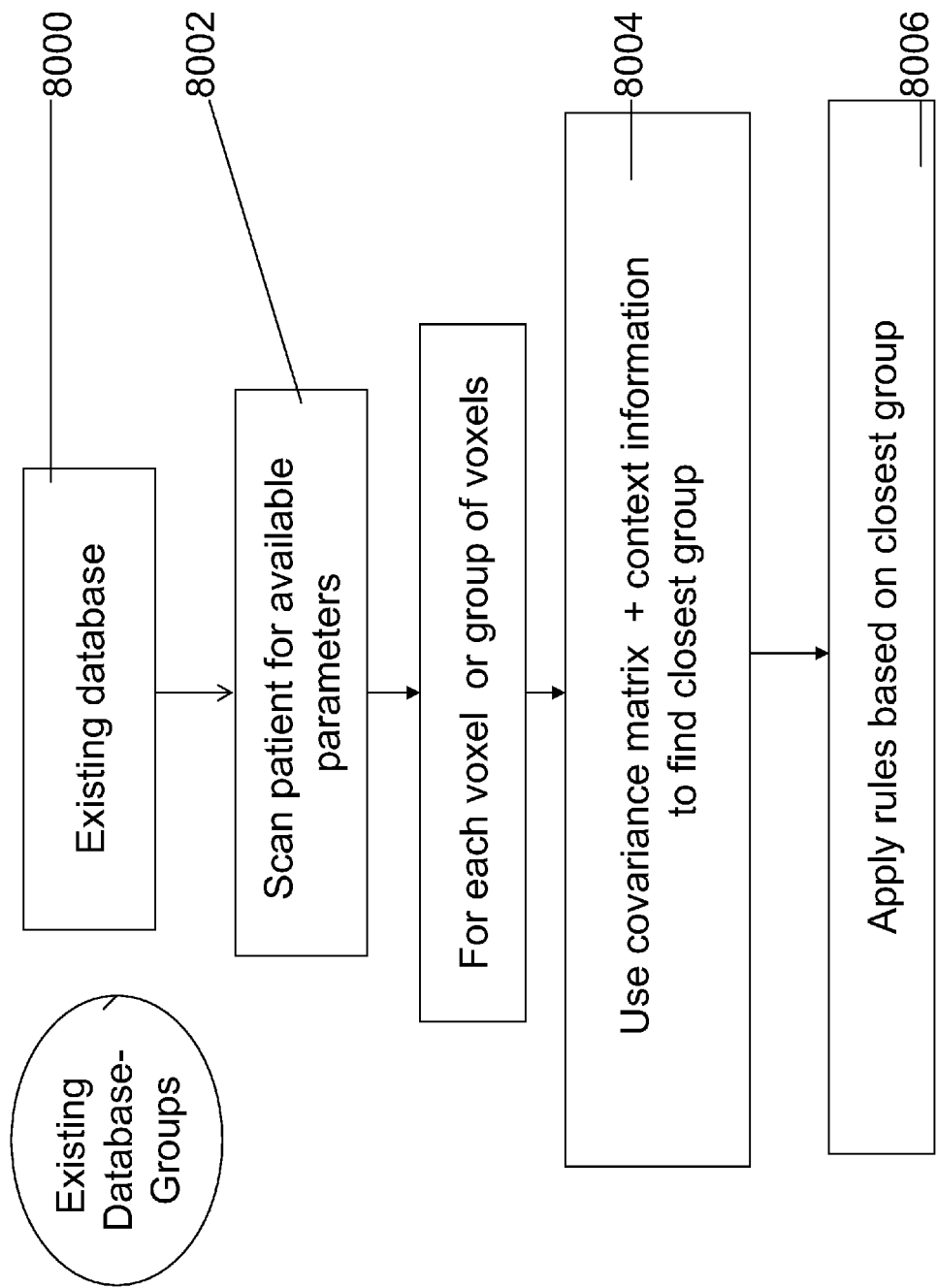
Figure 23:
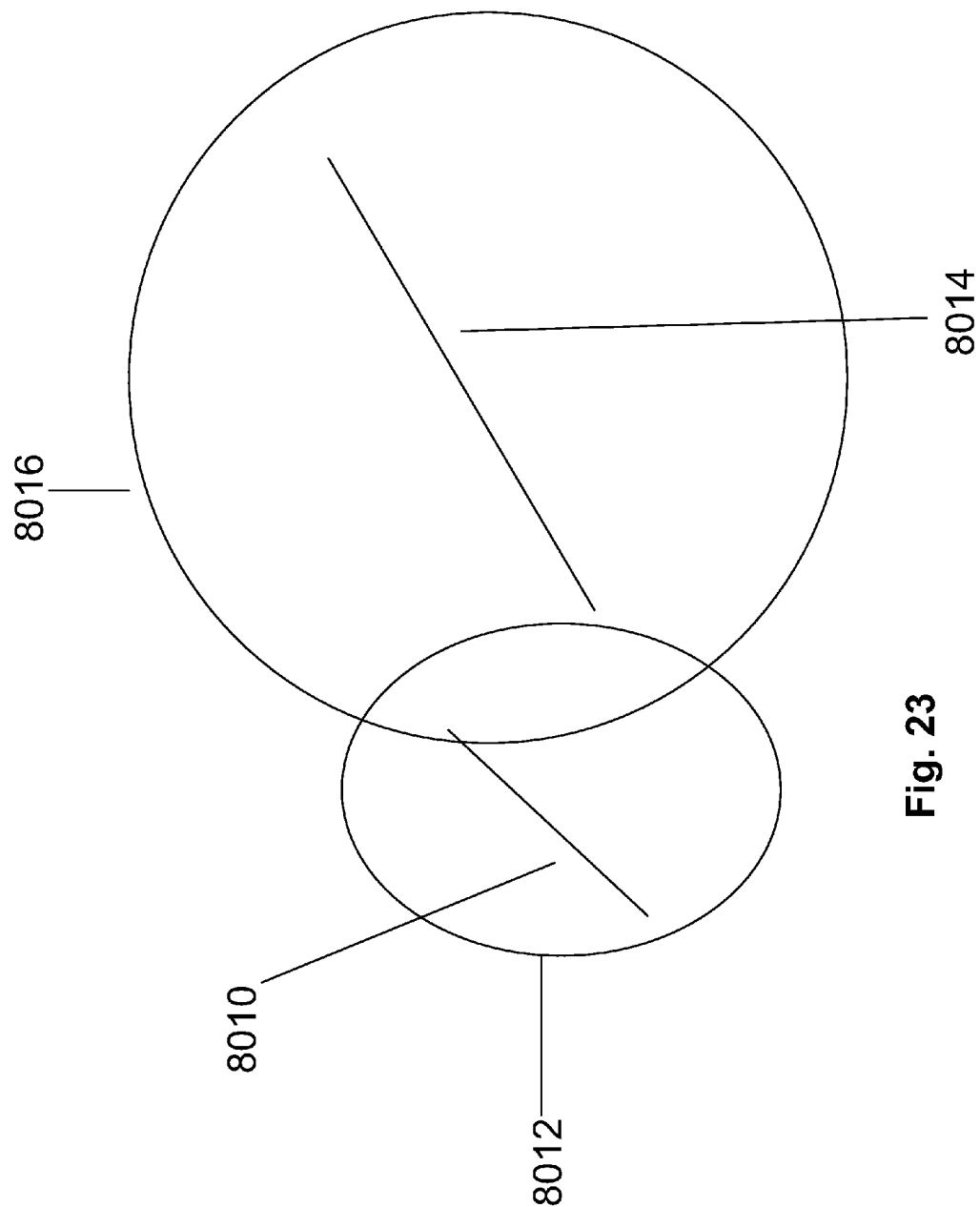
Figure 25B:
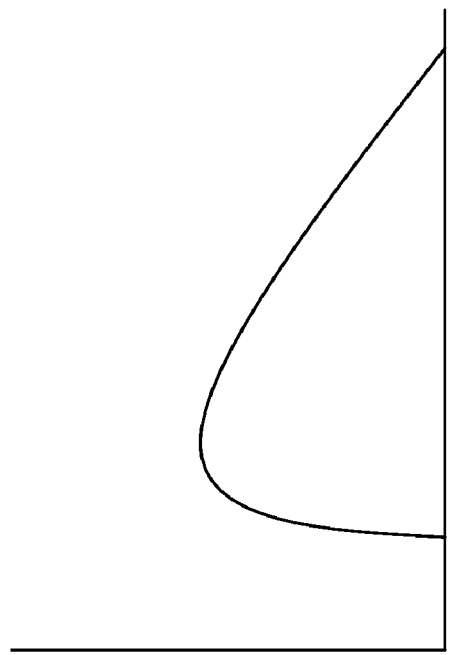
Figure 25A:
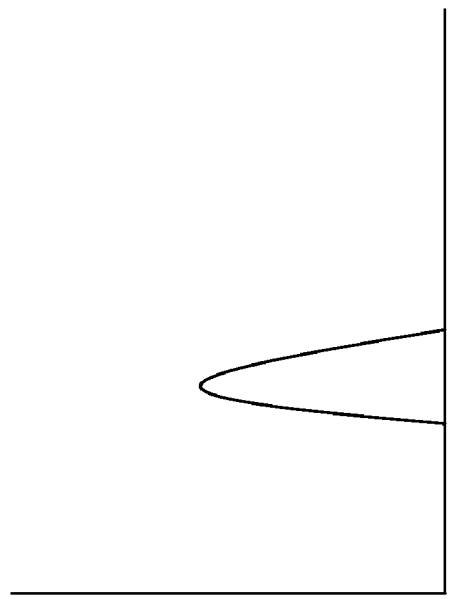
Figure 26:
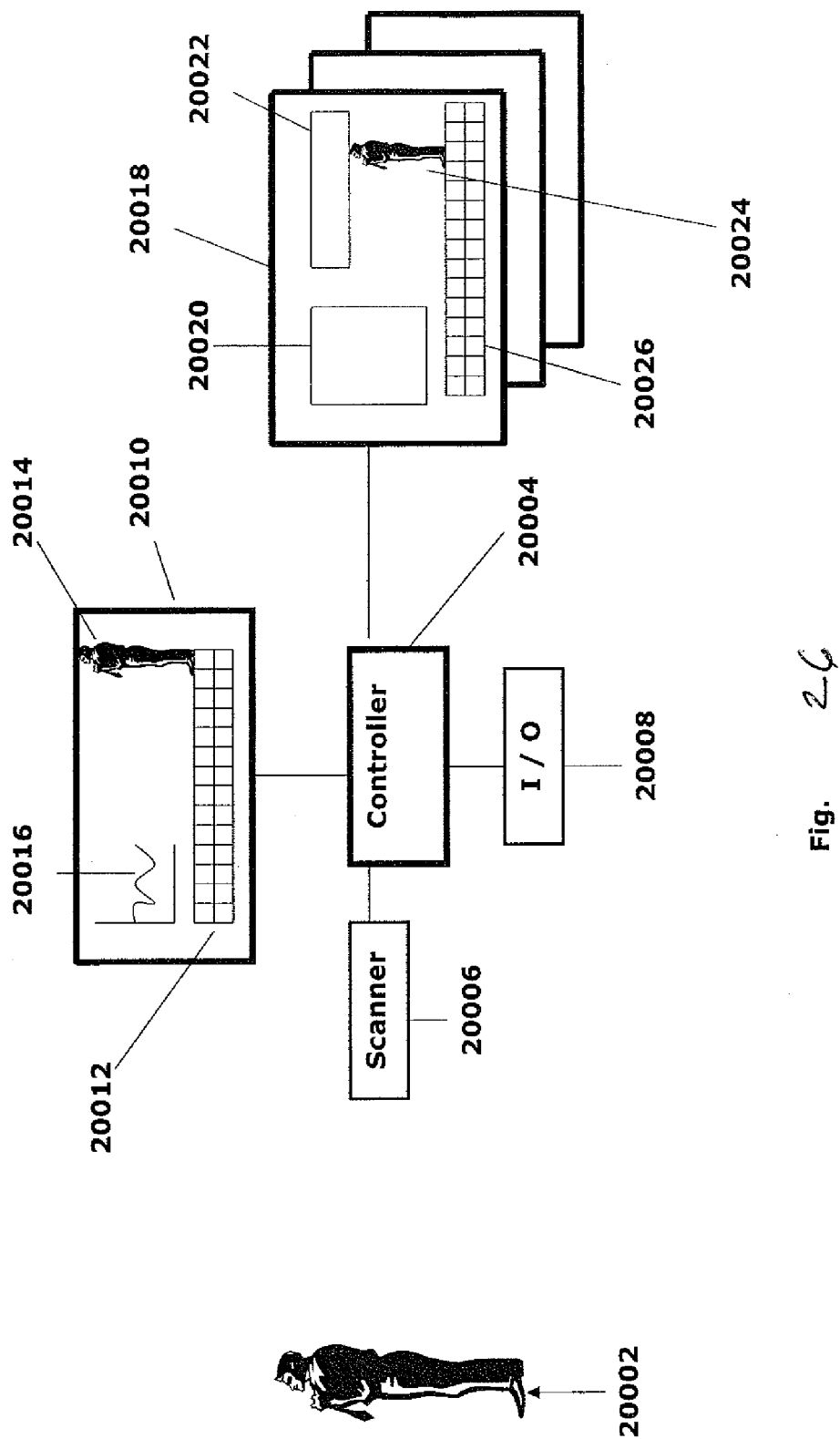
Figure 27:
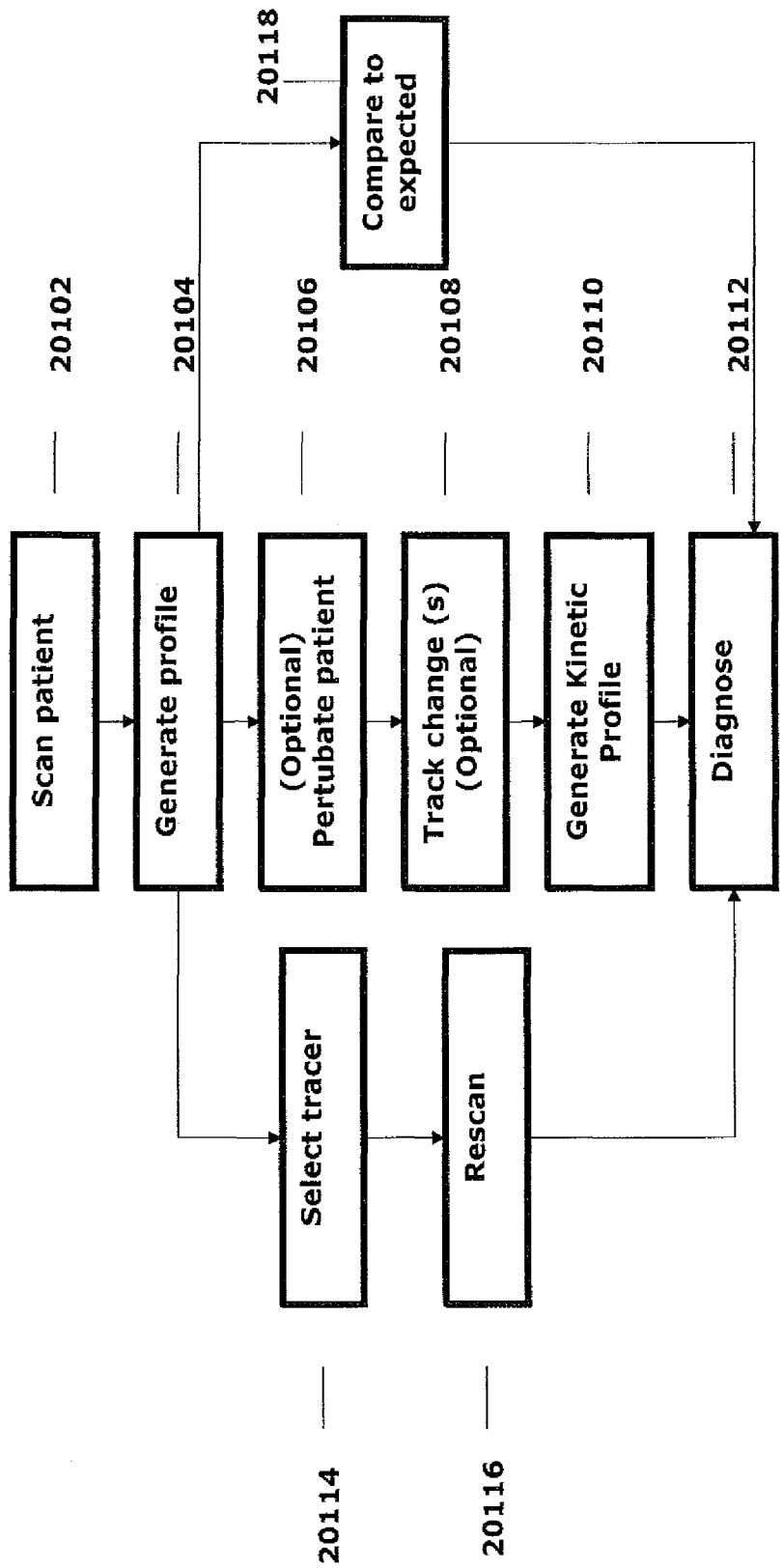
Figure 28:
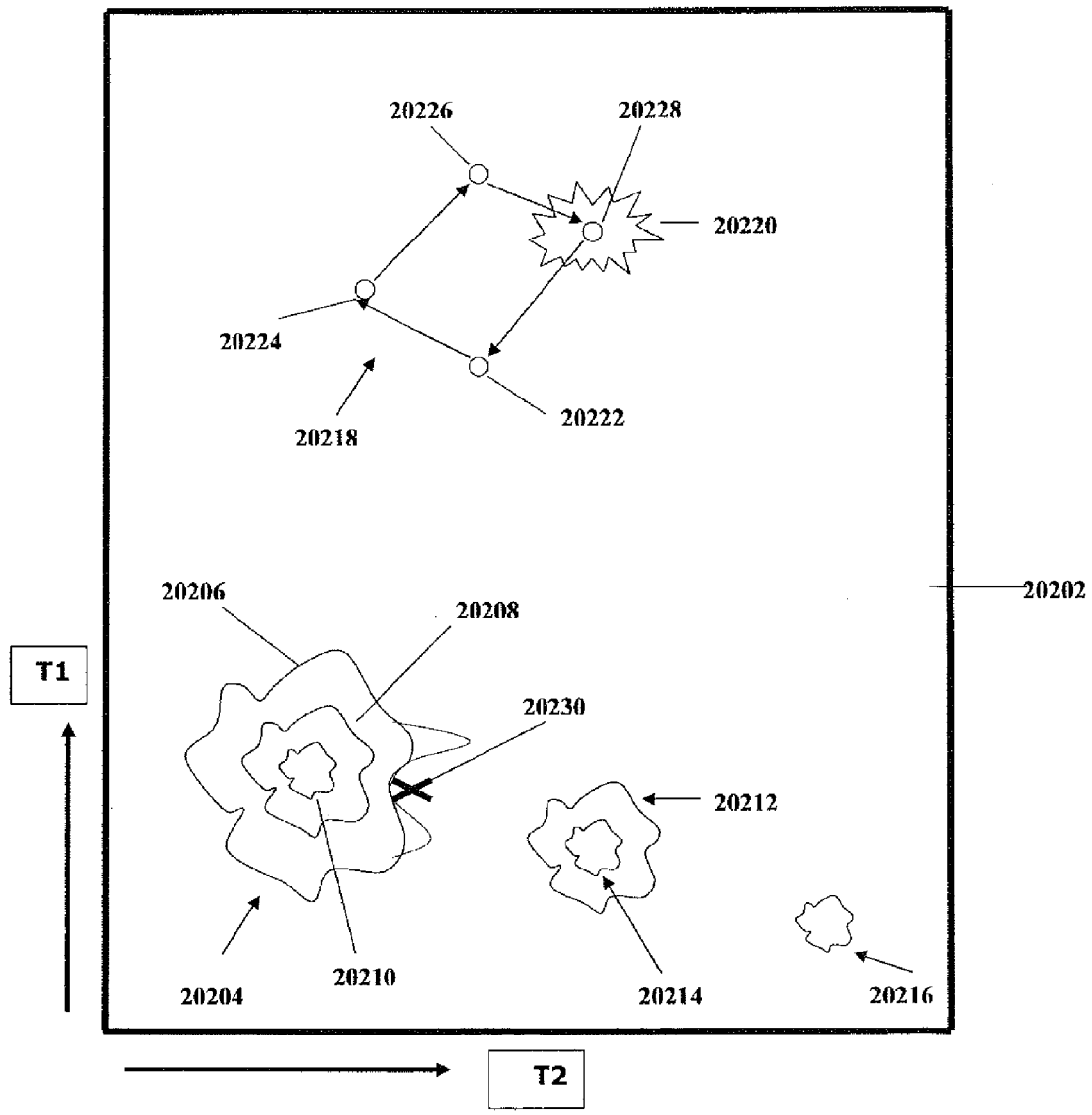
Figure 29:
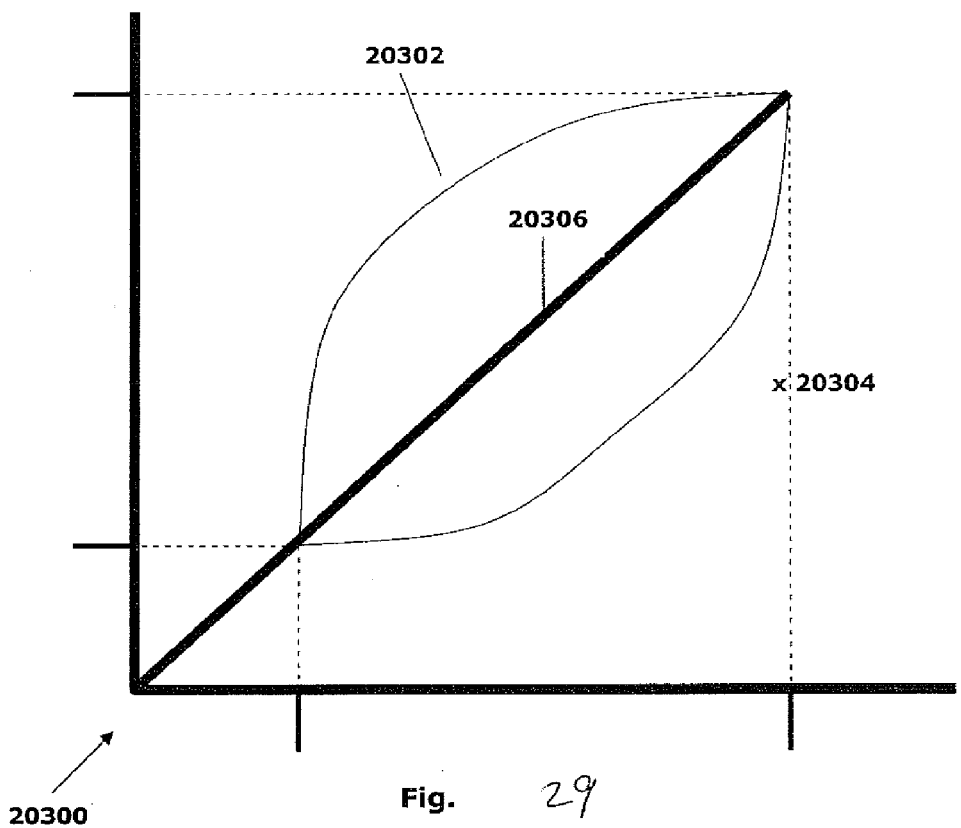

FIG. 11 is a flowchart for an imaging method of two isotopes, such as X1 and X2, having distinct gamma energies, for example, Y1 and Y2, respectively, in accordance with some embodiments of the present invention;

FIG. 12 schematically represents a time line for myocardial perfusion, in accordance with the present invention;

FIGS. 13A-13C are schematic representations of a Tc-99m photopeak, a Tl-201 photopeak, and Tc-99m cross talk contribution to at and around the Tl-201 main energy window, in accordance with the present invention;

FIGS. 14A-14E illustrate energy and angular relations in Compton Scatter, for treatment in accordance with embodiments of the present invention;

FIG. 15 is a simplified flowchart of a method for measuring kinetic parameters of a radiopharmaceutical in a body, according to a preferred embodiment of the present invention;

FIG. 16 is a schematic representation of a dynamic model of a voxel, according to a first preferred embodiment of the present invention;

FIG. 17 is a schematic representation of a dynamic model of a voxel, according to a second preferred embodiment of the present invention;

FIG. 18 is a schematic representation of a dynamic model of a voxel, according to a third preferred embodiment of the present invention;

FIG. 19 is an example of RLC circuit analysis, according to a preferred embodiment of the present invention;

FIG. 20 is a simplified flowchart of a method for measuring kinetic parameters of a radiopharmaceutical in an organ of a body, according to a preferred embodiment of the present invention;

FIG. 21 is a simplified flowchart of a process for obtaining the drug formulation, according to a preferred embodiment of the present invention;

FIG. 22 is a simplified flow chart, illustrating a process for imaging a patient using multiple kinetic parameters and measuring the distance between respective kinetic parameters, to relate the patient or individual voxels or groups of voxels to existing groups, thereby to arrive at a decision, regarding the patient or individual voxels or groups of voxels, according to the present invention;

FIG. 23 illustrates dynamic behavior of a parameter;

FIGS. 24A-24D illustrate different behaviors over time of different kinetic parameters;

FIG. 25A illustrates dynamic behavior of an absorption parameter with a dead or diseased membrane;

FIG. 25B illustrates the dynamic behavior of the same parameter with a healthy membrane;

FIG. 26 is a schematic diagram of a configuration for acquiring and/or using multi-parametric information, in accordance with an exemplary embodiment of the invention;

FIG. 27 is a flowchart of a method of acquiring and/or using multi-parametric information, in accordance with an exemplary embodiment of the invention;

FIG. 28 is a simplified space indicating a diagnosis and a normal physiological state, in accordance with an exemplary embodiment of the invention;

FIG. 29 shows a simplified two dimensional space showing a complex diagnosis, in accordance with an exemplary embodiment of the invention;

FIGS. 30-38 are radiopharmaceutical protocols, in accordance with the present invention.

DESCRIPTION OF THE PREFERRED EMBODIMENTS

The present invention relates to the capabilities of a highly sensitive radioactive-emission camera, a result of a meticulous search for the many different effects that combine synergistically to increase sensitivity and spatial, spectral, and time resolutions. The new camera opens a new realm in SPECT-type imaging, making it viable for dynamic studies, the use of radiopharmaceutical cocktails, molecular imaging, dosimetry and other studies requiring the high sensitivity and resolutions. In particular, the new camera opens the door to SPECT expert system, examples for which are provided.

The expert system relates to defining disease signatures for automatic diagnosis, preferably, based on a multi-parameter vector, preferably, based on kinetic radiopharmaceutical values. Additionally or alternatively, based on simultaneous administration of multiple isotopes.

Dynamic imaging provides a plurality of kinetic parameters, per voxel, allowing one to define pathological signatures, each characterized by a unique combination of the plurality of parameters, so that a single imaging session may clearly identify a pathology by its unique pathological signature—the unique combination of the plurality of parameters that characterizes it, as an expert-system type of diagnosis.

Radiopharmaceutical cocktails, together with high-definition spectral imaging, for example, with an energy window between about ±15 and ±5%, similarly results in a plurality of radiopharmaceutical related parameters, which can be used to define pathological signatures, again leading to an expert-system type of diagnosis.

Molecular imaging, which is defined as the capability to image 1E-10 Moles in 1 gram of tissue, may be used for investigating the biology of cellular molecular events involved in normal and pathologic processes in vivo to better understand these processes. For example, molecular imaging may determine the level of gene expression (by targeting mRNA), or the level of protein expression.

Dosimetry is a study for determining a future administration dose, for example by:
i. administering a radiopharmaceutical in an extremely low dose;
ii. measuring the distribution of the radiopharmaceutical in the body; and
iii. determining the preferred administration dose of the radiopharmaceutical agent for at least one future administration.

The at least one future administration may be used for imaging or for therapeutic purposes, for example, using the same agent but with a therapeutic compound in place of the labeling isotope. The second administration takes into account toxicity, radiation dose, clearance rate, uptake rate by an organ, or any other measurements, as provided by the first administration, to weigh benefit and potential harm.

The effects, which were combined to increase the camera's sensitivity and resolutions, are as follows:
1. solid collection angles greater than 0.1 or 0.15 steradians;
2. close proximity of the detectors to the body, in order to increase both:
  i. detection efficiency, which falls as a proportionally to the square of the distance from an object; and
  ii. resolution, where the number of detector pixels which view an object also falls proportionally to the square of the distance from the object;
3. windshield-wiper sweeping motions, with a center of rotation outside the patient's body, to maximize the information obtained from each x;y;z detector position;
4. trio-vision of each voxel, wherein each voxel is viewed with x, y, and z, components, as opposed to stereo vision in a plane, with only x and y components of state-of-the-art cameras;
5. Focus on a region of interest, by:
  i. prescanning;
  ii. independent motion of detectors, for independent focusing on ROI, by each detector;
  iii. applying algorithm which select a preferred set of views to for ROI focusing, based on the geometry of the organ to be imaged;
  iv. zooming in, by a second algorithm tic iteration, to select a preferred set of views based on earlier findings;
  v. active vision, which ensures that each detector obtains the maximum information from any position;
6. calibration sources, which may be placed on the body, within a body lumen, or near the camera;
11. the use of the calibration sources of (6) to obtain an attenuation map;
12. ultrasound-based, or MRI based attenuation correction (our 26137);
13. ultrasound-based attenuation correction using ultrasound patches, such as patch-sensor devices, described in U.S. Pat. Nos. 5,807,268; 5,913,829 and 5,885,222, all of which are assigned to MedAcoustics, Inc., Raleigh, N.C., USA, both for structural mapping, for correlating the structural map with the functional map, and for attenuation correction. The ultrasound patches may be incorporated with the radiopharmaceutical calibration sources;
14. minimal multiplexing between the detectors and the analyzer, to prevent saturation;
15. customizing to the patient imaging parameters such as overall camera configuration, angular travel of each sweep, sweeping speed, translational travel, angular and (or) translational steps, total imaging time, and the like.

The camera sensitivity may be determined by at least one of the following:
1. a sensitivity in terms of speed of data collection and spatial resolution, at least as good as a gold standard for PET imaging for at rest myocardial perfusion with N-13-ammonia ($NH_3$);
2. a sensitivity sufficient for reconstructing an image under a Cobalt wire Nema test of a line source of 5 mCi cobalt with a line spread function of less than 7 mm Full Width Half Maximum (FWHM) through air at a distance of at least 100 mm;
3. a sensitivity sufficient for resolving through air at a distance of at least 100 mm under a Nema Bar Phantom test of gaps formed between 1 mm wide led bars positioned less than 7 mm apart from one another over a uniform cobalt disc;
4. a sensitivity operative for image acquisition of a full organ in less than 10 seconds at a spatial resolution, capable of identifying objects not greater than about 7 mm×7 mm×7 mm with a signal-to-noise ratio of at least 4 to 1 or better;
5. a sensitivity for detecting at least 1 out of every 5000 emitted photons while allowing a reconstructions of a 3D image with a resolution of not more than 5 mm and energy resolution of not more than 15%; and
6. having a sensitivity to image a volume of about 5 cm diameter located about 150 mm from the detectors, with a total sensitivity of about 1 photons detected out of 65 emitted.

Multi-Dimensional Analysis

The present embodiments comprise an apparatus and a method for radiation based imaging of a non-homogenous target area having regions of different material or tissue type or pathology. The imaging uses multi-dimensional data of the target area in order to distinguish the different regions. Typically the multi-dimensional data involves time as one of the dimensions. A radiopharmaceutical has particular time-absorption characteristics which are specific for the different tissues, and the imaging device is programmed to constrain its imaging to a particular characteristic.

The result is not merely an image which concentrates on the tissue of interest but also, because it is constrained to the tissue of interest, is able to concentrate imaging resources on that tissue and thus produce a higher resolution image than the prior art systems which are completely tissue blind.

The principles and operation of a radiological imaging system according to the present invention may be better understood with reference to the drawings and accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 1:
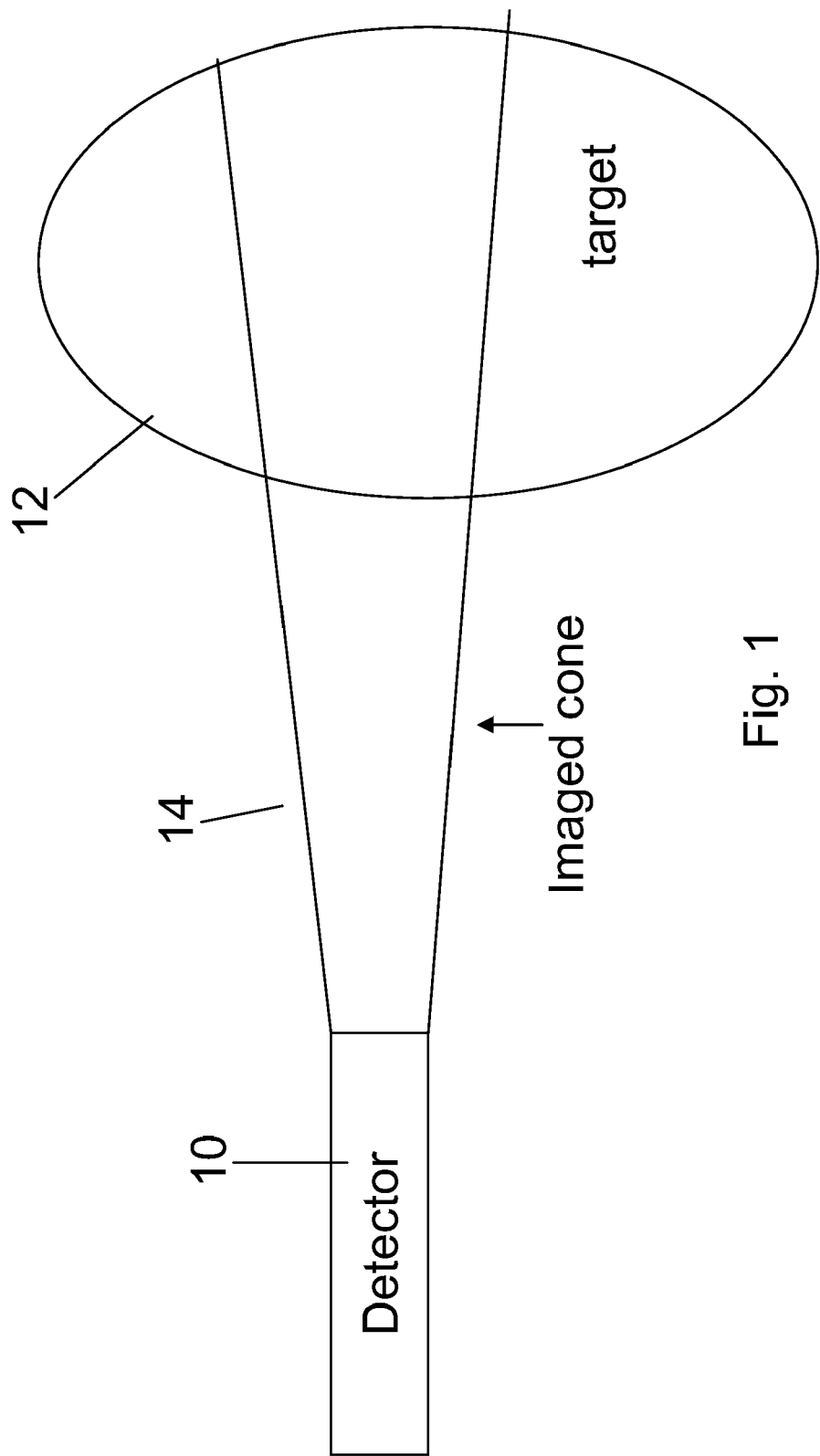

Reference is now made to FIG. 1, which illustrates a simple Geiger counter taking an image of a target according to the prior art. Geiger counter 10 is placed in association with target 12 and absorbs any radioactive particles that come its way. In general the radioactive particles arriving at the Geiger counter arrive from somewhere within cone 14. The Geiger counter has no information as to the depth from which the particle comes and cannot even distinguish between particles arriving from different directions within the cone. Thus in principle the prior art Geiger counter gives low resolution one dimensional information.

If the counter is now moved to different positions over the surface of the target then the data from the different positions can be built up into a low resolution two-dimensional image.

One way of increasing the resolution of the Geiger counter is to make it smaller. Then the cone, whilst retaining the same geometry, gives higher resolution data.

The detector takes $(y_t)_{t=1}^T$ samples to form a data set, which would typically be a two-dimensional image of the target from a given direction.

Figure 2:
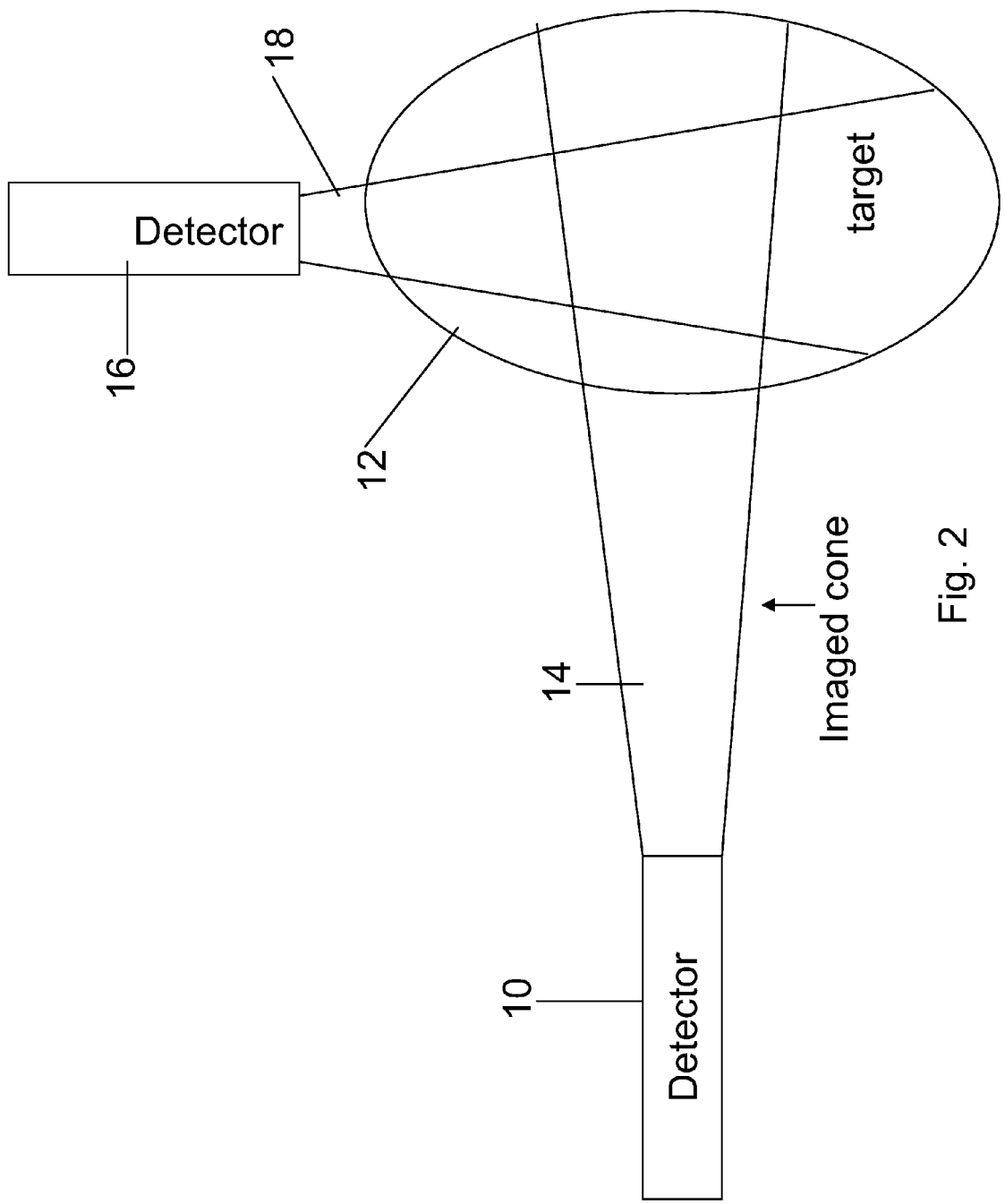

Reference is now made to FIG. 2, which is a simplified diagram showing how three-dimensional information can be obtained from the target. Parts that are the same as in previous figures are given the same reference numerals and are not referred to again except as necessary for understanding the present embodiment. A second Geiger counter 16 is placed essentially at right angles to the first Geiger counter and obtains a similar kind of image to the first Geiger counter. However, since the two cones overlap, the images produced can be cross-correlated to infer the presence of hot or cold radiation sources in three dimensions.

Reference is now made to FIG. 3, which is a sequence of graphs illustrating the different absorption characteristics for different tissues of a given radiopharmaceutical. Typical radiopharmaceuticals that may be considered are Thallium 201 and Technetium 99. FIG. 3a indicates a typical absorption characteristic of thallium 201 for blood, thallium 201 being a particularly good radiopharmaceutical for blood. The radiopharmaceutical is generally absorbed by the blood fairly rapidly following digestion and then gradually disappears as it is taken up by the various tissues and organs including the kidneys. Radiopharmaceutical material from the tissues eventually finds its way back into the blood for excretion. That which is absorbed by the kidneys is excreted directly and not seen again.

Figure 3A:
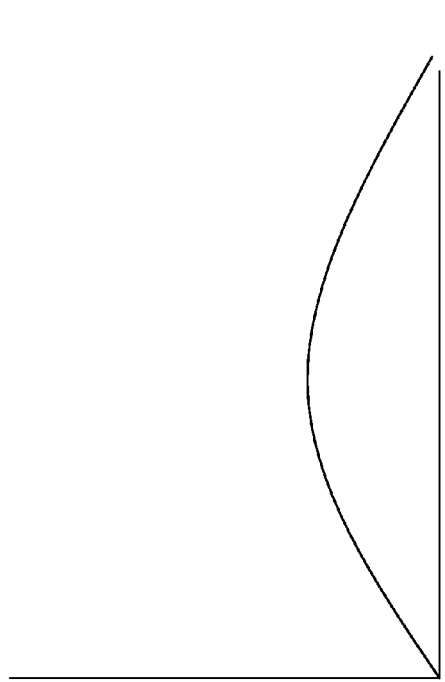
Figure 3B:
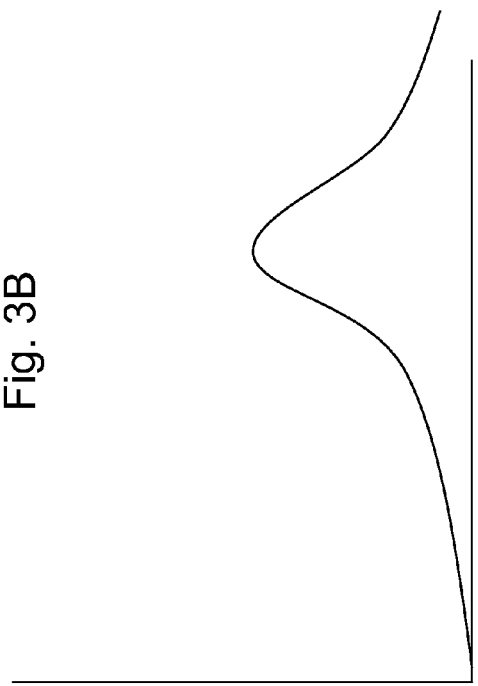
Figure 3C:
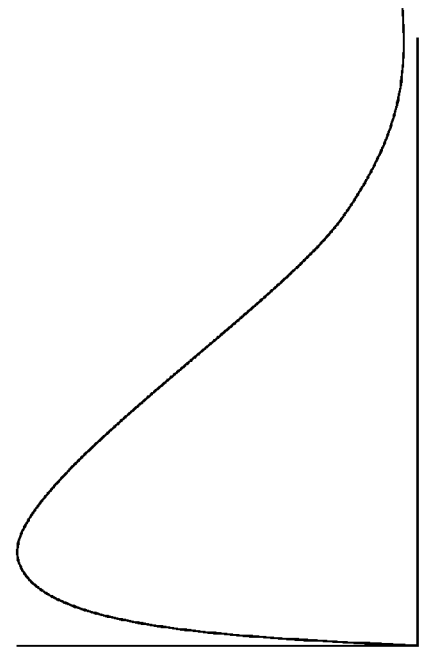
Figure 3D:
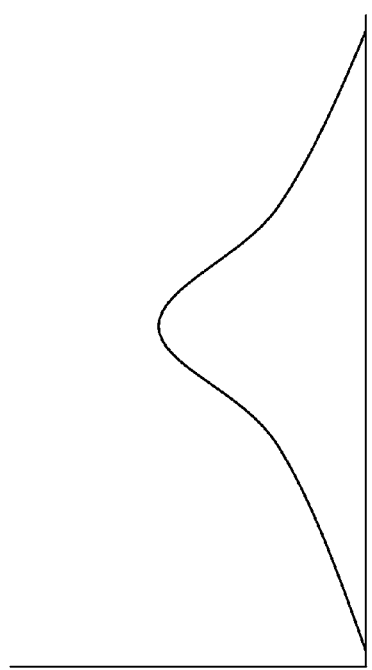

FIGS. 3B, 3C and 3D show time absorption characteristics for technetium 99 for different tissues, and it will be seen that the characteristic is generally curved but peaks at different times for the different tissues.

The principle on which the present embodiments are based is as follows: Considering the graphs in FIG. 3, it will be apparent that a region belonging to a single tissue will behave in a uniform manner as regards signal intensity. That is to say, a given radiopharmaceutical will be taken up and then expelled at the same rate over a given tissue, whereas this rate will be different for other tissues. If therefore a series of successive images are taken of the target and the images are analyzed region by region for rates of change of intensity, a particular desired region can be identified by virtue of having rates of change in intensity that fit with a given characteristic. The regions are distinguishable in this way even if the region of interest is heavily overlapped with other regions.

Figure 4:
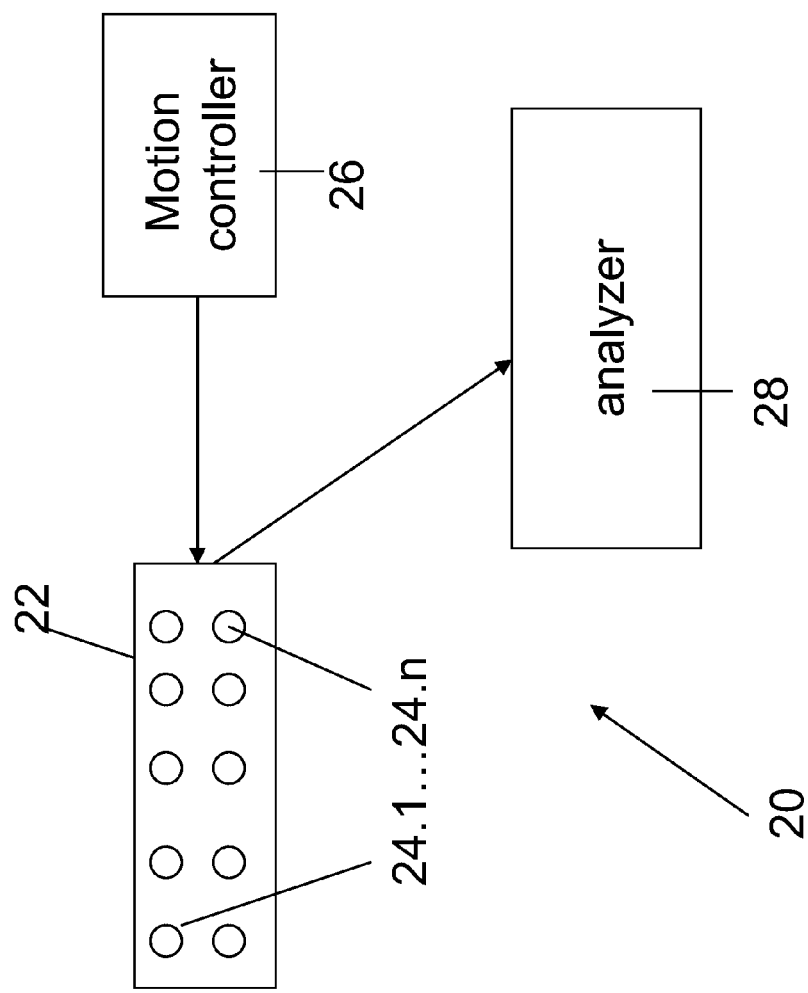

Reference is now made to FIG. 4, which shows apparatus for radiation-based imaging of a non-homogenous target area. Apparatus 20 comprises an imaging unit 22 which itself consists of a series of small Geiger counters 24.1 . . . 24.n arranged on an imaging head. The imaging unit is controlled by motion controller 26 to take readings from different locations around the target area. Preferably, the motion of the imaging head is controlled by software via servo-motors. In addition the motions, either of the individual Geiger counters or of groupings of the Geiger counters, are also controlled by software via servo-motors.

In a preferred embodiment, the signals received from the individual Geiger counters are summed to form a three-dimensional image of the target area. The skilled person will appreciate that the system could also be based on a two-dimensional image. In either case, the signals are fed to an image analyzer 28, where the signals are analyzed to form images.

In the preferred embodiments, the image analyzer is able to use the radiopharmaceutical take up characteristics to compare successive images and identify regions of particular interest, and then to concentrate imaging resources on those regions. That is to say the image analyzer is in fact able to control further operation of the imager.

Figure 5:
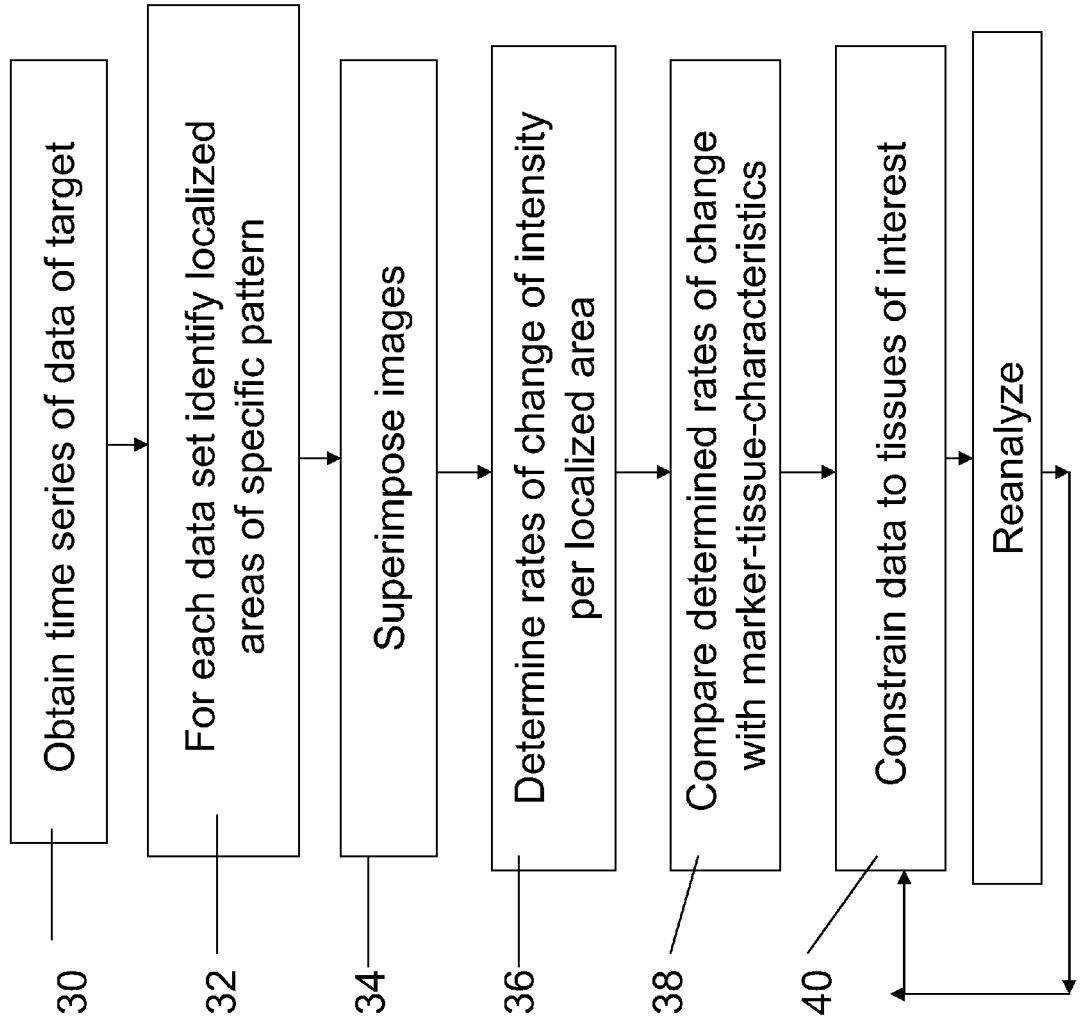

Reference is now made to FIG. 5, which is a simplified flow chart illustrating the image-analysis process carried out by analyzer 28 in the case of a single radiopharmaceutical. Preferably a series of images of the same views are taken at different times, stage 30, and a three-dimensional overall image of the target is formed for each time. The analyzer then analyzes each of the three-dimensional overall images for local intensities at different locations around the target, stage 32. The local intensities are noted and the same locations on the different images are superimposed in stage 34. From the superpositioning, local rates of change of intensity between the images may be obtained in stage 36. The rates of change are compared with the pre-obtained characteristics for the radiopharmaceutical with the different tissues in stage 38, and the data are then constrained to those localities which conform to the desired predetermined characteristics in stage 40. As a result the imaging process can be used to identify and concentrate on localities of interest and data from other localities can be jettisoned. Consequently, the image analysis is able to concentrate its resources on the tissues of interest and a higher resolution final image can be produced.

It will be appreciated that in many cases two types of tissue may be superimposed, of which only one of the tissues is of interest. In this case it is of equal importance both to exclude the one tissue that is not of interest and to include the tissue that is of interest. It may be that the best radiopharmaceutical for one tissue may not be the best radiopharmaceutical for the other tissue. The system as described with respect to FIGS. 4 and 5 may be adapted to use with two or more radiopharmaceuticals, as exemplified in FIG. 6. Each radiopharmaceutical produces a radioactive particle of different energy level, and therefore the data from the different radiopharmaceuticals can be collected and summed separately to form different images. Mathematically the different data sets obtained from the different energy level signals may be treated as different dimensions of a multi-dimensional vector. For each of the radiopharmaceutical-images the appropriate characteristics are used to identify the tissues of interest, and the results can be cross-checked between the different radiopharmaceuticals. The different tissues can be mapped and the image analysis can concentrate on the area of interest. As a result the system uses both time and particle energy as separate dimensions in addition to the spatial dimensions in order to characterize or map the tissues.

As a result the image analysis unit is able to produce a final result treating the various tissue regions as separate entities. Furthermore, as the system is aware of the regions as entities it is able to further direct the imaging process to concentrate on the regions of interest.

An example in which regions at least partially overlap is the heart. Generally, scans of the heart are interested in the muscular walls of the heart. Although the chambers of the heart are filled with blood, any signal coming from the blood is in fact noise to this kind of scan. It is therefore advantageous to carry out an imaging process which is able to positively identify signals from the muscular heart walls and at the same time exclude the blood.

Referring now to FIG. 6, and in a preferred embodiment, the patient ingests two radiopharmaceuticals, thallium 201 and technetium 99. The first of these is an effective blood radiopharmaceutical and two successive thallium images are shown in FIGS. 6a and 6b, and the second is more effective at marking muscle tissue and two successive images thereof are shown in FIGS. 6c and 6d. The heart is imaged at intervals chosen both for the characteristic for thallium 201 in blood and for the characteristic of technetium 99 in muscle. The result is a series of images for each of the radiopharmaceuticals. The series for thallium 201 may be constrained to show the regions of blood quite clearly, and to filter out other regions. In here a blood vessel is shown clearly in 6a and more faintly in 6b where the thallium has mostly been flushed out. The series for technetium 99, FIGS. 6c and 6d show muscle wall structures. The first of the two images apparently shows larger structures but in fact all that it is showing is that much technetium has not yet been absorbed in the muscle. The second image 6d may therefore be used to constrain the first image 6c to show only the muscle walls regions. The two series of images may then be superimposed to filter out from the technetium 99 images 6c and 6d anything that appears strongly in the thallium images 6a and 6b. The filtering may additionally remove anything that appears strongly in both images as coming from outside the region.

In the above example, two regions were of respectively positive and negative interest, meaning one for concentrating on and the other for filtering out. It will be appreciated that several regions or several tissue types may be of positive interest or there may be any combination of regions with just one being of positive interest. Alternatively all regions may be of positive interest but importance may be attached to discriminating between the different signals from the different regions.

The system is able to use the mapping to generate an image comprising the different tissue regions as distinct entities. As a consequence of the mapping process, the system is able to be aware electronically of the different regions and thus control both the imaging head and the analysis unit to concentrate their resources on specific regions. The result is greater resolution for the regions of interest.

The preferred embodiments may be used to expand the information obtained from the radiopharmaceuticals, using either or both of examining the kinetics of the radiopharmaceuticals over time and using several radiopharmaceuticals concurrently.

In order to increase the specificity of the test, additional second substances ("secondary substances"), with reactivity and pharmaco-kinetics differing from those of the first substance can be used in order to enhance the differentiation between the different pathologies, as explained above with respect to FIG. 6. The secondary substance, in this case thallium, ideally marks only a subset of the population marked by the primary substance and does so at different rates. Such a difference exists because of different affinity to various cell types and different participation in metabolic reactions of different tissues. The difference is associated with the rate of marking and/or with the location of the marking.

Upon reading the radioactive signals emanating from the voxels stemming from different substances at different time instances, it is possible to build for every voxel a multi dimensional data matrix $S_{jk}$ whose elements are intensity readings taken at instances K resulting from the interaction of Substance J. Examination of every voxel of tissue in this multi-dimensional space quantifies the temporal and specific reaction of the tissue to different substances and thus increases the probability of specific detection of different pathologies. Furthermore, standard image processing techniques can be used in order to more accurately define the spatial location of different pathologies.

In addition to the method above, spatial properties that reflect typical relationships between neighboring voxels may also be a criteria and represented as part of the pattern of the tissue type.

Figure 7A:
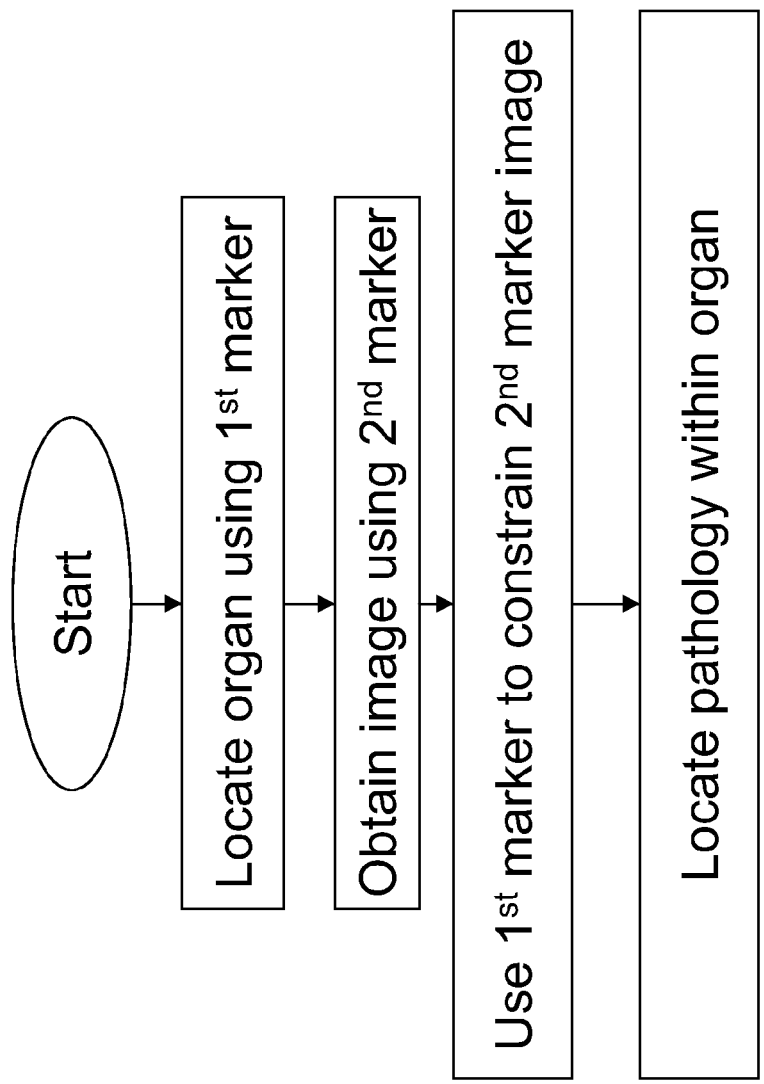
Figure 7B:
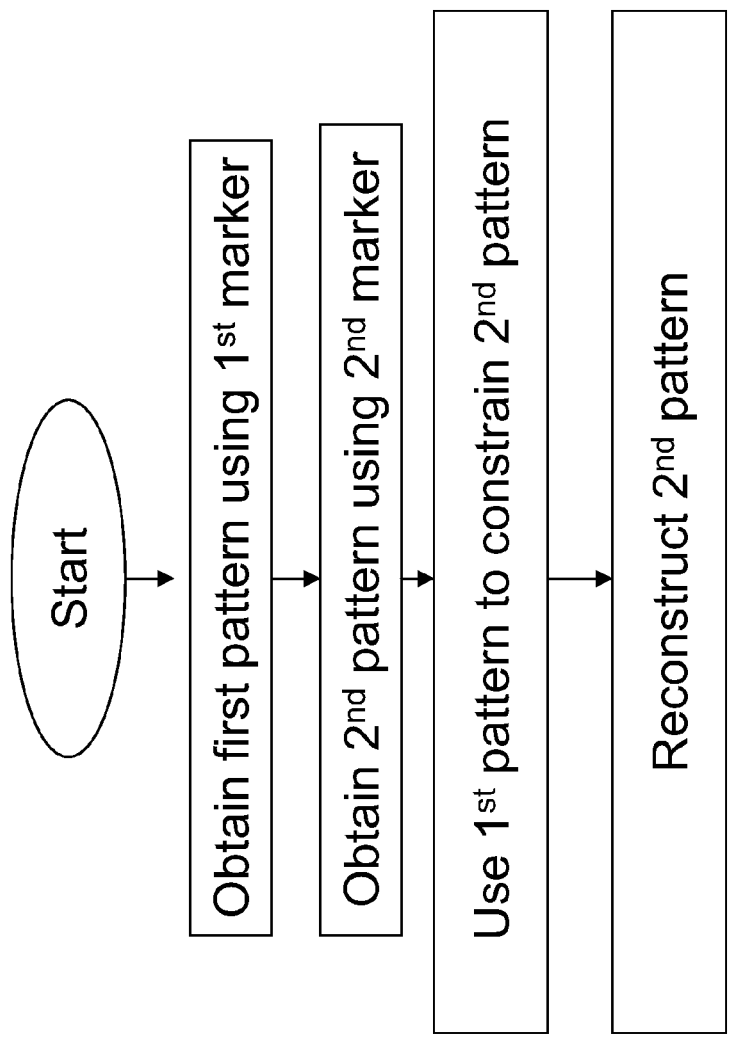

Reference is now made to FIG. 7, which illustrates an additional statistical approach. In FIG. 7, an automatic algorithm based on expected intensities may be used to determine if the entire organ or region is diseased or non-diseased. Once it is possible to become tissue-aware, as explained above, then it is no longer necessary to carry out such analysis on a voxel-by-voxel basis. Rather the system is able to determine where the organ lies say using a first radiopharmaceutical and then a second radiopharmaceutical may be imaged using the constraint of the organ location, the second radiopharmaceutical being able to locate the presence of the pathology.

Figure 8:
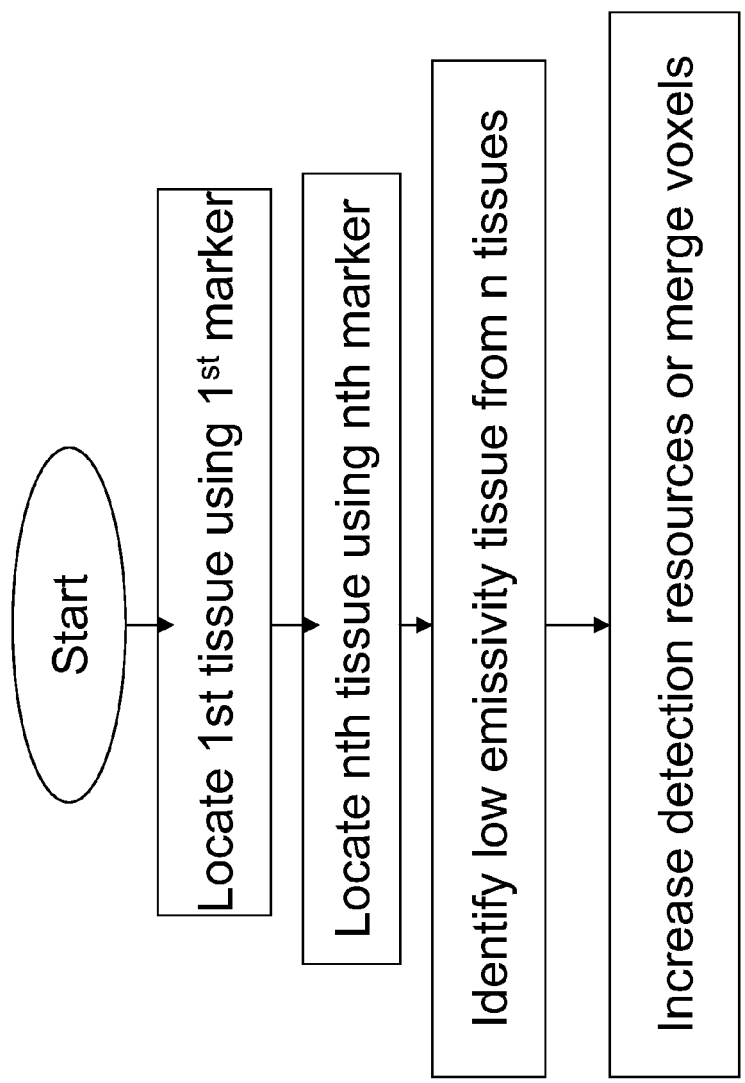

Reference is now made to FIG. 8 which illustrates a method for using the tissue aware properties of the present embodiments in order to tune detection to match tissue or organ emissivities. Generally, any region, no matter how much radiation it produces, can always be imaged sufficiently simply by leaving the measuring device in position for long enough. However, in many cases there may be limited time available. For such cases in which there is limited time for data acquisition, the present embodiments can be used to identify regions that may be expected to produce less emission. The system may then tune imaging resources or resolution onto those tissues according to the number of photons available. Clearly the more photons obtained the more reliable is the data, and therefore a tissue aware system is able to concentrate more detectors on the weaker signaling tissues.

If there are still not enough photons, or there are not enough detectors, then another way of pooling resources is to merge neighboring voxels (or regions). Such a procedure may reduce resolution, but will increase the overall number of photons for that merged region, and thus enable better classification of that region based on a more reliable photon count. Such a compromise enables analysis of the same collected data by ways that would allow high resolution where there are enough photons and lower resolutions where there are less while maintaining reliability of the analysis.

Again the tissue regions may be identified using multiple radiopharmaceuticals.

The above-described embodiment may lead to controlled sensitivity levels, currently not available with radioimaging.

The concept of using multiple antibodies can be used for therapy purposes, as in the following:

The specificity of a single antibody carrying a drug (or radioactive therapy) determines the chance for non-target tissue to receive the drug, and thus be subject to any toxicity of the drug. In cases where there are several antibodies, each with limited specificity, but with affinity to different 'background' tissue, a combination of antibodies may be used to improve the overall specificity, and thus to reduce overall toxicity and enable higher efficacy of treatment.

For example, if a first antibody (A1) based drug binds to the target N1 folds its affinity to the closest non-target tissue (B1), and a second antibody (A2) with similar drug has target affinity which is N2 folds higher than its closest non-target tissue (B2), then using a merged therapy will enable better target vs. non-target specificity, which is better than N1 and N2 (assuming B1 and B2 are different).

In a more generalized embodiment, the system may include a signal analysis module, including a library of patterns that are typical for every cell type. Each type of cells has one or more patterns associated with it, and the pattern determines how a set of radiopharmaceuticals injected according to a specific protocol (dosage, time, etc) may be expressed in that cell type. The analysis includes classification of the readings from each voxel based on correlation, or other statistical tools for assessing the most probable tissue classification for each voxel.

Since there may be several cell types for a given disease (e.g. cancer may show in several forms), the algorithm may be optimized to determine the exact tissue type per voxel or region. Alternatively, the algorithm may be optimized to determine the general property of diseased/non-diseased, while taking the specific classification only as a factor in the statistical analysis.

It should be noted that the system may allow for various protocols for administering the radiopharmaceuticals, where injection of the various radiopharmaceuticals may be simultaneous, or multiple injections at various times, as various radiopharmaceuticals have different lifetime in the circulation.

The issue of generating imaging using two or more radiopharmaceuticals is now considered mathematically.

An intensity distribution I, conventionally defined in terms of radioactive emissions per seconds, is now redefined as a vector of distributions over the volume U, forming our input space. Each dimension of the vector is a different one of the radiopharmaceuticals. The universal set U comprises a set of basic elements u (e.g., pixels in two dimensional spaces, voxels in three dimensional spaces), and I(u) is the intensity in a given basic element u∈U. For j radiopharmaceuticals this becomes $I(u)^{(j,t)}$ An inverse (or reconstruction) problem arises when one cannot sample directly from I, but can sample from a given set of views Φ. A projection φ∈Φ is defined by the set of probabilities {φ(u):u∈U}, where φ(u) is the probability of detecting a radioactive emission from a voxel u, as defined by viewing parameters, such as the physical and geometrical properties of the detecting unit, as well as the attenuation parameters of the viewed volume U, and the time parameters. A measurement is obtained by choosing a view φ∈Φ, and then sampling according to the viewing parameters.

For j radiopharmaceuticals or radiopharmaceuticals and k detectors, the probability of seeing a particle becomes $\phi_j^k(u)$ In the following analysis, I is the intensity of a radioactive substance, and the viewing parameters include the geometrical properties of a collimated detecting unit and the detecting unit's position and orientation with respect to volume U. The number of radioactive emissions counted by the detecting unit within a time interval is a Poisson distribution, where φ(u) is the detection probability of a photon emitted from voxel u∈U and the mean of the distribution is the weighted sum $\Sigma_{u \in U} \phi(u) I(u)$.

For the case of the kth detector a measurement $Y_k = \Sigma_{u \in U} X_t(u)$, where X(U) is a Poisson distribution.

$X_{(j,k,t)}(u) = I^{(j,t)}(u) \cdot \phi(u)_j^k(u)$.

Where $Y_{(j,k,t)} = \Sigma X_{(j,k,t)}(u)$.

Hence $Y_{(j,k,t)} = $ Poisson $(Y_{(j,k,t)})$

The projection set is thus defined by a matrix Φ, whose rows are the projections of the chosen views. I is a vector of densities (specified per each element in U), and ΦI is a vector of respective effective intensity levels for the views in the set. A vector of measurements y is obtained by a random sample from each view (according to the associated Poisson distribution). As discussed above, there are various known reconstruction methods that provide estimators for I given the projections Φ and the measurements y.

Using the above mathematics the problem is solved (an image created) one of the vectors say once an hour. The rates of change are determined. Simultaneously the problem is solved for another of the vectors at similar time intervals and the rates of change are determined. Then a stage of cross-identification is carried out between the two images, so that wanted tissues as identified by each image minus unwanted tissues identified by each image are concentrated on to form a new image. Cross-identification may be an iterative process.

In the example given above of the imaging of the heart using one blood radiopharmaceutical and one muscular tissue radiopharmaceutical, the areas identified by the blood radiopharmaceutical are subtracted. The areas identified by the muscle radiopharmaceutical are added, and those tissues not identified by either are likewise ignored as being signals from outside the target region.

The non-homogenous target area is typically a region of living tissue, generally belonging to a patient. The distinguishable regions within can be different tissues, different organs, a mixture of blood and organ tissue as with the above example of the heart, or tissue regions exhibiting differential pathologies.

An alternative to the above described approaches for imaging using two or more radiopharmaceuticals can be realized if one is able to distinguish between emissions of two or more radiopharmaceuticals by using low doses of the radiopharmaceuticals which do not cause spectral interference or masking (e.g. caused by Compton scattering). For example, 20 mCi of Tc-99m produces numerous photons in the tissue (due to Compton) which fall within the spectral line of Tl-201 (1-4 mCi). Reducing the Tc-99m dose to 2 or less mCi, results in minimal interference with Tl-201, and enables simultaneous imaging of the two isotopes.

Use of radiopharmaceutical cocktails enables generation of new products (for example, premixed radiopharmaceutical mixtures of two or more radiopharmaceuticals) and diagnostic procedures which enable multi-dimensional, differential diagnosis for revealing any pathology. It also requires significantly lower radiopharmaceutical dosage for each of the radiopharmaceutical in the mixture, thus a several-fold increase in sensitivity and significant improvement in spatial and spectral resolution. For example, full organ scans may be taken at less then 15 seconds, and preferably less than 10 seconds per scan. In more preferable embodiments, full organ scans may be taken at less than 7 seconds, or even less than 5 seconds, or less than 3 seconds per scan. It will be appreciated that even faster scans, for example, a full organ scan in less than 1 second may be realized. The organ may be a heart, a brain, a prostate, a kidney, a stomach, a uterus, a thyroid, or another body organ.

Radiopharmaceutical combinations are exemplified by liver-spleen scan+RBC+gallium (for cases of liver SOL/hemangioma/abscess/hepatoma). Bone scan+gallium or bone scan+In-WBC (for osteomyelitis). Perfusion rest/stress+MIBG for autonomic system in heart, mapping+BMIPP for heart failure with addition of FDG for viability. Assessment of the sentinel lymph node of tumors via Lymphoscintigraphy, (melanoma, breast, etc) with addition of FDG (and optionally MIBI) to assess the presence of tumor in these nodes (typically effected by peri-tumoral injection for lymphoscintigraphy and IV FDG). More detailed examples are provided protocol description, hereinbelow.

Although low doses are preferred for the reasons set forth hereinabove, higher doses can also be utilized in combinations provided one can effectively isolate the signal resultant from each radiopharmaceutical.

Simplified Scatter Correction in the Administration of Dual Isotopes

The present embodiment provides a method and apparatus for radioisotope that address shortcomings of present radioisotope imaging from subjects containing two imaging isotopes. Specifically, the present invention provides methods, and radioactive-emission cameras for two imaging isotopes, X1 and X2, wherein each isotope has a specific photon energy, for example, Y1 and Y2, respectively; wherein the energy state of Y1 is greater than the energy state of Y2 and Y1 scatter interferes with measurements of Y2.

In accordance with the present invention, imaging is performed with a fast radioactive-emission camera wherein two complete scans are taken, each is of a short duration, for example, in less than 2-5 minutes.

In and exemplary embodiment, a radiopharmaceutical of X1 is administered and an image of X1 is taken. The scatter at and around the region of Y2, i.e., the cross talk of X1 at and around Y2, is obtained.

Following imaging X1, radiopharmaceutical of X2 is administered and an image of X1+X2 is taken. The scatter of X1 in the region of Y2, the cross talk of X1 at and around Y2, is then subtracted from the image of X1+X2.

In an exemplary embodiment, Tl-201 and Tc-99m are administered in a myocardial perfusion study; Tc-99m having a photon emission at 140 KeV, and Tl-201 having a photon emission energy 70 KeV; resulting in cross talk around the 70 KeV region of Tl-201 photon emission.

In another exemplary embodiment, Tc-99m and In-111 are administered for pelvic SPECT imaging; Tl-201 having a photon emission energy 70 KeV as noted above and In-111 has a photon emission of 170 KeV; resulting in cross talk around the 140 KeV region of Tc-99m photon emission.

FIG. 11 is a flowchart for an imaging method 100 of two isotopes, such as X1 and X2, having distinct gamma energies, for example, Y1 and Y2, respectively, in accordance with some embodiments of the present invention. In an exemplary embodiment, the energy of Y1 is greater than the energy of Y2 and scatter from Y1 may interfere with measurements of Y2.

The imaging method 100 includes the following steps:

at 102 radiopharmaceutical X1 is administered;

at 104 a first shot duration image of X1 is obtained using a radioactive-emission camera at and around the energy region of Y2;

at 106 radiopharmaceutical X2 is administered while the patient remains under the fast radioactive-emission camera;

at 108, a second short duration image is obtained using the fast radioactive-emission camera, the image including includes energy at and around Y1 and Y2; and at 110 the image of X1 at and around the energy region of Y2, (at 104) is subtracted from the image of X1+X2 (at 110) substantially eliminating cross talk of X1 from Y2.

In an exemplary embodiment, the following procedure is used for imaging myocardial perfusion:

A patient undergoes a stress test and is injected at peak exercise with a standard dose of Tc-99m sestamibi. The dose may be reduced when using a high sensitivity radioactive-emission camera, thus minimizing scattered Tc-99m photons and patient radiation exposure.

After a recovery of approximately 60 minutes, the patient is positioned under a radioactive-emission camera. A brief pre-scan image of the Tc-99m-sestamibi distribution is obtained at and around 70 KeV; an energy associated with imaging of Tl-201. This scan is typically performed in under 2 minutes due to the sensitivity of the radioactive-emission camera and is used to subtract Tc-99m sestamibi cross-talk from the Tl-201 energy window in final image processing. While still under the radioactive-emission camera scanner, the patient is injected with a standard dose of Tl-201.

Simultaneous dual isotope data is then acquired, typically in less than 3 minutes. Utilization of the above-noted Tc-99m sestamibi scan, herein a "pre-scan", the resultant image can be resolved on a pixel by pixel basis. Execution of the pre-scan image is enabled by the rapid acquisition of a radioactive-emission camera, for example, as taught by commonly owned PCT/IL2005/000575, hereby incorporated in its entirety by reference.

It will be appreciated that similar performance can be achieved substituting one or more isotopes for Tc-99m sestamibi and/or Tl-201, providing that the speed of acquisition is much higher than today's standard.

Referring further to the drawings, FIG. 12 schematically represents a time line for myocardial perfusion, in accordance with the present invention.

Accordingly, at time zero, the patient begins physical exercise, represented as A. The exercise optionally lasts 10-15 minutes, and after about 7 minutes Tc-99m is administered, for example, by injection. The patient continues to exercise 1-3 minutes longer.

At 50 to 60 minutes later, a Tc-99m scan, lasting about 2-3 minutes, is obtained.

Preferably, while the patient remains under the scanner, Tl-201 is administered, for example, by injection.

Some 2-3 minutes after the second administration, a dual isotope scan, also lasting about 2-3 minutes is obtained.

Referring further to the drawings, FIGS. 13A-13B are schematic representations of a Tc-99m photopeak (FIG.

13A), a Tl-201 photopeak (FIG. 13B), and Tc-99m cross talk contribution to at and around the Tl-201 main energy window (FIG. 13C).

In accordance with a second example, the radioactive-emission camera is used for obtaining a pelvic SPECT, in two scans of rapid acquisitions, as follows:

i. administering In-111, having an energy of 170 Kev gamma;

ii. allowing distribution of In-111 and performing a first scan for the In-111 at and around the 140 KeV energy window of Tc-99m, iii. administering the Tc-99m, of 140 Kev gamma;

iv. allowing distribution of Tc-99m and performing a second scan of both Tc-99m and In-111; and v. subtracting the cross talk of In-111 at and around the 140 KeV energy window of Tc-99m from the second scan of both Tc-99m and In-111, wherein both the first and second scans are of short durations of about 2-4 minutes each.

The present embodiment is possible with a fast radioactive-emission camera, for example as taught by the present invention.

The aforementioned description is based on Okudan B, Smitherman T C. The value and throughput of rest Thallium-201/stress Technetium-99m sestamibi dual-isotope myocardial SPECT. Anadolu Kardiyol Derg. 2004 June; 4(2):161-8; Weinmann P, Faraggi M, Moretti J L, Hannequin P. Clinical validation of simultaneous dual-isotope myocardial scintigraphy. Eur J Nucl Med Mol Imaging. 2003 January; 30(1):25-31; Hannequin P, Weinmann P, Mas J, Vinot S. Preliminary clinical results of photon energy recovery in simultaneous rest Tl-201/stress Tc-99m sestamibi myocardial SPECT. J Nucl Cardiol. 2001 March-April; 8(2):144-51; Unlu M, Gunaydin S, Ilgin N, Inanir S, Gokcora N, Gokgoz L. Dual isotope myocardial perfusion SPECT in the detection of coronary artery disease: comparison of separate and simultaneous acquisition protocols. J Nucl Biol Med. 1993 December; 37(4):233-7; Lowe V J, Greer K L, Hanson M W, Jaszczak R J, Coleman R E. Cardiac phantom evaluation of simultaneously acquired dual-isotope rest thallium-201/stress technetium-99m SPECT images. J Nucl Med. 1993 November; 34(11):1998-2006; Knesaurek K, Machac J. Comparison of correction techniques for simultaneous 201Tl/99mTc myocardial perfusion SPECT imaging: a dog study. Phys Med Biol. 2000 November; 45(11):N167-76; Yang D C, Ragasa E, Gould L, Huang M, Reddy C V, Saul B, Schifter D, Rainaldi D, Feld C, Tank R A. Radionuclide simultaneous dual-isotope stress myocardial perfusion study using the "three window technique". Clin Nucl Med. 1993 October; 18(10):852-7; Nakamura M, Takeda K, Ichihara T, Motomura N, Shimizu H, Saito Y, Nomura Y, Isaka N, Konishi T, Nakano T. Feasibility of simultaneous stress 99mTc-sestamibi/rest 201Tl dual-isotope myocardial perfusion SPECT in the detection of coronary artery disease. J Nucl Med. 1999 June; 40(6):895-903; and Hannequin P, Mas J, Germano G. Photon energy recovery for crosstalk correction in simultaneous 99mTc/201Tl imaging. J Nucl Med. 2000 April; 41(4):728-36.

Signal Isolation

Another approach is signal isolation as detailed below.

In the present discussion, we denote the intensity density of isotope i in voxel u by $I^i(u)$. Detector t, detects $y_{tb}$ photons at energy bin b. (Note that previously the isotope was denoted by j and the detector by k, yet these notations are equivalent.) We refer to a detector as a composite of a collimator and a radiation sensor such as CZT, placed at some location. In an actual system, a physical detector that takes snap shots from several locations is regarded as different detectors for the purpose of the following derivations.

We denote by $\phi_{tb}^i(u)$ as the probability of a photon emitted from isotope i in voxel u, to be detected by detector t at energy bin b.

This probability is determined by the geometrical and physical properties of the detector, its position, orientation, and the reduction of the energy of the photon emitted from isotope I, to the measured energy b. We will refer to $\phi_{tb}^i(u)$ as the functional in the following derivations. The functional can be either, analytically calculated via geometry together with applying the Compton Effect for scattering, measured via experiment, or partly calculated and tuned via experiment.

FIGS. 14A-14E illustrate energy and angular relations in Compton Scatter, for treatment in accordance with embodiments of the present invention.

The change of an angle θ of a photon emitted at energy $E_0$, and scattered to energy E is given by the Compton scatter equation, as follows:

$$E(E_0, \theta) = E_0 \left[ \frac{m_e c^2}{m_e c^2 + E_0(1 - \cos(\theta))} \right] \Leftrightarrow \cos(\theta) = 1 - \left(\frac{1}{E} - \frac{1}{E_0}\right) m_e c^2,$$

Where $m_e$ represents the rest mass of the electron, and c is the speed of light in a vacuum.

Figure 14A:
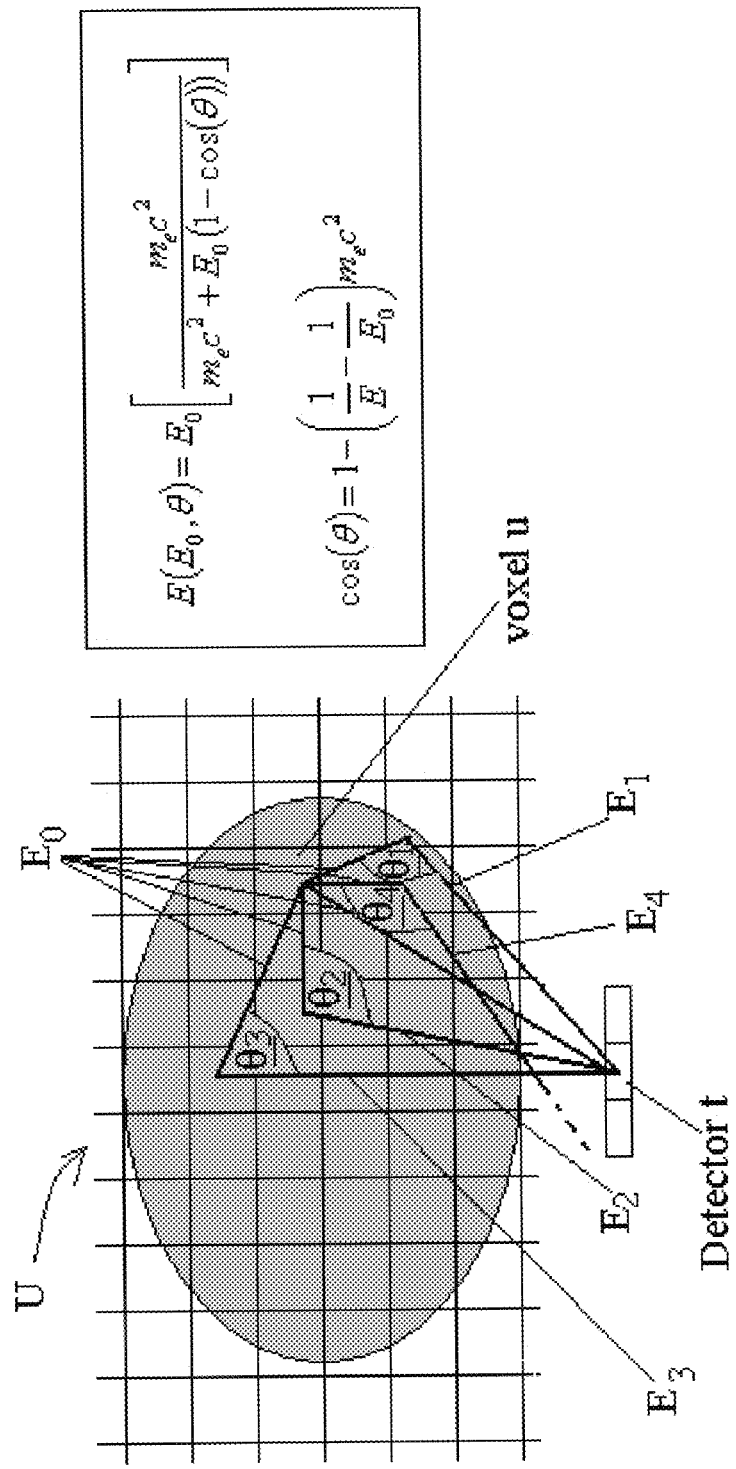

FIG. 14A illustrates a source of a single isotope j=1, at a voxel u, emitting several photons 1, 2, 3, 4, and 5, of an initial energy $E_0$, wherein:

photon 1 is scattered and reflected by an angle $\theta_1$ and reaches detector t at the energy $E_1$, as described by the Compton scatter equation;

photon 2 is scattered and reflected by an angle $\theta_2$ and reaches detector t at the energy $E_2$, as described by the Compton scatter equation;

photon 3 is scattered and reflected by an angle $\theta_3$ and reaches detector t at the energy $E_3$, as described by the Compton scatter equation;

photon 4 is scattered and reflected by an angle $\theta_4$ away from detector t, as described by the Compton scatter equation;

photon 5 reaches detector t directly, with no scatter, at the energy $E_0$.

Figures 14B, 14C, 14D, 14E:
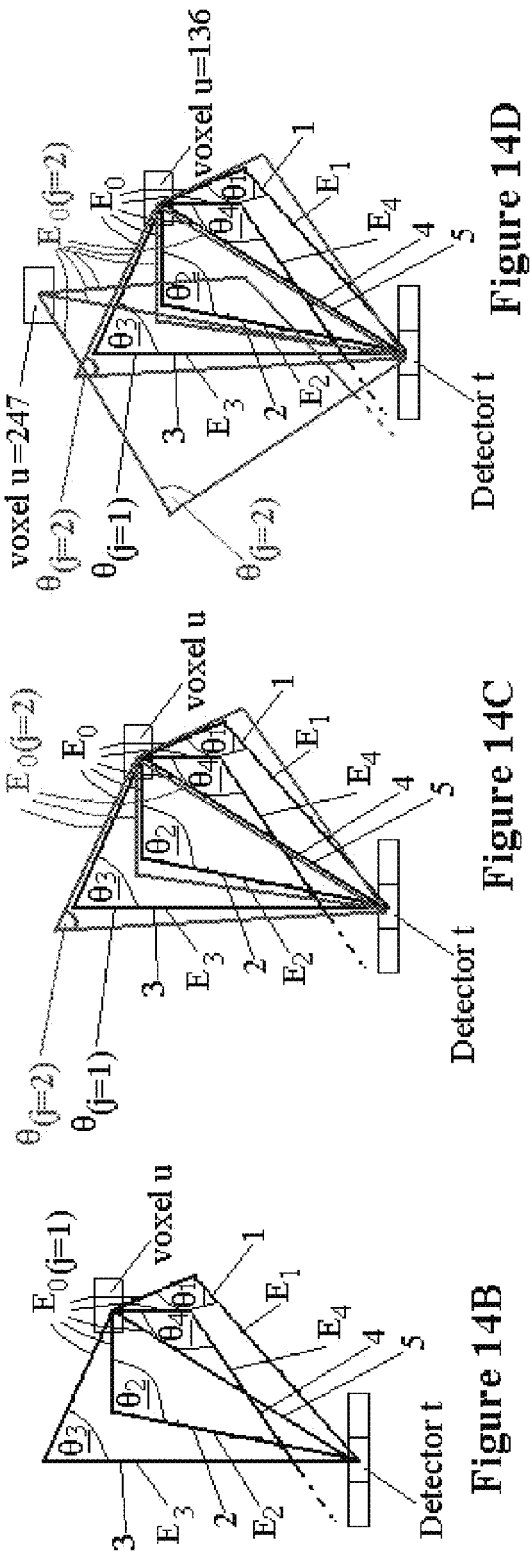

FIG. 14B illustrates two isotopes j=1, and j=2, at the voxel u, emitting several photons, of an initial energy $E_0(j=1)$ and $E_0(j=2)$, wherein photons of $E_0(j=1)$ are reflected according to the Compton scatter equation, by a scatter angle θ(j=1) and photons of $E_0(j=2)$ are reflected according to the Compton scatter equation, by a scatter angle θ(j=2).

FIG. 14C illustrates a still more complex situation, where differentiation is sought. For example, isotope j=1 occurs only in a voxel u=136, while isotope j=2 occurs both at the voxel u=136 and at a voxel u=247.

Given a fixed geometry between the detector t and the voxel u, and an initial energy $E_0$, for each scattered energy level, such as $E_1$, $E_2$, or $E_3$, there is a unique scattering angle (or absolute value thereof) that will facilitate detection. For example, since $\theta_1$ and $\theta_2$ are substantially equal in terms of absolute values, the energies $E_1$, $E_2$ are also substantially equal. In consequence, for each geometry there is a population of Energies, scatter direction and angles, that will meet the Compton scatter equation.

Thus, as illustrated in FIG. 14E, for a fixed geometry between the detector t and the voxel u, and for an initial energy $E_0$, each energy bin is associated with a single scattering angle θ of an initial energy $E_0$.

This limitation is applied to the following analysis. Thus, a method of image reconstruction is provided, as follows:

i. modeling photon scatter for each isotope j, based on the Compton scatter equation, relating initial and final photon energies to a Compton scatter angle;

ii. employing an iterative process for generating a solution for the image reconstruction, by describing a probability that an emitted photon of an isotope j, from a voxel u, will be detected by a detector t, at an energy bin b.

A possible iterative process is described below.

The random count $X_{tb}^i(u)$ of photons that are emitted from voxel u and detected in measurement tb(detector t at energy bin b), is modeled by a Poisson process with mean $\Sigma_i \phi_{tb}^i(u) I^i(u)$. The total count of photons detected in measurement tb is $Y_{tb} = \Sigma_u X_{tb}(u)$, and the problem is to reconstruct the intensities $I^i(u)$ from the measurements $y_{tb}$.

Simultaneous Submission of Multiple Isotopes

In a first case, multiple isotopes are administered simultaneously.

The measurements have a Poisson distribution $Y_{tb} \sim \text{Poiss}(\Sigma_i \Sigma_u \phi_{tb}^i(u) I^i(u))$.

The log-likelihood is given by:

$$L(y/I^1, I^2, \ldots) = \Sigma_{tb} \ln \text{Poiss}(y_{tb}/\Sigma_i \Sigma_u \phi_{tb}^i(u) I^i(u)) = \Sigma_{tb}\{-\Sigma_i \Sigma_u \phi_{tb}^i(u) I^i(u) + y_{tb} \ln[\Sigma_i \Sigma_u \phi_{tb}^i(u) I^i(u)] - \ln(y_{tb}!)\}$$

The maximum likelihood is the solution of set of non-linear equations:

$$\sum_{tb} \sum_u \phi_{tb}^i(u) = \sum_{tb} \frac{\phi_{tb}^i y_{tb}}{\hat{y}_{tb}},$$

for all i where $\hat{y}_{tb} \equiv \Sigma_i \Sigma_u \phi_{tb}^i(u) I^i(u)$.

The solution may be solved via the EM approach:

$$X_{tb}^i(u) \sim \text{Poiss}(\phi_{tb}^i(u) I^i(u)).$$

The likelihood of the complete data:

$$\ln P(x/I^1, I^2, \ldots) = \Sigma_{tb} \Sigma_i \Sigma_u \{-\phi_{tb}^i(u) I^i(u) + x_{tb}^i(u) \ln[\phi_{tb}^i(u) I^i(u)] - \ln(x_{tb}^i(u)!)\}$$

The EM based algorithm:

$$I^i(u) = \frac{1}{\sum_{tb} \phi_{tb}^i(u)} \sum_{tb} \frac{y_{tb}}{\hat{y}_{tb}} \phi_{tb}^i(u) I^i(u),$$

for all i where $\hat{y}_{tb} \equiv \Sigma_i \Sigma_u \phi_{tb}^i(u) I^i(u)$.

This is the basis for faster Ordered set based algorithms.

Two Separate Submissions of Two Isotopes—Two Step Estimation:

The following models situations of two-step administrations. We first submit isotope i=1, and scan. We estimate its density distribution $I^1(u)$ using an EM based algorithm. Then we submit isotope i=2, while i=1 is still distributed in the volume. To estimate $I^2(u)$ given the estimated $\hat{I}^1(u)$:

$$I^2(u) = \frac{1}{\sum_{tb} \phi_{tb}^2(u)} \sum_{tb} \frac{y_{tb}}{\hat{y}_{tb}} \phi_{tb}^2(u) I^2(u),$$

for all i=2 where $\hat{y}_{tb} \equiv \Sigma_u \phi_{tb}^2(u) I^2(u) + \Sigma_u \phi_{tb}^1(u) \hat{I}^1(u)$.

Extension to multiple submissions is straightforward.

2 separate submissions two Isotopes—combined estimation

We first submit isotope i=1, and scan. We denote the measurements of the first scan by $y_{tb}^{(1)}$.

We then submit isotope i=2, and scan. In this scan the two isotopes are distributed.

We denote the measurements of the first scan by $y_{tb}^{(2)}$.

We wish to estimate both distributions $I^1(u)$ and $I^2(u)$ using the measurements from both scans $y_{tb}^{(1)}$ and $y_{tb}^{(2)}$.

We discriminate between the functionals of the first scan $\phi_{tb}^{1(1)}$, and those of the second scan $\phi_{tb}^{1(2)}$, $\phi_{tb}^{2(2)}$.

The measurements have the Poisson distributions:

$y_{tb}^{(1)} \sim \text{Poiss}(\Sigma_u \phi_{tb}^{1(1)}(u) I^1(u))$ $y_{tb}^{(2)} \sim \text{Poiss}(\Sigma_u \phi_{tb}^{1(2)}(u) I^1(u) + \phi_{tb}^{2(2)}(u) I^2(u))$ The solution based on the EM approach:

$$I^1(u) = \frac{1}{\sum_{tb} \phi_{tb}^{1(1)}(u) + \phi_{tb}^{1(2)}(u) + \phi_{tb}^{2(2)}(u)} \sum_{tb} \left( \frac{y_{tb}^{(1)} \phi_{tb}^{1(1)}(u)}{\hat{y}_{tb}^{(1)}} + \frac{y_{tb}^{(2)} \phi_{tb}^{1(2)}(u)}{\hat{y}_{tb}^{(2)}} \right) I^1(u), \quad \text{for all } i=2$$

for all i=2

$$I^2(u) = \frac{1}{\sum_{tb} \phi_{tb}^{1(1)}(u) + \phi_{tb}^{1(2)}(u) + \phi_{tb}^{2(2)}(u)} \sum_{tb} \left( \frac{y_{tb}^{(2)} \phi_{tb}^{2(2)}(u)}{\hat{y}_{tb}^{(2)}} \right) I^2(u)$$

Where $\hat{y}_{tb}^{(1)} \equiv \Sigma_u \phi_{tb}^{1(1)}(u) I^1(u)$ $\hat{y}_{tb}^{(2)} \equiv \Sigma_u \phi_{tb}^{1(2)}(u) I^1(u) + \phi_{tb}^{2(2)}(u) I^2(u)$ The above described algorithm enables identification of the different energy level photons (energy signature) emitted from a radioisotope (produced from directly collected photons as well as photons generated from Compton scattering), or a plurality of radioisotopes (e.g. cocktail) administered to a body and detected by a scintillation camera. Thus, such an algorithm enables association between various energy level photons and an isotope source. In essence, this algorithm produces for every radioisotope an energy signature which is composed of the various energy photons produced thereby in a body as a function of a voxel imaged by the camera.

The above described algorithm can serve as a basis for more advanced imaging which enables specific tissue imaging by accounting for time distribution of radiopharmaceuticals (especially radiotracers).

It will be appreciated that the EM approach for a single isotope may be described for example, in U.S. Pat. No. 6,943, 355, whose disclosure is incorporated herein by reference. Yet, their analysis does not include the multiple isotope treatment.

In contrast, the present invention teaches monitoring distribution of each radiotracer as a function of energy intensity emitted therefrom and a function of time. Using the above described algorithm one can associate each voxel imaged with a tissue and a radiotracer signal signature.

Such association provides numerous benefits in imaging since it enables identification of specific pathologies, confirmation of pathologies via multi-tracer comparison and use of radiopharmaceuticals which include the same radioisotope attached to a different tracer. It will be appreciated that time dependent distribution of radiotracers can be generated on the fly or derived from data provided by the manufacturer. In any case, such data is used to correlate Voxel photons to a tissue and radiotracer thereby enabling accurate imaging even in cases where several radiotracers having the same isotope or in cases where Compton scattering of one radiotracer generates photons which are naturally produced by another radiotracer.

Referring further to the drawings, FIGS. 10A-10G schematically illustrate the use of multiple isotopes for differentiation, in accordance with the present invention.

Figure 10A:
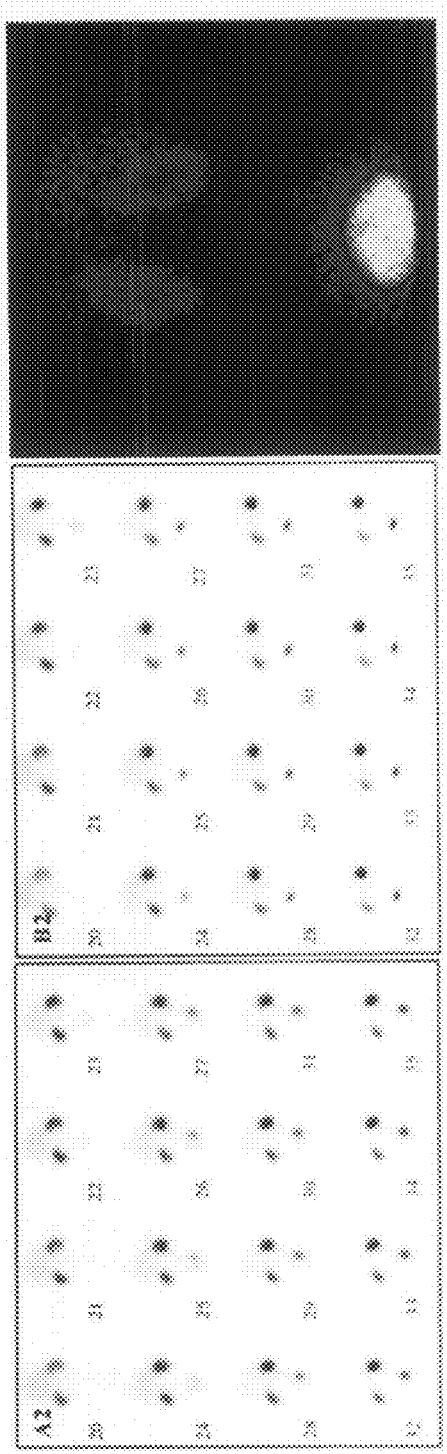

As seen in FIG. 10A, Renal Function—Dynamic Flow Study is performed, using In-111-DTPA and Tc-99m-MAG3, for assessment of filtration and extraction. Administration and acquisition is simultaneous, and imaging is performed about 30 minutes after injection, sampling every minute, until urine secretion is visible.

As seen in FIG. 10B, a single, simultaneous administration of:

1. Tc-99m-DMSA, for glomerular filtration;
2. Tc-99m-Red Blood Cell, for blood flow;
3. Ga-67, for inflammation/infection, is employed in place of the current 2-step approach of separate administrations of Tc-99m-DTPA and Aortogram.

FIGS. 10C-10E describe a differential diagnosis of coronary bypass follow-up, described in Example 6, hereinbelow.

Figure 10F:
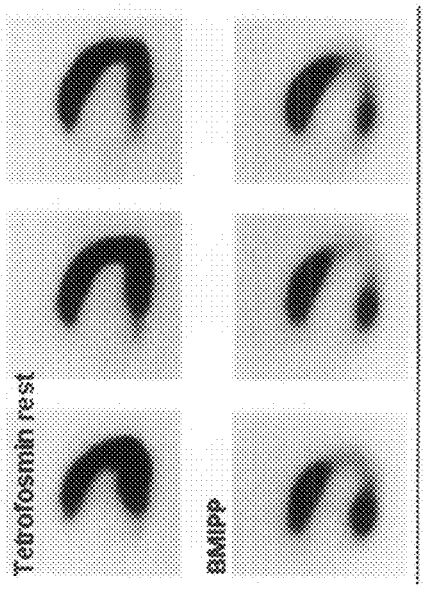
Figure 10G:
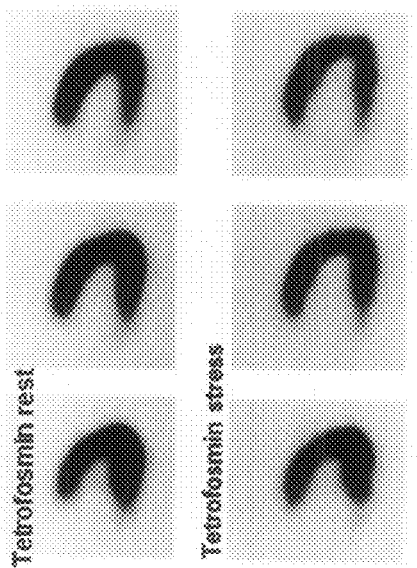

FIGS. 10F-10G describe a single step dual isotope administration of perfusion and viability, using Tetrofosmin and BMIPP.

In addition to the advantages described above (e.g. tissue mapping and differential diagnosis) use of radiopharmaceutical cocktails and simultaneous dual imaging is also advantageous in that administration of two or more radiopharmaceuticals via a single injection shortens patient cycle time since there is now one imaging phase rather than two.

Kinetics

Kinetics of radiotracer distribution and derivation of data from such distribution is exemplified by the following equation.

Suppose one tracer has uptake over time curve $C1(t)$, and a second tracer has uptake over the time-curve $C2(t)$. Both use the same isotope (e.g. Tc-99m). If both are injected at the same time (or separate time $dT$), the reading will be:

$$\text{Reading}(t) = A*C1(t) + B*C2(t-dT)$$

A and B relate to the response of the specific tissue location to the presence of tracers 1 and 2 in the blood. C1 and C2 are known in the literature for various body organs, various injected doses, various patient conditions (e.g. blood pressure, blood flow, . . . ), etc.

Therefore, a de-convolution process may enable separation of the Reading(t) into its components $A*C1(t)$ and $b*C2(t)$, . . . and A and B represent the tissue response.

By looking at the absolute values of A and B (compared with literature), their relative values (e.g. A/B), or their values vs. other organ location abnormalities can be detected. Clearly, many more than just 2 tracers can be used, and injection does not have to be at once or at only two instances, but rather there may be any injection timeplan $P(t)$, and thus an expected level in the organ is a convolution of $C1(t)$ with $P1(t)$. The injection timeplan can controlled and adjusted in response to the voxel readings, so as to emphasize specific time points of interest.

For example, the time in which one radiotracer is expected to peak and the other to diminish, etc. In particular, it can detect the best timing to begin/increase/decrease/stop injections.

Another equation can be used to generate a tissue probability index for an imaged voxel as a function of time.

$$\text{Intensity}(\text{voxel})^{(t)} = \Sigma_i P_i(t) C_{i,k,n}^{(t)}$$

Wherein:

P=injected dose
i=intensity
k=tissue type
n=state
C=function of tracer
(t)=time

Thus, $C_{i,k,n}^{(t)}$ expression curve of a radiotracer 'i' in tissue 'k' (e.g. heart,-liver muscle blood) having a pathological state 'n' (e.g. normal, ischemic, tumor, abnormal physiology, scar). $C_i$ is a vector that express the level of emission of each energy level of a radiotracer. It is possible that several tracers 'i' would produce the same energy spectra lines, for example when different tracers are bound to the same isotope.

P can further depend on the location of injection, in case of non-systemic injection (e.g. in cases of direct organ injection).

C is typically provided by the tracer manufacturer or by researchers that mapped the uptake of the radiotracer in various tissues and pathologies, and C may further be expressed by using a parametric model, for example by using commonly acceptable bioavailability coefficients of the tracer. For example, uptake and clearance coefficients, interaction coefficients and the like.

C can also be expressed in various patient populations (grouped by gender, age, medical history) and under various physiological conditions (rest, stress, stimulation, drugs).

The above described equation can be utilized to reconstruct the 'k' and 'n' per voxel, which are most likely to match the reconstructed voxel intensity.

'k' and 'n' can also be constrained by prior knowledge, such as expectation of presence of a specific type of tissue at a voxel or voxels, and expected specific type of pathologies (prior knowledge of a suspected pathology). 'k' and 'n' can also be constrained by information relating to neighboring voxels or reference voxels which have been previously determined, using for example, x-ray imaging.

Reconstruction of the bioavailibilty of a radiotracer for each voxel can also be effected by reconstructing the kinetics of each tracer for each voxel followed by matching the parameters rather than the time series of the intensities at each voxel.

Following the above described processing, the present system can represent data to the operator (physician) as intensity over time, at each voxel, parameteric representation (ratios between different radiotracers and the like which can be color coded) and finally assigning a probability to the classification, e.g., 95% normal, 3% typed pathology etc.

Reconstruction of the 'k', 'n' or the parametric representation of the Ci may be utilized for further iteration and refinement of voxel intensity over time. It can be further improved and provide a method for the direct recovery of the parametric representation or the classification of a voxel ('k', 'n') without necessitating recovery of the voxel intensity over time. In this case, the kinetics equation are incorporated into the 3-D reconstruction model which is based upon camera readings.

Thus, according to another aspect of the present invention there is provided a system which enables time dependent analysis of voxel spectral information from one or more radioisotopes to thereby enable more accurate tissue mapping and pathology diagnosis.

The system according to this aspect of the present invention performs three main functions, acquisition of photons, association of each photon to a radioisotope source and a voxel as a function of time and image reconstruction from voxels (association of each voxel to a tissue or pathology)

Thus, these system not only measures the accumulated level at a given time, but also recovers kinetics parameter and thus enables to differentiate between multiple tracers (even if they have similar isotope) according to their time behavior profile (which can be derived from, or verified against their profile as generated by the manufacturer which can be used to further verify the location of a voxel in the body and associate other adjacent voxels to adjacent tissues and body regions.

Result of such imaging can denote probability of tissue imaged and state of the tissue. For example, a single voxel, or a collection of voxels associated with a specific tissue region (e.g. heart) can be used to generate a probability diagnosis as follows: 87%—normal, 9%—ischemic, 3% scar, 1%—tumor according to the parameters derived from radioisotope mapping as a function of time and photon signature and further as a function of radiotracer association.

This also applies to cases where the tissue is not known. Again, a probability distribution can also be generated in such cases. For example, blood pool imaging (by dynamic flow imaging) can help the algorithms know where blood is and where muscle is, thus the reconstruction algorithm described herein can take that into account by subtracting from voxel maps of radiotracers which attach only to muscle the blood pool imaging maps.

A higher level analysis can be done to determine disease diagnosis, not per voxel, but rather by providing to the system prior info on the disease and how it is typically manifested in patients. This embodiment of the present system (which includes a large database) can support diagnostic decision making.

The spatial dimensions and at least one other dimension, and an image four-dimension analysis unit analyzes the intensity data in the spatial dimension and said at least one other dimension in order to map the distinguishable regions. The system typically detects rates of change over time in signals from radiopharmaceuticals and uses the rates of change to identify the tissues. In a preferred embodiment, two or more radiopharmaceuticals are used, the results of one being used as a constraint on the other.

Voxel Dynamic Modeling

Dynamic modeling is a technique in which the parameters of a dynamic system are represented in mathematical language. Dynamic systems are generally represented with difference equations or differential equations. Measurements obtained from the modeled system can then be used to evaluate the values of parameters of interest that cannot be measured directly.

In the present case, the system being modeled is the body structure (or portion thereof) being imaged. During imaging, the emmitance from a given voxel is affected by the chemical properties of the radiopharmaceuticals well as by the half-life of the tracer, as well as by the nature of the body structure being imaged. For example, the chemical properties of the antibody to which the tracer is attached govern factors such as binding to the tissue, accumulation, and clearance rate.

The goal of the presented models is to recover the kinetics per voxel of one or more parameters of interest. Each of the models reflects a different mechanism for the diffusion of the radiopharmaceutical into and out of the voxel, as well as the possibility of accumulation within the voxel. For a given measurement process the dynamic model should be selected to match the known properties of the radiopharmaceutical being used.

Reference is now made to FIG. 15, which is a simplified flowchart of a method for measuring kinetic parameters of a radiopharmaceutical in a body, according to a preferred embodiment of the present invention. In step 6010, the radiopharmaceutical is administered to the body. In step 6020, the body or a portion of the body are imaged. In step 6030, a model is provided for obtaining kinetic parameters from the imaging is provided. Several preferred embodiments of dynamic models are presented below. Finally, in step 6040, the kinetic parameters are obtained by applying the measurements to the provided model in order to extract the value of the required parameter(s). The kinetic parameters may provide information on factors such as actual uptake, rate of uptake, accumulation, and clearance of the radiopharmaceutical, which in turn provide information about the health of tissue in the voxel. The obtained parameter values can thus be analyzed to evaluate the health of the imaged body structure and of other portions of the body (for example renal functioning). (See description of expert system) The parameter values can also be analyzed and used to control future administration of the radiopharmaceutical (See description of closed loop injection system). The parameters obtained in step 6040 preferably include at least one of: local (in-voxel) representation of blood pool, blood flow, and diffusion to and/or from the local tissue as representative of function (e.g. viability).

Three preferred embodiments of dynamic models for provision in step 6030 are now presented. The following rationale and assumptions are common to all of the presented embodiments.

The analysis is of one voxel versus the rest of the body, not of the entire organ.

The dynamic model relates the per pixel emission levels to factors such as the blood in voxel, the tissue in voxel (and uptake from blood), and blood re-fill (perfusion/flow).

An additional assumption is that the amount of the tracer in the voxel is insignificant compared with the rest of the body and with the global blood pool. Therefore, the voxel in the region of interest (ROI) is affected by the global blood pool, but does not affect it. As a result, the concentration of tracer in the global blood pool can be recovered separately by one or more of: modeling the known kinetics given the exact injected dose, measuring the concentration at a pre-identified blood region using the imaging equipment, or by taking blood samples over time.

It is also assumed that the concentration of the tracer in the global blood may be controlled in a complex fashion by various injection profiles, such as:
1) Bolus injection
2) Constant drip
3) Smart injection—in which the radiopharmaceutical is injected in a controlled manner over time. The smart injection profile may be predetermined, or responsive to external events and/or feedback from the imaging equipment (see closed loop description). For example, rather than injecting a single bolus dose of radiopharmaceutical, one can inject a tenth of the dose for each of a series of ten injections. Examples of smart injection profiles are described below.

It is assumed that in ischemic conditions, not enough blood flow reaches the voxel, thus the concentration of the tracer in the blood of that voxel is different than in global blood pool. For example, if oxygen is the tracer, then ischemic region has lower oxygen concentration in the capillaries than in global blood pool due to poor refill.

An additional assumption is that the processes affecting the tracer concentration are slower than fractions a second, so that the volume and flow values (as defined below) relate to an average over the heart cycle. Thus gating will not separate the uptake into the tissue for different time slices in the heartbeat. Gated analysis (which is synchronized with the heart cycle) may be developed for fast processes which do not involve slow accumulation in the muscle tissue, or, alternatively, model the accumulation, both of which requires motion compensation.

A final assumption is that each voxel is large enough so that variables may be defined to relate to the voxel structure in global terms. The dynamic models described below are for voxels having a millimetric size, which are therefore significantly larger than the blood vessels (unlike during imaging of blood vessels). The models therefore include parameters for both blood and tissue parameters. In cases where a very high-resolution reconstruction (i.e. sub-millimetric) is required, a different model should be applied to handle voxels which are pure blood (e.g. voxels inside coronaries).

The following parameters are defined for all of the dynamic model embodiments presented below:

1) $Vt$—Volume of tissue in voxel.
2) $Vb$—Volume of blood within the capillaries in the given voxel. $Vb$ is normally constant for a given tissue type, but may vary for different tissue types such as blood vessel, connective tissue, or tumor before or after angiogenesis
3) $V$—Voxel volume. The voxel volume is the sum of the tissue volume and blood volume within the voxel:

$$V = Vt + Vb \quad (1)$$

$V$ is a fixed value dictated by the imaging equipment (i.e. camera) performing the radioactive-emission measurements.

4) $Rb$—Density of blood within the voxel. $Rb$ is the ratio of the volume of the blood in the voxel to the total voxel volume:

$$Rb = Vb/V \quad (2)$$

For example, in cross section, the diameter of a capillary is about 10-15 um. To allow diffusion to cells the capillaries are spaced about 50-150 um apart. Therefore, it is reasonable to assume that healthy tissue has $Rb \sim 1\text{-}5\%$ 5) $F$—Blood flow to voxel. It is assumed that blood flow is not affected by neighboring voxels (i.e. blood flow is of "fresh" blood from the arteries).

6) $Cb$—Tracer concentration in blood within the voxel (reflects the capillaries in the voxel).

7) $Ct$—Tracer concentration in tissue within the voxel.

8) $C$—Tracer concentration in voxel, as measured by the imaging equipment.

9) $Cg$—Tracer concentration in global blood. The concentration in the global blood supply is assumed to be given. C may be determined with a separate model, or by measuring the global blood concentration directly. A full model of $Cg$ should reflect many of the patient's conditions, including cardiac output, prior diseases (such as metabolic disorders or diabetes), hyper/hypo-fluid volume, hyper/hypo-blood pressure, liver and/or kidney function, drugs (diuretics), and so forth.

Note that all of the above parameters other than $Cg$ are defined per voxel.

Reference is now made to FIG. 16, which is a schematic representation of a dynamic model of a voxel, according to a first preferred embodiment of the present invention. The present embodiment (denoted herein model 1) assumes symmetric diffusion (i.e. the tracer diffusion coefficients into and out of the voxel are equal), and that there is no accumulation of the tracer within the voxel. FIG. 16 illustrates the role of each of the parameters described above.

The radioactive pharmaceutical is introduced into the global blood pool 6110 by injection according to an injection profile 6120. The radiopharmaceutical is conveyed to the voxel via the circulatory system 6125. The radiopharmaceutical flows through the voxel via the capillaries 6130 running through the voxel at flow rate F. Diffusion from the capillaries 6130 to the voxel tissue 6140 (uptake) and from the voxel tissue 6140 to the capillaries 6130 (release) occurs with a common diffusion coefficient Kd. Kd is an effective coefficient which takes into account both the uptake and outtake diffusion coefficients, and the surface area to volume ratio of the capillaries 6130. The remainder of the pharmaceutical is dispersed to the rest of the body for uptake and clearance 6145.

Similar or identical components are indicated with the same reference numbers throughout the figures.

Model 1 assumes tracer delivery to the voxel by diffusion to and from the local tissue, rather than by accumulation and dissolution. Therefore, model 1 can serve for applications with materials like Thallium and CardioTech, but not with Mibi which accumulates due to different diffusion rates in and out of the tissue. Models 2 and 3, which are presented below, allow for accumulation, and are therefore more suitable for radiopharmaceuticals such as Mibi.

Equations 3-5 present the relationship between the kinetic parameters for model 1:

$$C = \frac{Ct \cdot Vt + Cb \cdot Vb}{V} \quad (3)$$
$$= Cb \cdot Rb + Ct \cdot (1 - Rb)$$

$$\frac{dCt}{dt} = Kd(Cb - Ct) \quad (4)$$

$$\frac{dCb}{dt} = \frac{F}{Vb}(Cg - Cb) - Kd(Cb - Ct) \quad (5)$$

C is measured dynamically by the imaging equipment and Cg is determined separately by measurement or independent modeling from the art.

Reference is now made to FIG. 17, which is a schematic representation of a dynamic model of a voxel, according to a second preferred embodiment of the present invention. The present embodiment (denoted herein model 2) assumes symmetric diffusion, with a diffusion coefficient of Kd. As in model 1, Kd is an effective coefficient which takes into account both the uptake and outtake diffusion coefficients, and the surface area to volume ratio of the capillaries 6130. However, in contrast with model 1, model 2 assumes that a fraction 6150 of the tracer concentration within the tissue is accumulated and is not diffused back to blood (for example by metabolism). The tracer accumulation within the voxel occurs at a rate of A.

Equations 6-9 present the relationship between the kinetic parameters for model 2:

$$C = \frac{Ct \cdot Vt + Cb \cdot Vb}{V} + Accum \quad (6)$$
$$= Cb \cdot Rb + Ct \cdot (1 - Rb) + Accum$$

$$\frac{dCt}{dt} = Kd(Cb - Ct) - A \cdot Ct \quad (7)$$

$$\frac{dCb}{dt} = \frac{F}{Vb}(Cg - Cb) - Kd(Cb - Ct) \quad (8)$$

$$Accum = \int_0^t A \cdot Ct \, dt \quad (9)$$

Initial conditions: Ct=0, Cb=0, Accum=0

Reference is now made to FIG. 18, which is a schematic representation of a dynamic model of a voxel, according to a third preferred embodiment of the present invention. The present embodiment (denoted herein model 3) assumes asymmetric diffusion, with uptake and release occurring according to the blood concentration (vs. zero) for uptake, and to the tissue concentration (vs. zero) for release, not according to the difference in concentrations (blood vs. tissue) as in model 1. Transport to the tissue is modeled by a diffusion coefficient of Kin, depending only on the outside concentration of capillary blood. Outgoing transport is modeled by a diffusion coefficient of Kout for outgoing transport, depending only on the internal (tissue) concentration. This way, accumulation is described by a high Kin and a low Kout. Kin and Kout are effective coefficients, which account for the surface area to volume ratio of capillaries.

Equations 10-12 present the relationship between the kinetic parameters for model 3:

$$C = \frac{Ct \cdot Vt + Cb \cdot Vb}{V} \quad (10)$$
$$= Cb \cdot Rb + Ct \cdot (1 - Rb)$$

$$dCt/dt = Kin \cdot Cb - Kout \cdot Ct \quad (11)$$

$$dCb/dt = F/Vb(Cg-Cb) - Kin \cdot Cb + Kout \cdot Ct \quad (12)$$

Initial conditions: Ct=0, Cb=0

Models 2 and 3 are suitable for use with tracers like Thallium and Mibi, since they do not assume symmetric diffusion to/from the local tissue, but rather allow accumulation.

Regarding the parameters of the above described dynamic models, it may be possible to attribute the physiological meaning as follows:
1) F may correspond to perfusion
2) Kd+A may correspond to viability and metabolism (Model 2)
3) Kin may correspond to viability (Model 3)

Referring again to FIG. 16, in step 6040 the kinetic parameters for the voxel are obtained by applying the measured values to the provided model and extracting the value of the required parameters. Parameter extraction may be performed utilizing any technique known in the art, such as numerical analysis. Repeated measurements may be made of the given voxel, and the parameters calculated with increasing accuracy.

In a preferred embodiment, parameter extraction the dynamic system is provided in step 6030 as an analogous RLC electronic circuit. An RLC circuit is an electrical circuit consisting of resistors (R), inductors (L), and capacitors (C), connected in series and/or in parallel. Any voltage or current in an RLC circuit can be described by a second-order differential equation. Since all of the above described models present the voxel kinetic parameters as a second order system, the dynamic model provided in step 6030 may be described as an arrangement of resistors, capacitors, and inductors.

Voltage analysis of an RLC circuit is based on expressing the voltage over each of the circuit elements as a function of the circuit current as follows:

Resistor:
$$V_R(t) = R \cdot i(t) \quad (13)$$

Capacitor:
$$V_C(t) = \frac{1}{C} \int_{-\infty}^t i(\tau) d\tau \quad (14)$$

Inductor:
$$V_L(t) = L \frac{di}{dt} \quad (15)$$

As an example of RLC circuit analysis, consider the series RLC circuit 6160 shown in FIG. 19. RLC circuit 6160 consists of resistor 6165, inductor 6170, and capacitor 6175 connected in series, with an input voltage provided by voltage source 6180. In a series RLC circuit, the total voltage drop over the circuit is the sum of the voltage drop over each of the circuit elements, so that:

$$V(t) = R \cdot i(t) + L\frac{di}{dt} + \frac{1}{C} \int_{-\infty}^t i(\tau) d\tau \quad (16)$$

and $$\frac{dV}{dt} = L\frac{d^2 I}{dt^2} + R\frac{di}{dt} + \frac{1}{C} i(t) \quad (17)$$

Presenting the dynamic model as an RLC circuit enables using well-known circuit analysis techniques to derive the values of the desired parameters based on the measurements, and to analyze the behavior of the dynamic system. In terms of the above-described dynamic modeling, the voltage, V, represents the administered radiopharmaceutical, and dV/dt represents the rate of change of the administered radiopharmaceutical, that is the administration protocol. The circuit function (e.g. the right hand side of equation 17) is analogous to the obtained image. Since the obtained image is dependent on Ø, the probability that a photon emitted by the given voxel is detected by the imaging equipment, the circuit function is a function of Ø. The RLC analogy can thus be used in order to determine the radiopharmaceutical input function, dV/dt, which optimizes Ø.

Possible forms for dV/dt include bolus injection (V(t) is a single pulse at t=0), constant drip (V(t) is a constant), and smart injection profile. Following are non-limiting examples of smart injection profiles:

1) Randomly (e.g. in the range of about every 1 to 200 sec)
2) Periodically every T seconds
3) Synchronized to the camera acquisition cycle. For example, if the camera produces a full volume scan every 5 seconds the injections are synchronized with each repetition of the scan. Synchronizing with camera acquisition allows better spatio-temporal coverage, as the injection and the scanning plans may be optimized together.
4) Synchronized to motion-related events. Motion-related events may include one or more of expiration, inspiration, cardiac movement, stomach contraction, gastro-intestinal movement, joint movement, organ movement, and so forth. For example, motion-synchronized injection may be used to inject and/or acquire during a relatively stable time period or a relatively motion-intensive time period.
5) Synchronized to physiological events (which may be acquired by another system). Physiological events may include a change in the activity of an organ or tissue (such as $O_2/CO_2$ concentration), glucose concentration, changes in perfusion, electrical activity (ECG, EMG, EEG, etc . . . ), neuronal activity, muscular activity, gland activity, and so forth.
6) Synchronized to an external event, for example to an external stimulation (e.g. by motion, sound, or light) or drug administration. Synchronizing with a drug administration may be useful for procedures such as imaging of cerebral perfusion events (like in functional MRI), so that a small bolus may be injected per stimulus and the region that uptakes the radiopharmaceutical will be more likely to be related to the stimulus.
7) Responsive to the radiopharmaceutical concentration in the blood. By monitoring the level of the radiopharmaceutical in the blood (either by drawing blood samples or by determining the level with the camera or other measurement system) it is possible to control the pattern in the blood, for example to keep a desired level, a desired slope, cycles, and so forth. In particular, when the frequency domain is used for the final analysis it may be beneficial to have the injection profile in one or more fixed periods (frequencies) selected to fit the expected kinetic profile, and to keep the concentration in the blood controlled so as to produce a desired spectral performance of the blood concentration, for example an approximately sinusoidal, saw-tooth, other harmonic form. When the level in the blood is provided by the camera, a closed loop system is obtained.

By synchronized to an event it is meant that the injection timing is substantially linked to the timing of the event; for example the injection is performed at the time of the event, at a predetermined delay after it, or at a predicted-time before the event. Such synchronization may allow summing and/or averaging the collected data in a synchronized fashion, similar to gating. Such summing/averaging enables the analysis and amplification of information related to the desired event, while all events which are not synchronized become "blurred", and have less influence on the final result. For example, an injection profile of once every two seconds allows data accumulated for a dynamic event synchronized to a two second period to be collected and averaged. External interferences, such as breathing, heart motion, and sudden patient motion, become less influential as they are not synchronized with the two second cycle. Therefore the signal to noise ratio and errors in the reconstructed kinetic parameters are reduced.

Reference is now made to FIG. 20, which is a simplified flowchart of a method for measuring kinetic parameters of a radiopharmaceutical in an organ of a body, according to a preferred embodiment of the present invention. The present method differs from the method of FIG. 15 in that it images a specific organ of the body. In step 6210, the radiopharmaceutical is administered to the body. In step 6220, the organ is imaged. In step 6230, a model is provided for obtaining kinetic parameters from the imaging is provided. Finally, in step 6240, the kinetic parameters are obtained by applying the measurements to the provided model and extracting the value of the required parameter(s).

A further preferred embodiment of the present invention is a drug formulation for a radiopharmaceutical.

Reference is now made to FIG. 21, which is a simplified flowchart of a process for obtaining the drug formulation, according to a preferred embodiment of the present invention. In step 6310, kinetic parameters for the radiopharmaceutical provided. In step 6320, the formulation is determined, based on the provided kinetic parameters. The values of the kinetic parameters are preferably obtained by the method of FIG. 15 described above.

In the above-described models C is modeled as a concentration. Alternatively, C may be modeled as a count rate. For each radiopharmaceutical there is a conversion ratio from concentration to count rate which depends on several factors. Factors influencing the conversion may include: mg of matter to number of molecules, the radiopharmaceutical half-life (which determines the average time for a photon to be emitted per molecule), and the rate of isotope decay. If the half-life is short, there is a reduction in available isotopes over the time of acquisition. Modeling the count rate may therefore be easier, and allow later conversion to concentrations.

Commonly, the time for a compound to become widespread in the body is in the time scale of about one minute. Thus the sharp slope in concentration observed immediately following injection lasts only a few seconds before various organs begin uptaking the compound. It is therefore preferable to allow scanning and reconstruction of volumes of interest in a time resolution of about 5-10 seconds. Since the model equations include relatively few parameters, it is assumed that with acquisition of a few minutes long (1, 2, 5, 10 minutes) the number of time points obtained per voxel is in the range of 10-20 (preferably 50 or more), which is expected to enable stable estimation of the kinetic parameters. With radiopharmaceuticals having slower uptake and release activity it may be preferred to have longer acquisition times, such as 20, 30, or 60 minutes.

The analysis and determination of parameter values may be performed in the time domain, the frequency domain, or in any other transform domain. In the time domain, analysis is performed by solving the differential equation, either analytically or numerically, in order to reach a model which best fits the acquired data. Various numerical tools are known to fit equations of this complexity to a given data set. An example of frequency domain analysis is presented below.

The analytical solution may include integration over the input Cg, which may not be available with sufficient accuracy. In such cases, numerical methods for fitting the differential equations may prove more stable and accurate.

It is expected that frequency domain analysis will be particularly effective when the data is acquired in a frequency representation. It is expected that time domain analysis will be particularly effective when the data is obtained over time. Alternative approaches may be tested by converting the data from one form to the other, and the more stable approach may be selected.

In some cases, the model above may further include interstitial volume, so that substances move from capillaries to the interstitial domain and from there to the cells, and vice versa. Transfer to and from the interstitial domain may be added to the equations. In many cases the difference in concentration between the interstitial volume and the capillaries is insignificant, thus they may be modeled as one domain.

It should be noted that the general blood concentration, Cg, may differ from one location to another, for example between veins and arteries. Therefore, it may be preferable to measure the blood concentration by a sample from the arteries or by measuring the concentration inside the left chambers of the heart.

Similarly, in the case of cardiac imaging there might be poor blood flow along one or more of the coronary arteries, and thus uptake of substance by cells in one voxel might reduce the remaining concentration in the artery available for voxels further along the given artery. Thus the value of Cg may actually be lower for the more distal voxels. Changes in the value of Cg may be handled by iterating the parameter estimation while correcting the Cg value once the uptake in the more proximal voxels has been estimated.

Note that if the radiopharmaceutical administration is based on a periodic injection protocol, the concentration in the general blood pool (either arterial or venous) may respond in a periodic pulsatile profile, which has a harmonic spectrum.

Following is a discussion of the application of frequency domain analysis to the above-described voxel dynamic modeling. Frequency domain analysis allows the use of techniques for measuring the frequency response to a periodic injection protocol, similarly to the way frequency response is evaluated in passive electrical circuitries. For example, the frequency response may be measured by injecting the radiopharmaceutical several frequencies, and then determining the amplitude of the response at a given frequency, the phase response, or the comparative amplitudes at several frequencies. The results are then compared with the model of the frequency response and parameters of interest are extracted (e.g. resistors and capacitor values in electrical circuitry, or diffusion coefficients and blood flow, F, in the voxel dynamic model).

Taking model 3 as an example, the Fourier transform equivalents of Equations 10-12 are:

$$C = (Ct*Vt + Cb*Vb)/V = Cb*Rb + Ct*(1-Rb) \quad (18)$$

$$jwCt = Kin \cdot Cb - Kout \cdot Ct \quad (19)$$

$$jwCb = F/Vb(Cg - Cb) - Kin \cdot Cb + Kout \cdot Ct \quad (20)$$

where C, Cb, Ct, Cg are in the frequency domain, w is the angular frequency, and j is the imaginary unit, $\sqrt{-1}$.

Equations 18-20 result in Equation 21, which relates the concentration in the voxel of interest (C) to the concentration in the arterial blood (Cg) in the frequency domain:

$$C = \frac{\frac{F \cdot Cg}{V}\left[\frac{Vt}{Vb} + \frac{jw + Kout}{Kin}\right]}{\left(jw + \frac{F}{Vb} + Kin\right) \cdot \left(\frac{jw + Kout}{Kin}\right) - Kout}$$

The relationship between C and Cg can be measured in several frequencies, enabling the extraction of F, Kin, and Kout.

Equation 21 is useful for analyzing the value of the kinetic parameters. Consider the case of w<<Kout, that is the case in which rate of clearance is much faster than the rates of changes in the blood flow. In practice, it is difficult to obtain w<<Kout for some radiopharmaceuticals, requiring slow and controlled changes in the blood concentration.

For w<<Kout, Equation 21 becomes:

$$\frac{C}{Cg} = \frac{\frac{F}{V}\left[\frac{Vt}{Vb} + \frac{Kout}{Kin}\right]}{\left(jw + \frac{F}{Vb}\right) \cdot \left(\frac{Kout}{Kin}\right)} = \frac{F}{V} \cdot \frac{\frac{Vt \cdot Kin}{Kout} + Vb}{jwVb + F} \quad (22)$$

Equation 22 provides a highly important relationship, as the ratio between two measurements, each with two different low frequencies w1 and w2 (i.e. two slow derivatives of concentration changes), provide a direct measure of flow rate:

$$\frac{\left(\frac{C}{Cg}\right)_2}{\left(\frac{C}{Cg}\right)_1} = \frac{jw_1 \cdot Vb + F}{jw_2 \cdot Vb + F} \quad (23)$$

The ability to isolate parameters, so that the values of different parameters do not affect each other, is of high importance. Parameter isolation combined with the high sensitivity and the ability to produce multiple repetitions in different frequencies or slopes may enable extracting some parameters in a quantitative and efficient manner.

Quantification in the case of w<<Kout depends on the prior estimation of the partial volume in each voxel containing the blood compartment. Once F is known, the ratio of Kin/Kout is obtainable from the Equation 22 above.

In a more typical scenario, w>>Kout, and equation 21 becomes:

$$\frac{C}{Cg} \cong \frac{F}{V} \cdot \frac{Kin \cdot Vt + jw \cdot Vb}{jw(jw \cdot Vb + Kin \cdot Vb + F)} \quad (24)$$

For w>>Kout, measuring the ratio of C/Cg in multiple frequencies allows the recovery of the flow F and the wash-in rate Kin (which is associated with the well being of the cells) in a quantitative manner.

It is possible to perform all analyses in terms of the absolute amplitudes of C and Cg by converting the modeling equations (which include complex numbers) to absolute numbers. Alternatively, phase analysis may be used. An additional alternative is to transform time-domain signals into the frequency domain with the Fourier transform, and to perform the remaining analysis in the frequency domain.

Expert System Basis

The following describes a method, based on imaging a patient using multiple kinetic parameters and measuring the distance between respective kinetic parameters, to relate the patient or individual voxels or groups of voxels to existing groups or populations, which are available in a database, thereby arriving at a decision, regarding the patient or individual voxels or groups of voxels. The existing populations in the database may be populations of generally healthy individuals, or are previous measurements of the same patient.

A platform is provided, which carries out a two-fold function in terms of three-dimensional images. First of all the platform sets up databases of parameter behavior from populations or from individuals and secondly it uses those databases to make inferences about a current image in light of knowledge from the databases. That is to say the platform decides which group in the database the current measurements most closely belong to. The body image obtains voxels and the voxels store multiple dimensional data therein. For example, a single voxel may store values of multiple parameters for a given location in the body and furthermore, for individual parameters, the voxel may store the time varying behavior of that parameter over the duration of the image.

The platform may then use the multiple dimensional data in the voxels to identify behavior, and decide on grouping, and an extension of the platform may make inferences or decisions as will be described in greater detail below. The grouping may identify pathology or tissue type or other group parameters as will be explained below and then the expert system may use rules to make decisions say about further treatment of the individual. Grouping may be of individual voxels to tissue types, or about groups of voxels as belonging to a particular tissues and/or pathology and/or organ, or about a pathology shown in the image as a whole.

In general, the different parameters in the voxel are not independent, since they all relate to the same tissue in the same person. Rather, certain parameters tend to correlate with one another. Thus if a certain parameter changes in a certain way we may expect, with a certain level of probability, that one of the other parameters will also behave in a certain way. Thus a healthy membrane regulates flow of any fluid, and an unhealthy membrane provides little regulation, so that a certain pathology would affect numerous flow parameters.

A scoring system can be used to decide if a pattern that emerges, for example, from the behavior of one or more parameters, indicates healthy tissue or fits a particular pathology. Alternatively, the scoring system can be used to decide what tissue type is being viewed.

More particularly, it is possible, given a matrix of voxels with multi-dimensional kinetic parameters representing a three-dimensional image scan over time, and similar matrices from a database, to define a covariance matrix between the two. The covariance matrix can be used to measure a statistical distance between the two matrices. The distance may be computed to numerous matrices in the database and the current scan can be assigned a parameter represented by the matrix to which it is closest. Thus, given a vector X of test K taken under condition L, the set may be found to be closest to a database set which represents subjects suffering from early symptoms of heart disease. It may therefore be assumed that the present patient is suffering from heart disease and the expert system may recommend a treatment regime. Alternatively the comparison may be with tissue types and particular voxels can be for tissue type, for example, heart tissue.

Certain tissues may, for example, be hard to distinguish. For example tumor tissue may look like muscular tissue under certain tests. In the event of such an ambiguity, a deciding test could be applied.

Reference is now made to FIG. 22, which illustrates a procedure for using a covariance matrix in the kind of platform described above in order to make inferences. As explained, a database is set up in stage 8000 to show existing data. The database is built up over time over different populations of patients or volunteers or for specific populations or even for the patient himself. The data sets are preferably normalized to give a standard presentation of the data so that they can be compared. Thus a reference average brightness value may be used or a reference orientation or a reference set of co-ordinates may be used, for example.

The database can be constructed using any combination of healthy volunteers and patients, who may be tested under different environmental situations, for example, physical stress, sensory stress, etc. Alternatively the database may comprise tests carried out on the patient himself using data taken at an earlier time, if such data is available.

The database may comprise matrices containing average results for identified groups, thus all persons under 25 undergoing environmental stress. Alternatively the separate results for individuals may be retained, each matrix being labeled with a group to which it is known to belong.

The database may be constructed on the basis of any one of numerous models to represent dynamic behavior as required. A standard interface allows all models to be used together. The dynamic model being used may be varied and, with it, the meanings of given parameters or the identities of the actual parameters being used may be varied. The different models may change the meanings of the different parameters in terms of the meanings of correlation of kinetic values to organ or tissue type, or to pathology or to test condition or to patient group.

The individual is imaged in stage 8002. The image is three-dimensional and typically extends for a finite amount of time. The results are stored in an array of voxels X^. Each voxel stores a range of parameters that the image was able to measure directly and the parameters may include the behavior of a variable of interest over a period of time, for example, the kinetic or K parameter for passage of a certain radiopharmaceutical (tracer) through a membrane. The imaging process essentially creates a map of tracer uptake and also of dynamic uptake parameters such as flow of the tracer across given boundaries.

The K parameter may vary, for example, depending on what kind of tissue is being examined, or the pathology present, and so may other parameters, so that from the behavior of a group of parameters it is possible to identify the tissue or pathology, provided that one has the mathematical tools to compare groups of multi-dimensional dynamic parameters. Referring now to FIG. 23, within a first tissue and/or a first pathology, two dynamic variables K1 and K2 may covary with a mean over time defined by line 8010 and a standard deviation defined by circle 8012. Similarly, the same pair of variables may have statistical behavior defined by mean 8014 and standard deviation 8016 when located within a second tissue or a second pathology.

It will be noted that there is a region of overlap between the two regions, so that unless the behavior of the variable is followed over time it may not be possible to determine clearly to which tissue type or pathology the current voxel or group of voxels belong. Only by following the dynamic behavior do the two cases resolve themselves as belonging to separate groups.

Returning now to FIG. 22, in stage 8004 a covariance matrix is calculated and used to provide a measure of the distance between a voxel or a group of voxels or the image results as a whole, and various groups existing in the prior data. As well as distance measurement, context information may be used. Thus the system may be constrained not to identify tissue types that are not relevant to the part of the body currently being imaged. For example an image of the abdominal cavity should not find brain tissue. An image of bone tissue may be expected to find the bone itself, as well as gristle, marrow and blood vessels. An image of muscle tissue may be expected to find blood vessels, nerves and ligaments, etc.

Context information may also include information from other types of imaging, such as CT images, MRI images, ultrasound images, and the like.

Context information may further include known data about the specific patient such as age, gender, etc. Thus the scan from a patient aged 65 or over need only be measured against groups relevant for that patient, and the scans for a pregnant female patient need only be compared against other pregnant female patients.

An image of heart tissue may determine flow parameters and the like and then the covariance matrix may be used to identify ischemic regions or regions of dead tissue. Dead tissue would probably show up as regions in which fluid flow through the membranes is not being regulated at all.

It is noted that the grouping system can be open or closed. In a closed group system the existing groups are regarded as the only available groups and the patient is assigned to the closest existing group no matter how unrelated it might be. In an open group system the patient is assigned to the closest group if he is within a certain distance therefrom but, if he is not within that distance, say further than two standard deviations from the group, then the patient is regarded as belonging in a group of his own.

Finally, in stage 8006, an expert system may use decision-making rules, based on the parameters found, in order to advise on a course of treatment, to make a diagnosis for the patient, or the like. Thus, for example, a rule may set thresholds of percentages of ischemic or dead tissue within the heart for different treatment regimes.

The expert system may accept data sheets for the tracers (radiopharmaceuticals) or may accept algorithms for scoring and rules for analysis, thus, as mentioned above, providing a way of measuring a probability that a particular set of readings fits a particular tissue, a particular disease, etc. The system may be constrained to check within a limited list of suspected diseases only or within anatomical constraints, that is, to take into account the region of the body being imaged or the known or expected shape or location of organs and the like. The data compared can be matched with the existing databases over various suspected pathologies or conditions. The data may include a kinetics value (K), as explained, and the rules may require matching of high level or derived criteria. The platform may match the measured behavior to the nearest scenario in the database. Alternatively it may do something beyond matching the nearest scenario in the database. For example, it may check ratios between values, ratios between different locations in the body, or ratios between takeup, it may check accumulation of different radiopharmaceuticals, among multi-time points, or among different tests, such as tests carried out under stress, rest, etc.

In the following description, a series of suitable parameters will be discussed, as will a series of environmental variables under which measurements may be made.

Parameters that are directly measurable from the image include kinetic flow rates through membranes, hereinafter K values. Also accumulation levels of a particular tracer in a region may be measured. It will be appreciated that the voxels are of the size range of millimeters whereas individual cells are much smaller, so the voxel is in any event showing only macro-behavior in the region. Actual behavior on the cellular level, say takeup of sugar in mitochondria, has to be inferred from the measured parameters.

Figure 24B:
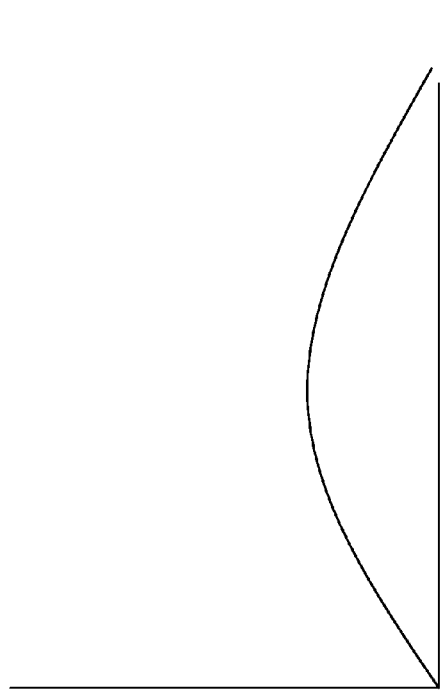
Figure 24D:
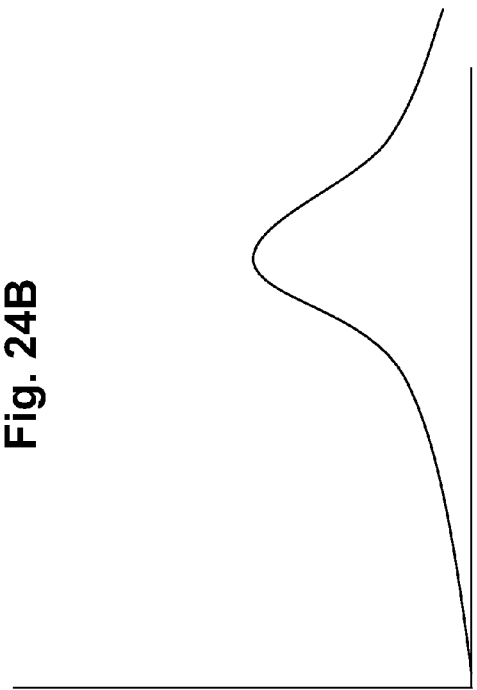
Figure 24A:
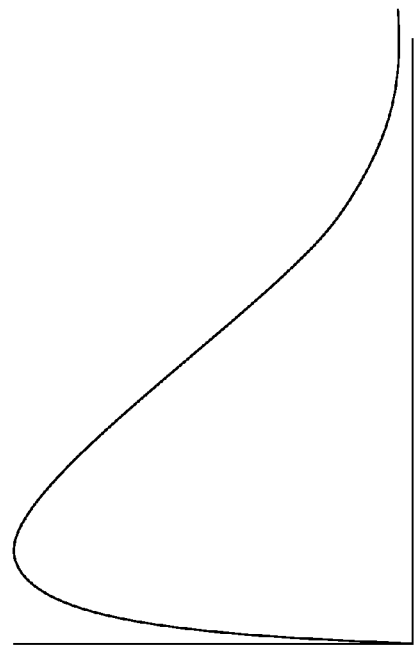
Figure 24C:
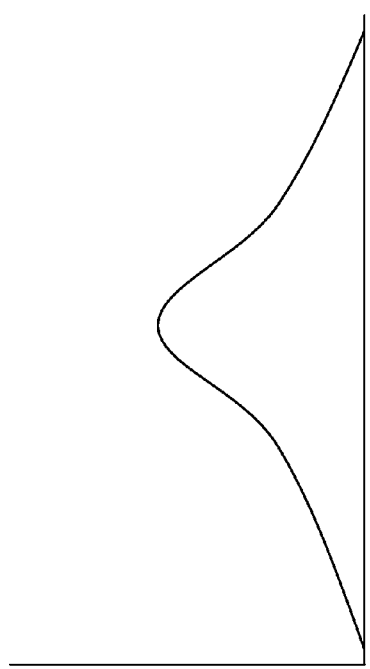

These values can be measured for one or more different tracers or pharmaceuticals and tend to have a behavior over time. FIGS. 24A ... 24D show behavior of K values for four different radiopharmaceuticals over time for a given tissue having a given pathology.

FIG. 25A illustrates accumulation of a tracer substance in a scarred tissue, where the membrane is not carrying out regulation. The substance simply enters and then leaves fairly rapidly and in an unregulated fashion. FIG. 25B by contrast illustrates accumulation of the tracer substance in a healthy tissue with an active membrane.

Another parameter that can be considered is glomerular filtration rate.

The parameters can be measured over time and under different conditions. Thus a person being imaged may be placed under physical stress, sensory stress, or the like, or may be exposed to a sensory event over the course of the image. Any given test is made under a single condition and the conditions are added as a label to the test, hereinafter L. Hence new graphs may be drawn of the behavior of a given parameter over the course of a particular event or whilst the patient is under a particular stress.

In the following, $\hat{X}$ represents a matrix resulting from an individual scan. A database $\tilde{X}$ is built of multiple scans taken under different conditions L, different pathologies j and for different tissues. The aim is that given a scan where one knows two of I, j, and L, one can use distance measurements against the database to determine the third.

The database $\tilde{X}$ preferably contains groups for all combinations of I, j and L that are of interest.

The initial scan is carried out on the patient in such a way that two of I, j and L are known, to obtain say $\hat{X}$ I,L.

Now each parameter in the measured scan has a kinetic behavior, including a mean and a standard deviation. Likewise any pair of parameters can have a covariance that has its own mean and standard deviation. Any individual measurement can be said to have a distance from this behavior measured in standard deviations from the mean. A series of measurements over time can be said to have a distance from behavior which is a summation of distances of the individual points.

This for a single parameter X, the distance may be given by $$\sigma^{-1}(X - \hat{X})$$

For the entire database, we measure distances $$\hat{\sigma}_{ikL}(\overline{X}_{i,I} - \tilde{X}_{i,k,l})$$

Then we find the closest group in the database to the current measurements and assign the missing label.

At this point reference is again made to the point above about open and closed groups. With a closed group system a definite allocation is made to the closest group. With an open group system an allocation is only made if the new scan is found to be within a predetermined threshold distance from an existing group from the database, say two standard deviations or one and a half standard deviations. Otherwise the new scan is assumed to be an independent group.

If the missing parameter is an organ or a tissue then the above procedure can identify which organ or tissue the voxel or group of voxels belongs to. If on the other hand the missing parameter is a pathology, then the entire scan or the group of voxels can be assigned a pathology.

Diagnosis in a Multidimentional Space

There is also provided in accordance with an exemplary embodiment of the invention, a method of diagnosis, comprising:

measuring a plurality of patient parameters to determine a patient state; and identifying a disease state by matching the patient state using a plurality of said plurality of parameters. Optionally, said patient state comprises a dynamic patient state.

In an exemplary embodiment of the invention, said patient state includes kinetic information of at least one biochemical at a temporal resolution of better than 1 second.

There is also provided in accordance with an exemplary embodiment of the invention, a method of acquiring a patient profile, comprising:

providing at least one material to a patient;

scanning an interaction of said material with the patient at a rate of over once a second; and building a complex profile of the patient including one or more of a kinetic profile of a parameter related to said material and a plurality of concurrently measured patient parameters.

In an exemplary embodiment of the invention, said building comprises building based on a previous estimated kinetic profile of the material.

There is also provided in accordance with an exemplary embodiment of the invention, apparatus for carrying out the methods described herein, comprising circuitry for said building.

There is also provided in accordance with an exemplary embodiment of the invention, a method of selecting a material for diagnosis, comprising:

estimating a patient physiological state in the form of a complex profile;

selecting a desired differentiation of patient state; and selecting a material to have an interaction with the patient which provides said differentiation. Optionally, said material is associated with a complex profile which is matched to said patient profile for said selecting.

There is also provided in accordance with an exemplary embodiment of the invention, a database comprising at least 20 substances, each one with a complex substance profile. Optionally, the database comprises at least 50 substances. Optionally, the database comprises at least 150 substances.

An aspect of some embodiments of the invention relates to a complex substance profile. In an exemplary embodiment of the invention, the profile includes intra-body location and/or tissue specific behavior, for example, metabolism and/or uptake. Optionally, the profile is of a time dependent parameter, such as change in metabolic rate over time. Optionally, static parameters, such as "expected effect" are provided and/or determined. In an exemplary embodiment of the invention, the profile includes an interaction of a substance with multiple physiological parameters, for example, parameters measured using methods and apparatus as described herein. In some embodiments, the profile includes an interaction or an effect on the behavior of the substance due to a previous physiological condition or perturbation, for example, the provision of another substance.

In an exemplary embodiment of the invention, the profile includes information on the behavior of a substance in short time frames, for example, tens of seconds, seconds, or fractions of seconds.

An aspect of some embodiments of the invention relates to considering a physiological state of a patient as a complex of multiple physiological parameters. In an exemplary embodiment of the invention, diagnosing a patient comprises identifying a patient's state in an N-space of parameters, optionally in on a relatively continuous scale. Optionally diagnosis is carried out by selecting a material which when applied to the patient will be affected in a noticeable manner dependent on the state of the patient. In an exemplary embodiment of the invention, the scale used for at least 3, at least 5, at least 10 or more or intermediate numbers of dimensions has at least 5, at least 10, at least 20, at least 40 or intermediate or higher numbers of meaningful levels. This is in contrast to typical medicine where usually a small number of threshold values is provided. Optionally, if the patient state is simplified, the simplification misrepresents less than 30%, less than 20%, less than 10%, less than 1% or intermediate percentages of the space, the space being sampled at uniform intervals.

In an exemplary embodiment of the invention, the physiological state of the patient is perturbated, for example by providing a substance, and diagnosis is based, at least in part, on the reaction of the physiological state to the perturbation.

An aspect of some embodiments of the invention relates to acquiring kinetic pharmacological information relating to a substance. In an exemplary embodiment of the invention, a portion of the body is scanned at a rate high enough to acquire kinetic information about the substance, for example, uptake, metabolism and/or physiological effect. In an exemplary embodiment of the invention, the information collected comprises an indication of patient kinetics. In an exemplary embodiment of the invention, the information collected comprises an interaction between the kinetics of a plurality of substances.

In an exemplary embodiment of the invention, the scanning comprises scanning using florescent imaging of fluorescently tagged materials.

Complex and/or Multi-Parameter Profiles

In the above section on an expert system, the use of some types of multi-parameter profiles has been described. In this section, inter alia, more general uses and/or profile types are described.

In an exemplary embodiment of the invention, the scanning system as described above is used to generate a complex profile of human physiology. Alternatively or additionally, a complex profile of substance is generated and/or used for diagnosis.

In an exemplary embodiment of the invention, the complex profile(s) includes pharmakinetic information at a relatively high temporal and/or tissue type resolution, for example, 10 seconds, 5 seconds, 1 second, 100 milliseconds, 50 milliseconds of faster or intermediate values. In an exemplary embodiment of the invention, the complex profiles are used to generate a diagnosis of patient state and/or define a suitable regime for treatment.

Exemplary Data System

FIG. 26 shows an exemplary configuration which may be useful for acquiring and/or using complex profiles, in accordance with some exemplary embodiments of the invention.

A scanner 20006, for example, as described above or any other type of fast scanner, for example a florescent imaging scanner that images fluorescently tagged materials or other scanners that image tagged materials or devices that track non-tagged materials, such as localized NMR (or other) spectroscopy or infra-red imaging, is used to acquire information about a patient 20002. Alternatively or additionally, genomic information, such as mRNA expression or protein expression is acquired, for example, using a gene chip. Alternatively or additionally to fast scanning, in some embodiments of the invention the scanning is relatively slow and/or maybe invasive, for example, blood tests, blood pressure and oxygenation measurement, mechanical measurements (e.g., ejection fraction) and/or any known physiological measurement. This information can include various physiological parameters of the patient and/or substances introduced therein, for example, substance concentration, metabolism, analyte levels, rates of change and/or fluid flow. Alternatively or additionally, the information comprises dynamic information, for example changes over time or changes in response to an action on the patient. Alternatively or additionally, the information comprises an association with particular body and/or tissue location information.

A controller 20004, optionally connected to scanner 20006, may be used to store, compare, analyze and/or otherwise use multi-parameter profiles and/or other complex profiles. Optionally, controller 20004 builds up a profile based on scanning results. A user input 20008, for example, a display and/or keyboard are optionally used to control controller 20004 and/or display results of controller 20004.

In an exemplary embodiment of the invention, the complex profile data is stored or organized in a tabular form, for example a multi-dimensional data table having, inter alia, some or all of the following dimensions:

(a) intrabody location, including, for example, tissue type and/or tissue location and/or including resolution level (e.g., cellular level, tissue level, organ level, body part level);

(b) diagnosic or body state definition;

(c) measured parameters, for example, biochemical concentrations (including blood analyte levels such as glucose and insulin) or aggregate measurements (e.g., blood pressure), which may include patient information, such as age and weight; and (d) state of patient, for example, at rest, standing, after mechanical stimulation and/or after administration of substance.

Coordinates (discrete or continuous) in the dimensions define cells which can include, for example, values of measured parameters, sets of parameters (e.g., a temporal series) and/or functional and/or statistical definitions of values and distributions.

This inter-relationship between various dimensions may be used to define a parameter space in which searching and/or other activities are carried on.

It should be appreciated that this data structure need not be stored as a table, even if its logical structure is that of a table. In particular, whole portions of the table may be blank (for lack of data and/or meaning), or be defined as a function or statistics. Alternatively or additionally, other data organization methods are used, which may use the above informational items as indexes of some type. In some cases, for at least some of the space, one or more dimensions and/or ranges of coordinates may be collapsed, for example, a range of states may be collapsed into a single meta-state. Such collapsing may also be carried out (e.g., temporarily) while viewing and/or analyzing the data.

It should be noted that a coordinate may include dynamic information, for example a series of absolute or relative changes over time, rather than a single value.

As will be described below, controller 20004 may relate to a patient complex profile 20010 (or more than one, for various situations). In an exemplary embodiment of the invention, complex profile 20010 includes a multi-parameter table 20012, at least one time dependent measurement 20016 and/or or at least one location dependent parameter 20014.

As will be described below, controller 20004 may relate to one or more substance complex profiles 20018. In an exemplary embodiment of the invention, complex profile 20018 can include a multi-parameter table 20026, intrabody-location dependent information 20024, substance description 20020 and/or additional information 20022. Optionally, the complex profiles define, for at least some points in the space, a trajectory defining the interaction of the substance (or other stimulus) with a patient located in that point in space. Optionally, the complex profile includes temporal information indicating different interactions at different time delays. Optionally, the complex profile defines cumulative interactions and/or transient interactions of a substance.

In addition, for example as described below, controller 20004 may include or be associated with an additional database defining positive and/or negative areas in the space. While a "goodness" value may be associated with some or all points in space, optionally, a set of areas that are desired patient states are defined as boundaries of areas.

While this description suggests that the controller is located at the scanner and patient, this is not necessarily the case. For example, for diagnosis, a controller may be located at a doctor's office, receive measurements and generate a diagnosis. Any one of the data sources and/or controller may be provided locally and/or remotely, depending on the implementation. In some cases, a simplified database is stored locally and a more complete database and/or processing algorithm is remote. In an exemplary embodiment of the invention, the data comprises one or more of patient data, clinic data, hospital data, healthcare system data, country data and/or international data, which are optionally accesses in a hierarchical manner and/or as slices relating to the patient.

Exemplary Process

FIG. 27 is a flowchart of a process of acquiring and/or using complex profiles in accordance with an exemplary embodiment of the invention. It should be appreciated that some embodiments of the invention involve practicing only parts of this process.

At 20102, a patient is scanned, for example using methods described above and/or using other means, for example invasive and/or non-invasive sensors as known in the art. In an exemplary embodiment of the invention, the scanning measures multiple physiological parameters of the patient, optionally organ and/or tissue specific. In an exemplary embodiment of the invention, at least one of the measured parameters is a biochemical parameter sampled at a high rate, for example, faster than once in ten seconds or once a second. In an exemplary embodiment of the invention, the sampling is made fast enough to provide useful information on a substance having a pharmakinetic behavior at those time scales.

At 20104, a patient profile is optionally generated, for example, by determining coordinates for the patient state in the above space. Optionally, the profile generated for the patient includes an uncertainty factor, which may be represented, for example, by indicating a cloud in the space with the density of the cloud depending on the certainty level of the determination.

In an exemplary embodiment of the invention, the space comprises at least 5, at least 10, at least 20, at least 30 or a smaller, intermediate or larger number of body area and/or tissue types.

In an exemplary embodiment of the invention, the space includes at least 2, at least 4, at least 10, at least 40, at least 100 or a smaller, intermediate or greater number of measured physiological parameters.

In an exemplary embodiment of the invention, the space includes at least 3 at least 10, at least 30 or a greater, smaller or intermediate number of patient classification data, such as height, genomic markers, race and/or age.

In an exemplary embodiment of the invention, time frames for temporal data includes at least 5 data points, at least 10 data points, at least 20 data points or a smaller, intermediate or greater number of points.

In an exemplary embodiment of the invention, a profile comprises a trajectory in space and may include the above number of points for temporal data.

In an exemplary embodiment of the invention, a similar process is used to generate a profile of a substance, by measuring its dynamic behavior in the above space (e.g., after application to the patient). For example, for a body tissue type/location, and other physiological parameters, the values of metabolism or uptake (depending on the measurement method) can be indicated as values in space. In an exemplary embodiment of the invention, the values are measured as a time series for a particular cell in the space. Alternatively or additionally, the correlation between the values and changes in the body state are tracked, for example, a substance may change in measured values as heart rate goes up, wherein each heart rate corresponds to a different point/cell in space. The change in heart rate may be induced. Optionally, for different conditions, different profiles of the substances are achieved, which profiles can be combined into a single complex profile that includes the condition as a dimension (e.g., standing, sleeping, sitting).

FIG. 28 shows a simplified two dimensional space 20202 for illustrating the results of scanning in accordance with an exemplary embodiment of the invention.

An area 20204 indicates a normatively healthy state encompassing a range of sets of values for the two (in practice possibly more) parameters. Optionally, improved health states are indicated by sub areas 20208 (of an area 20206) and 20210. In some cases, a disjoint health area exists, for example an area 20212 with an optional increased health area 20214. Optionally, each point in space is associated with a value indicating "health" that is functionally based on the coordinates and/or on observations.

In an exemplary embodiment of the invention, a non-health state is defined as any point outside of the marked "health areas. Optionally, however, one or more particular dangerous or unacceptable states 20216 are defined as well. In an exemplary embodiment of the invention, a degree of unhealth is defined as a distance between a point in space and a healthy area. Optionally, different diagnoses are associated with different distances and/or relative positions. Alternatively or additionally, diagnoses are associated with trajectories in space. Alternatively or additionally, a composite score is provided. Alternatively or additionally, the score depends on estimated quality of life, pain and/or risk.

A reference 20218 indicates a trajectory of a patient state in space. A plurality of momentary states 20222, 20224, 20226 and 20228 indicate a measurement of the patient state. As can be seen, the patient varies between points, in the example shown in a repetitive manner. In some cases, the behavior of the trajectory is chaotic, for example, with one or more attractors. Optionally, the morphology, position and/or time values for the trajectory are used for diagnosis. It should be noted that also healthy states can be defined as trajectories and/or otherwise be dynamic. Parameter values (e.g., blood glucose levels used as coordinates in space) can also be defined as a single point which indicates a distribution of values, statistical properties, attractors and/or a trajectory between values.

It should be noted that the health values may be obtained in various means, including, for example, based on the patient's own parameters and/or based on normative values collected for a population.

Also shown in FIG. 28 is a point 20230 which is nearly encompassed by a healthy area but is not part of the healthy area. In an exemplary embodiment of the invention, the diagnosis of the patient relates directly to the N-dimensional space (e.g., 20202) and not to dimensions of the space in a piecewise manner. As more specifically shown in a graph 20300 of FIG. 29, it is possible for a point 20304 to be outside of a healthy area 20302, while still being within the range values of projections of the area into lower dimension spaces. In typical diagnosis situations, one of two approaches is normally taken, either processing parameters one at a time or collapsing multiple parameters into a single measure. A BMI (body mass index) is an example of a composite measure which does not capture the intricacies of interaction between weight and height and completely ignores body form, metabolism, exercise level and other important parameters. Further, the "metabolic X syndrome" which is a composite of 5 (or so) measures, also simplifies the real space to avoid complexities. Further, in some cases there is a correlation between measured parameters. Typically, what is done is simply assume a fixed relationship 20306 and squander the information provided in area 20302. In a typical situation, relationship 20306 is realized as an area, for example, a rectangle and not a thin line.

In an exemplary embodiment of the invention, the use of a complex N-dimensional space (and optionally trajectories through space) and diagnosis based on simultaneous attention to multiple parameters enables such inclusions to be correctly identified. In an exemplary embodiment of the invention, the attention is given to at least 2, 3, 4, 5, 7, 10, 20, 50 or more or intermediate numbers of parameters.

In some embodiments, at least some of the dimensions are collapsed, at least for part of the diagnosis, for example, if there is missing measurement information or if the space is not populated with information.

In an exemplary embodiment of the invention, the acquired data is processed to help tease apart dependencies. Optionally, the processing indicates areas where two parameters are possibly less than perfectly correlated, which areas may benefit from additional measurement. While all the measurements are optionally acquired substantially simultaneously (e.g., in a time frame of less than 10 minutes, 1 minute, 10 seconds, 1 second or less), sequential acquisition may be practiced in some embodiments of the invention. In an exemplary embodiment of the invention, new disease states and/or types are defined based on identified points like point 20304 or based on trajectories.

In an exemplary embodiment of the invention, instead of providing a fixed diagnosis, for example "type II diabetes" the diagnosis relates to the actual degree of unhealth, for example, the distance (in some metric) from the nearest or a desirable normatively healthy area.

In an exemplary embodiment of the invention, the diagnosis takes into account not only the distance but also uncertainty factors, for example, uncertainties in measurements. A reference 20220 (FIG. 28) indicates a cloud of uncertainty relating to a measurement of point 20228.

Alternatively or additionally, the diagnosis takes into account the shape of the trajectory of the patient state (or monitored parameter value) and/or a spatial distribution and/or density of states and/or values (e.g., without tracking the ordinal relationship between points).

Referring back to FIG. 27, additional methods are contemplated. In one example, the patient is perturbated (20106), for example, by an impulse (e.g., a short exercise) or by a continuous activity (e.g., vasodilatation materials provision). In an exemplary embodiment of the invention, changes in patient state due to the perturbation and/or caused by the perturbation (e.g., to one or more measured parameters), are tracked (20108). It should be noted that the perturbation will generally cause a change in patient state. Optionally, the trajectory of the change and/or distribution of state points are used to fine tune a diagnosis (20112) of the patient. Alternatively or additionally, the perturbation is used to generate a more complex profile for the substance being tracked, for example by showing values for other conditions. Alternatively or additionally, the perturbation can provide a set of measurements which may reduce the uncertainty of measurement for a single patient state. Alternatively or additionally, the perturbation shows the stability of the patient in his physiological state and/or initiates a trajectory in space, either or both of which may be used as a means for diagnosis, for example by comparing against norms. Alternatively or additionally, the perturbation is used to generate a kinetic profile of the patient and/or a substance (20110).

In a particular example, perturbation comprises administering another substance. The measured values can include, for example, the interaction between the substances (e.g., effect of ability to measure), effect of one or both substances on the physiological state and/or values for one or both substances as the physiological state changes due to the other or both substances.

In another method, once a patient profile is known, a tracer material is selected to (20114) so as to provide differentiation for what the profile shows in a later scan (20116). In particular, a tracer which will not be absorbed due to patient state need not be used. Similarly, the tracer is optionally selected and/or formulated so as to meet both data acquisition limitations and need to generate a measurable difference. Optionally, this selection is based on a profile associated with the material. Optionally, a database of materials and complex profiles is stored. In one example, if there is a problem that can be metabolic or absorption based, a tracer affected mainly by metabolism will be useless for absorption problems. Thus by first determining what the underlying problem is, a tracer and/or scanning protocol that will provide useful information on the metabolic (or absorption) problem, can be selected In another method, the patient is scanned with a material having a known complex profile. By comparing (20118) the actual results to anticipated results, a physiological model of the patient may be extracted and/or identified. In an exemplary embodiment of the invention, the model is found by searching the space of patient profile for a profile that acts in a manner similar to the observed manner. In another example, a mathematical model that links the measured parameters to the known profile and/or kinetics is generated and/or tuned.

It should be appreciated that the dimensions of the patient profile space and the material profile space need not match perfectly. Optionally, a mapping function between dimensions is provided by a user.

In an exemplary embodiment of the invention, diagnosis uses an expert system, for example a rule based system or a neural network. In lower-dimension cases, a visual method is optionally used.

In an exemplary embodiment of the invention, the patient profile space is used to store data about all patients and patient types. Optionally, the space is updated continuously as more data is acquired. Optionally, studies, as carried out, are combined into the space to populate empty spaces and/or reduce uncertainty in existing spaces. As new information about studies surfaces, the data may be reintegrated into the space. Optionally, when a patient profile and/or material profile are missing, these may be interpolated from existing data. Optionally, an expert (e.g., human) opinion is provided, for example, to suggest relevant data to be interpolated between and/or weights. In an exemplary embodiment of the invention, a user can input constraints that prevent a diagnosis from extending in the direction of certain coordinate values. Alternatively or additionally, such constrains can be used to guide a diagnosis process, including a step-by-step diagnosis process.

In an exemplary embodiment of the invention, health definitions are provided based on an asymptomatic population and/or time in a patient's life. Alternatively or additionally, health and/or unhealth areas are at least partially defined based on accepted allowed ranges and/or risk-indicating values.

Molecular Imaging—

Sensitivity by the Radioactive-Emission Camera of the Present Invention.

The purpose of this calculation is to estimate the minimal isotope concentration in a tissue for obtaining absolute measurement of a target molecule concentration, for high quality molecular imaging.

Photons detection capability

The radioactive-emission camera of the present invention is capable of detecting about $1/1500$ of the emitted photons with energy resolution of 5%, without setting the scanning to a region of interest (full chest scan). By opening the energy window to about 15% and targeting the scanning to the region of interest, the camera is capable to detect about one photon out of every 200-500 photons emitted form the tissue. Additional steps will be implemented in the future to reach $1/100$ and better.

For the sake of this analysis, $1/1000$ is taken as the photon detection capability.

Quality requirement: minimum of 200 counts per voxel

Expected inaccuracies:
  About 7% due to Poisson distribution (D200/200)
  About 5% due to uniformity limits and other reconstruction noise
  Target to background of 3:1 can still be observed in high quality Imaging time: 20 ml (1200 sec)

Voxel size: about 4-5 mm ⇒ 0.1 cc

Minimum photon emission rate per cc, is thus:

200 counts/1200 sec/($1/1000$ sensitivity)/0.1 cc=$1.6 \times 10^3$ p/s/cc=$4.5 \times 10^{-8}$ Ci/cc For $^{99m}$Tc, the half life is about 6 hours (21600 sec), thus the required minimal number of $^{99m}$Tc atoms per cc is:

$1.6 \times 10^3 \times 21600/\ln(2) = 5 \times 10^7$ (# of $^{99m}$Tc atoms/cc)

Or $5 \times 10^7/(6.2 \times 10^{23}) = 8 \times 10^{-17}$ moles of $^{99m}$Tc/cc For $^{111}$In, the half life is about 70 hours (250000 sec), thus the required minimal number of $^{99m}$Tc atoms per cc is:

$1.6 \times 10^3 \times 250000/\ln(2) = 6 \times 10^8$ (# of $^{111}$In atoms/cc)

Or $6 \times 10^8/(6.2 \times 10^{23}) = 9.6 \times 10^{-16}$ moles of $^{111}$In/cc These numbers defines the camera sensitivity.

The camera sensitivity can be used per application to determine minimum measured concentration of target molecules (proteins, mRNA) by taking into account the ratio of binding the $^{99m}$Tc or $^{111}$In to the antibody (which can be relatively high with $^{99m}$Tc or $^{111}$In) and the fraction of the target molecules bound by the antibody (e.g. 10-15%).

Both $^{99m}$Tc and $^{111}$In may be convenient as they allow proper preparation time (to obtain high specific activity) and uptake time by the tissue. While in PET, typical specific activity is in the range of 1,000 Ci/mmole, the SPECT specific activity is expected to be about 10,000 Ci/mmole.

For $^{99m}$Tc (half life of 21000 sec), the minimum number of target molecules per cc (N) is calculated as follows:

$N$ (target molecules/cc)×15% [binding]×10,000 Ci/mmole [$S.A.$]=4.5×10$^{-8}$ Ci/cc $N$=4.5×10$^{-8}$ Ci/cc/15%/10$^7$ Ci/mole=3×10$^{-14}$ moles/cc=3×10$^{-11}$ Molar

EXAMPLES

The following are nonlimiting examples for better illustrating embodiments of the present invention.

Example 1

In accordance with an embodiment of the present invention, a cardiac vulnerable-plaque and myocardial-perfusion protocol is employed, for two purposes:

i. identify plaques that may be released into the blood stream; and
ii. evaluate the extent of perfusion defect, if any, caused by the plaque.

The cardiac vulnerable-plaque and myocardial-perfusion protocol is carried out as follows: A patient is injected with up to about 5 mCi of Annexin radiopharmaceutical labeled with 111-In. After about 24 hours, the patient is injected with up to about 5 mCi of AccuTec radiopharmaceutical labeled with Tc-99m. After the AccuTec injection, the patient is subjected to a pharmacological stress, for example, by the administration of adenosine. At peak vasodialation, the patient is injected with up to about 1 mCi Tl-201 thallous chloride. Immediately following the Tl-201 thallous chloride injection, dynamic imaging is carried out for up to 30 minutes.

The AccuTec binds to activated platelets and shows thrombus. The Annexin binds to apoptotic cells—human neutrophils that have died and broken up, demonstrating inflammatory infiltrate.

This protocol facilitates the study of dynamic plaques, associated with cardiac plaque tissue damage and repair. By employing this multi-isotope protocol, it is possible to identify vulnerable plaque and the extent of myocardial perfusion defect, indicative of some degree of stenosis, which results from the plaque.

Quantitative Analysis:

The quantitative results are described using the following acronyms.
i. Coronary Flow Reserve—CFR;
ii. Left Anterior Descending—LAD;
iii. Right Circumflex—CR;
iv. Value Circumflex—CX;
v. Descending Circumflex—CD.

Normal Conditions:
CFR Velocity at peak vasodilation/Velocity at baseline—3.07±0.92.

Ischemic Heart Conditions:
LAD value 1.84±0.43
LAD/RC value 1.85±0.52
LAD/CX value 2.02±0.64
Cx or CD value 2.41±0.58
Three-vessel Descending 1.89±0.41
X-syndrome 1.41±0.33

Aortic grades of atherosclerosis caused by plaque will be determined by the intensity of Accutec (inflammation) and Annexin uptake apoptosis also for plaque and will be given grades 0-2, as seen in the Aortic-Grade Table, below.

Aortic-Grade Table

| Intensity of Accutec & Annexin | Aortic Grades | mean CFR |
|---|---|---|
| low | 0 | 2.32 ± 0.77 |
| medium | 1 | 1.91 ± 0.67 |
| high | 2 | 1.90 ± 0.78 |

Analysis:
When the CFR Velocity at peak vasodilation/Velocity at baseline is less than 2.5, an aortic grate of 1-2 will be expected. When that is not the case, another source for the low CFR value has to be identified, for example, X-syndrome.

Example 2

The effect of acetazolamide (Diamox) used for treatment of disorders such as epilepsy by controlling fluid secretion may be tested by using Tc-99m-HMPAO or Tc-99m-Ceretec for quantitative measurements of regional cerebral blood flow (rCBF). Patients will be administered Diamox and after sufficient time for the drug to take effect, the patient will be injected with up to 30 mCi of HMPAO or Ceretec. Immediately following the injection, the patient will be imaged for 30 minutes with a dynamic imaging protocol. The time of maximal rCBF increase is estimated to be at 15 minute post injection 1 g of Diamox. The rCBF increases from 58±8 at rest to 73±5 ml/100 g/min. In normals with relatively low rCBF values at rest, Diamox increases the reserve capacity much more than in normals with high rCBF values before provocation. It can be expected that this concept of measuring rCBF at rest and the reserve capacity will increase the sensitivity of distinguishing patients with reversible cerebrovascular disease (even bilateral) from normals. Essentially, the bigger the difference in values, the better, as seen in the table below.

rCBF values

| | rCBF values at rest | rCBF values at rest with 1 g Diamox dose |
|---|---|---|
| Normal population | 58 ± 8 at rest | 73 ± 5 ml/100 g/min. |
| patients with reversible cerebrovascular disease | 58 ± 8 at rest | <73 ± 5 ml/100 g/min. |
| patients with irreversible cerebrovascular disease | 58 ± 8 at rest | <60 ± 5 ml/100 g/min. |

Example 3

Figures 10H, 10I, 10J:
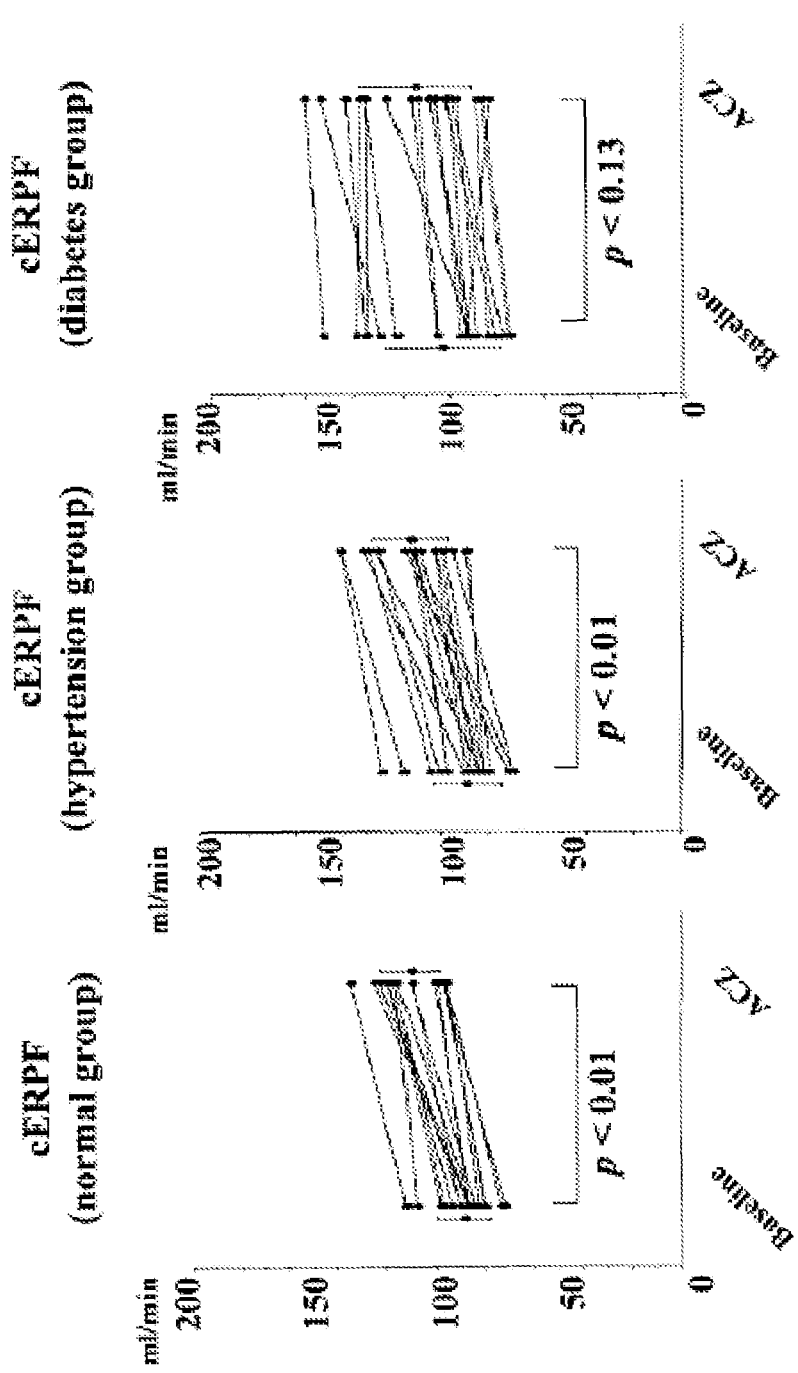

This example relates to FIGS. 10H-10J.

Tc-99m-MAG3 renography can differentiate the severity of renal angiopathy in patients with Type 2 diabetes through the depletion of renal vasoreactivity after an intravenous injection of acetazolamide (ACZ). Patients will be administered ACZ and after sufficient time for the drug to take effect, the patient will be injected with up to 30 mCi of MAG3Tc99m. Immediately following the injection, the patient will be imaged for 30 minutes with a dynamic imaging protocol to determine the renal perfusion flow. Values of effective renal plasma flow (ERPF) significantly differ between the baseline and the ACZ, both for the normal group and for hypertension group, both having p<0.01 However, for the diabetes group values are distinctly different from the other two groups, with p<0.13.

Example 4

The following simultaneous, dual-isotope protocol for perfusion and fatty-acid metabolism is expected to be of great clinical importance. It employs I-123-BMIPP, a fatty acid radiopharmaceutical, which has been clinically available in Japan for many years, and which is currently undergoing Phase III clinical trials in the United States. Simultaneous imaging for myocardial perfusion, with any one of Tc-99m sestamibi, Tc-99m tetrofosmin, or Tl-201 thallous chloride, and for fatty acid metabolism with I-123-BMIPP will provide a disease signature for ischemic syndromes and therefore promises to be of importance in assessing patients with suspected acute ischemic syndromes and a variety of other conditions.

If a patient arrives at an emergency room immediately after a cardiac event (myocardial infarct), a definitive diagnosis may be made by the above study. A standard myocardial perfusion study may not yet show any ischemic effects, but the BMIPP scan will demonstrate the first stages of ischemia as a cold region.

Example 5

This example is shown in reference to FIG. 10A. Kidney studies are carried out to determine the status of kidney function. By studying the kidney filtration, it is possible to identify obstruction, or blockage, in the collecting system and have a good indication of overall renal function. There are two types of kidney filtration and two different studies to evaluate them. One is glomerular function and the other is tubular function, and both work in tandem. The kidney is designed to flush out impurities, but not all of the fluids. This is accomplished by concentration gradients, which maintain fluids in the system but remove the waste. One phase works a bit slower than the other, but allows the kidney to remove toxic products effectively. In many renal diseases, one of the first things that disappears or diminishes is the tubular function.

Candidates for a kidney nuclear medicine scan are patients who have renal failure or chronic renal failure, obstruction in their urine collection systems, renal artery stenosis, or a kidney transplant.

By measuring the kinetics of uptake and washout of Tc-99m-MAG3 together with other tracers such as 111-In-DTPA from the kidney it is possible to obtain absolute flow values in the kidney, such as tubular excretion rate and glomerular filtration rate simultaneously. In general, a patient may be injected about 1 mCi of 111-In-DTPA and 10 mCi of Tc-MAG3, with the camera running, and imaging is begun immediately. Imaging is taken for a time of up to 10 minutes, with an energy window of between 3 and 15%. These values may be combined into disease signatures for a variety of kidney pathologies, resulting in more accurate diagnosis and overall better patient care.

Example 6

This example is illustrated with reference to FIGS. 10C-10E. Following a coronary bypass surgery, a patient is administered Ga-67, aimed at detecting inflammations. About 24 hours later, the patient is administered Tc-99m-HDP, directed at bone scans and Tc-99m-sestamibi, directed at myocardial perfusion. Within about 2-5 minutes of the injection of Tc-99m-HDP and Tc-99m-sestamibi, dynamic cardiac imaging is performed at rest (and under stress, as required), to identify possible osteomyelitis in the sternum, by Tc-99m-HDP, possible inflammation in the mediastinum by the Ga-67, and to evaluate the myocardial perfusion, by the Tc-99m-sestamibi.

Example 7

Radiopharmaceutical combinations are exemplified by liver-spleen scan+RBC+gallium (for cases of liver SOL/hemangioma/abscess/hepatoma).

Applications

Applications of the present invention relate to a method of image reconstruction of a multi-isotope source, comprising:

modeling photon scatter for each isotope j, based on the Compton scatter equation, relating initial and final photon energies to a Compton scatter angle;

employing an iterative process for generating a solution for the image reconstruction, by describing a probability that an emitted photon of an isotope j, from a voxel u, be detected by a detector t, at an energy bin b.

Another application of the present invention relates to a method for determining a future administration dose, comprising:

i. administering a radiopharmaceutical at no more than one fifth of an expected effective dose;

ii. measuring by SPECT the distribution of the radiopharmaceutical in the body; and iii. determining the preferred administration dose of the radiopharmaceutical agent for at least one future administration.

The future administration may be a radiopharmaceutical or a therapeutic agent.

Another application of the present invention relates to a method of diagnosing a patient condition, comprising:

defining pathological signatures, each characterized by a unique combination of at least two parameters, which relate to behavior of a radiopharmaceutical in vivo;

measuring the at least two parameters, for a patient, by SPECT imaging; and automatically diagnosing a pathology of the patient, by automatically matching the at least two parameters and the pathological signatures.

Another application of the present invention relates to a method of diagnosing a patient condition, comprising:

defining pathological signatures, each characterized by a unique combination of at least two patient parameters, at least one of which relating to behavior of a radiopharmaceutical in vivo;

measuring the at least two patient parameters, wherein the at least one patient parameter relating to the behavior of the radiopharmaceutical in vivo is measured by SPECT imaging—the other may be for example, EKG, blood pressure or the like; and automatically diagnosing a pathology by automatically matching the at least two patient parameters and the pathological signatures.

The automatically diagnosing a pathology may be based on a database of values for normal and diseased populations.

Additionally, it may be based on a measurement of at least one radiopharmaceutical kinetic parameter of a flow rate across a tissue membrane.

Additionally, it may include automatically determining the degree of the pathology, for example, analogous to degrees of burns, for example.

Another application of the present invention relates to an electronic storage medium comprising:
- at least one radiopharmaceutical identity;
- SPECT measured values of at least one radiopharmaceutical kinetic parameter of a flow rate across a tissue membrane, for the radiopharmaceutical, and
- a set of instructions for associating the at least one radiopharmaceutical kinetic parameter with a disease signature.

Another application of the present invention relates to an electronic storage medium comprising:
- defining pathological signatures, each characterized by a unique combination of at least two patient parameters, at least one of which relating to behavior of a radiopharmaceutical in vivo, as measured by SPECT;
- measuring the at least two patient parameters, wherein the at least one patient parameter relating to the behavior of the radiopharmaceutical in vivo is measured by SPECT imaging; and
- automatically diagnosing a pathology by automatically matching the at least two patient parameters and the pathological signatures.

Protocols

Protocols in accordance with the present invention are described in FIGS. 30-38.

Protocols for Fast Cardiac Imaging

The following cardiac imaging protocols include two imaging stages, at rest and after stress. Generally, they are performed with gating and attenuation corrections.

1. A fast, dual-isotope, imaging protocol: For imaging at rest, a patient is injected with about 3 mCi of Tl-201-thallous chloride, some time prior to the imaging, while remaining substantially at rest. After a waiting period of 10-15 minutes, a rest imaging of about 2 minutes is taken. The patient is then subject to a physical stress, for example by exercising on a treadmill. At the peak stress level, the patient is injected with about 20-30 mCi of Tc-99m-sestamibi. After a waiting period of about 30-60 minutes, a post-stress imaging of about 2 minutes is taken. The total imaging time of this protocol is about 4 minutes, and the total patient time is about 60-90 minutes. The advantage of this protocol is in the fast imaging time, of about 2 minutes per image, when compared to standard imaging methods.

2. A fast, single-isotope, imaging protocol: For imaging at rest, the patient is injected with about 8-10 mCi of Tc-99m-sestamibi, some time prior to the imaging, while remaining substantially at rest. After a waiting period of about 30 minutes, a rest imaging of about 2 minutes is taken. The patient is then subject to a physical stress, for example by exercising on a treadmill. At the peak stress level, the patient is injected with about 20-30 mCi of Tc-99m-sestamibi. After a waiting period of about 30-60 minutes, a post-stress imaging of about 2 minutes is taken. The total imaging time of this protocol is about 4 minutes, and the total patient time is about 60-90 minutes. The advantage of this protocol is in the fast imaging time, of about 2 minutes per image, when compared to standard imaging methods.

3. An ultra fast, dual-isotope, imaging protocol: For imaging at rest, the patient is injected with about 3 mCi of Tl-201-thallous chloride, some time prior to the imaging, while remaining substantially at rest. After a waiting period of about 2 minutes, a rest imaging of about 2 minutes is taken. The patient is then subject to a pharmacological stress, for example, for example, by the administration of adenosine. At the peak stress level, the patient is injected with about 20-30 mCi of Tc-99m-sestamibi, while positioned under the camera. Substantially immediately after the second injection, a post-stress imaging of about 2 minutes is taken. The total imaging time of this protocol is about 4 minutes, and the total patient time is about 20-30 minutes. The advantage of this protocol is in the fast imaging time, of about four minutes, and in the avoidance of liver radioactivity, since imaging takes place substantially immediately after injection, before buildup of radioactivity in the liver takes place.

4. An ultra fast, single-isotope, imaging protocol: For imaging at rest, the patient is injected with about 8-10 mCi of Tc-99m-sestamibi, some time prior to the imaging, while remaining substantially at rest. Substantially immediately after the injection a rest imaging of about 2 minutes is taken. The patient is then subject to a pharmacological stress, for example, by the administration of adenosine. At the peak stress level, the patient is injected with about 20-30 mCi of Tc-99m-sestamibi, while positioned under the camera. Substantially immediately after the second injection, a post-stress imaging of about 2 minutes is taken. The total imaging time of this protocol is about 4 minutes, and the total patient time is about 20-30 minutes. The advantage of this protocol is in the fast imaging time, of about two minutes, and in the avoidance of liver radioactivity, as in protocol 3.

5. A dual-isotope, simultaneous imaging protocol: The patient is injected with about 3 mCi of Tl-201-thallous chloride, and after a waiting period of about 15 minutes' proceeds to a treadmill. At the peak stress level, the patient is injected with about 20-30 mCi of Tc-99m-sestamibi. After a waiting period of about 30-60 minutes a simultaneous imaging of about 2 minutes is taken. The total imaging time of this protocol is about 2 minutes, and the total patient time is about 45-90 minutes. The advantage of this protocol is in the fast imaging time, of about 2 minutes of single acquisition, and more important, in the dual registration of the two isotopes, when imaged simultaneously.

6. A fast, dual-isotope, thallium-stress-perfusion, imaging protocol: For imaging at rest, the patient is injected with about 3 mCi of Tc-99m-sestamibi, some time prior to the imaging, while remaining substantially at rest. After a waiting period of about 15-30 minutes, a rest imaging of about 2 minutes is taken. The patient is then subject to a physical stress, for example by exercising on a treadmill. At the peak stress level, the patient is injected with about 3 mCi of Tl-201-thallous chloride. After a waiting period of about 10-15 minutes, a post-stress imaging of about 4 minutes is taken. The total imaging time of this protocol is about 6 minutes, and the total patient time is about 45-60 minutes. The patient may then be re-imaged after 4 hours during which the Tl-201-thallous chloride has had time to redistribute to determine viability. The advantage of this protocol is in the fast imaging time, of about 2-4 minutes per image, and in the better flow linearity, the ability to detect small lesions, and determine viability.

7. A fast, dual-isotope, thallium-stress-perfusion, imaging protocol: For imaging at rest, the patient is injected with about 3 mCi of Tc-99m-sestamibi, some time prior to the imaging, while remaining substantially at rest. After a waiting period of about 15-30 minutes, a rest imaging of about 2 minutes is taken. The patient is then subject to a pharmacological stress, for example, by the administration of adenosine. At the peak stress level, the patient is injected with about 3 mCi of Tl-201-thallous chloride, while positioned under the camera. Substantially immediately after the second injection, a post-stress imaging of about 4 minutes is taken. The patient may then be re-imaged after 4 hours during which the Tl-201-thallous chloride has had time to redistribute to determine viability. The total imaging time of this protocol is about 6 minutes, and the total patient time is about 20-30 minutes (additional four hours for re-distribution). The advantage of this protocol is in the fast imaging time, of about 6 minutes per image, and in the better flow linearity, the ability to detect small lesions, and viability.

8. An ultra fast, dual-isotope, thallium-stress-perfusion, imaging protocol: For imaging at rest, the patient is injected with about 3 mCi of Tc-99m-sestamibi, and rest imaging of about 2 minutes is taken, with substantially no waiting period. The patient is then subject to a pharmacological stress, for example, by the administration of adenosine. At the peak stress level, the patient is injected with about 3 mCi of Tl-201-thallous chloride, while positioned under the camera. Substantially immediately after the second injection, a post-stress imaging of about 4 minutes is taken. The patient may then be re-imaged after 4 hours during which the Tl-201-thallous chloride has had time to redistribute to determine viability. The total imaging time of this protocol is about 6 minutes, and the total patient time is about 10-20 minutes (additional four hours for re-distribution). The advantage of this protocol is in the fast imaging time, of about 6 minutes per image, in the better flow linearity, the ability to detect small lesions, and viability, the single acquisition, and more important, the dual registration of the two isotopes, when imaged simultaneously.

9. A fast, dual-isotope, simultaneous imaging protocol: For imaging at rest, the patient is injected with about 3 mCi of Tc-99m-sestamibi, some time prior to the imaging, while remaining substantially at rest. After a waiting period of about 30 minutes, a rest imaging of about 2 minutes is taken. The patient is then subject to a pharmacological stress, for example, by the administration of adenosine. At the peak stress level, the patient is injected with about 3 mCi of Tl-201-thallous chloride. After a waiting period of about 2 minutes, a post-stress imaging of about 4 minutes is taken. The total imaging time of this protocol is about 6 minutes, and the total patient time is about 10-20 minutes (additional four hours for re-distribution). The advantage of this protocol is in the single imaging time, of about 6 minutes per image, and in the better flow linearity, the ability to detect small lesions, and the relatively high viability.

10. A fast, single-isotope, Tc-99m-teboroxime imaging protocol: For imaging at rest, a patient is injected with about 8-10 mCi of Tc-99m-teboroxime, while the patient is under the camera, and a rest imaging of about 2-10 minutes is taken. The patient is then subject to a pharmacological stress, for example, by the administration of adenosine. At the peak stress level, the patient is injected with about 20-30 mCi of teboroxime, while positioned under the camera. Substantially immediately after the second injection, a post-stress imaging of about 2-10 minutes is taken. The total imaging time of this protocol is about 12 minutes, and the total patient time is about 20 minutes.

Protocols for Fast General Imaging

11. Lung V/P-DTPA aerosol and macro-aggregated albumin (lung perfusion agent) protocol, for studying lung perfusion by quantitative parameters, such as ml/min/gr, using Tc-99m-Macre aggregated albumin and Tc-99m DTPA (up to 5 mCi), MAA up to 5 mCi (up to 1M particles), with immediate acquisition immediately after DTPA, with MAA in injected and the immediate acquisition, using an energy window of between 3 and 15%. The advantage—fast 12. Fast MDP (medronate)-bone scan-whole body scan protocol, routinely performed to look for bone tumors or inflammatory processes of the bone (e.g. osteomyelitis), with an acquisition time of up to 6 minutes, using Tc-99m-MDP, at 20-30 mCi total dose, with a waiting period of 0-60 minutes, energy window—anywhere between 3-15%, advantage—fast.

13. In 111-WBC is used to image inflammatory processes at 2-3 mCi total dose, with a waiting period of 24 hrs and an acquisition time of up to 1 minute, energy window—anywhere between 3-15%, advantage—fast.

Protocols for Low-Dose Cardiac Imaging

The following cardiac imaging protocols include two imaging stages, at rest and after stress.

14. A low-dose, dual-isotope, imaging protocol: For imaging at rest, a patient is injected with about 0.3 mCi of Tl-201-thallous chloride, some time prior to the imaging, while remaining substantially at rest. After a waiting period of 10-15 minutes, a rest imaging of about 15 minutes is taken. The patient is then subject to a physical stress, for example by exercising on a treadmill. At the peak stress level, the patient is injected with about 3 mCi of Tc-99m-sestamibi. After a waiting period of about 30-60 minutes, a post-stress imaging of about 15 minutes is taken. The total imaging time of this protocol is about 25-30 minutes, and the total patient time is about 90 minutes. The energy window is between 3 and 15%. The advantage of this protocol is in the low dose, and the better spectral resolution that results from it.

15. A low-dose, single-isotope, imaging protocol: For imaging at rest, a patient is injected with about 0.3 mCi of Tc-99m-sestamibi, some time prior to the imaging, while remaining substantially at rest. After a waiting period of about 15-30 minutes, a rest imaging of about 15 minutes is taken. The patient is then subject to a physical stress, for example by exercising on a treadmill. At the peak stress level, the patient is injected with about 3 mCi of Tc-99m-sestamibi. After a waiting period of about 30-60 minutes, a post-stress imaging of about 15 minutes is taken. The total imaging time of this protocol is about 25-30 minutes, and the total patient time is about 90 minutes. The energy window is between 3 and 15%. The advantage of this protocol is in the low dose, and the better spectral resolution that results from it.

16. A low-dose, dual-isotope, simultaneous imaging protocol: The patient is injected with about 0.3 mCi of Tl-201-thallous chloride and then subject to a physical stress, for example by exercising on a treadmill. At the peak stress level, the patient is injected with about 3-5 mCi of Tc-99m-sestamibi. After a waiting period of about 30-60 minutes, a simultaneous rest and post-stress imaging of about 5-15 minutes is taken. The total imaging time of this protocol is about 20-30 minutes, and the total patient time is about 90 minutes. The energy window is between 3 and 15%. The advantage of this protocol is in the low dose, better image registration, and better spectral resolution.

17. A low-dose, dual-isotope, fast imaging protocol: For imaging at rest, the patient is injected with about 0.3 mCi of Th-201-thallous chloride, while under the camera. After a waiting period of about 2 minutes, a rest imaging of about 15 minutes is taken. The patient is then subject to a pharmacological stress, for example, by the administration of adenosine. At the peak stress level, the patient is injected with about 20-30 mCi of Tc-99m-sestamibi, while under the camera, and a post-stress imaging of about 2 minutes is taken, immediately. The total imaging time of this protocol is about 17 minutes, and the total patient time is about 45 minutes. The energy window is about 3-15%. The advantage of this protocol is that it is fast, and low dose.

18. A low-dose, single-isotope, fast imaging protocol: For imaging at rest, the patient is injected with about 0.3 mCi of Tc-99m-sestamibi, while under the camera. Immediately, a rest imaging of about 15 minutes is taken. The patient is then subject to a pharmacological stress, for example, by the administration of adenosine. At the peak stress level, the patient is injected with about 3 mCi of Tc-99m-sestamibi, while under the camera, and a post-stress imaging of about 15 minutes is taken, immediately. The total imaging time of this protocol is about 30 minutes, and the total patient time is about 45 minutes. The energy window is about 3-15%. The advantage of this protocol is that it is fast, and low dose.

Protocols for Low-Dose General Imaging

19. Brain perfusion mapping protocol: used for mapping of perfusion described by quantitative parameters (mg/min/gr); measurement of cerebral flow reserve in rest and stress protocols using pharmacological stress agents; parametric quantitation; and identification of disease signature, for example in Alzheimer's, depression, schizophrenia, and similar conditions. A patient is injected with up to about 3 mCi Tc-99m-exametazine (HMPAO), up to about 3 mCi Tc-99m N,N'(1,2-ethlenediyl)bis-L-cysteine diethyl ester (Tc-99m-ECD), and up to about 5 mCi of I-123 iofetamine hydrochloride. After a waiting period of up to one hour, imaging is taken, with an energy window of between 3 and 15%. The advantage of this protocol is that it can show stroke at an early stage and the extent of the event in an accurate way.

20. Hepatobiliary imaging: for studying the structure of the liver, including identification of hemangiomas, abcesses, and liver enlargement. A patient is injected with up to about 0.5 mCi Tc-99m-mebrofenin while under the camera, and imaging is begun immediately. The acquisition time is up to about 30 minutes, with an energy window of between 3 and 15%. This protocol studies fluid flow, rate of tracer uptake (passive or active), accumulation and redistribution of tracer, tracer metabolism, and secretion and/or washout of tracer or metabolite (passive or active).

21. Lung V/P-DTPA aerosol and macro-aggregated albumin (lung perfusion agent) protocol, for studying lung perfusion by quantitative parameters, such as ml/min/gr. A patient is injected with Tc-99m-diethylene triamine pentaacetate (DTPA), up to about 3 mCi (up to 1M particles) Tc-99m-macro-aggregated albumin (MAA), or up to 0.5 mCi DTPA In-111 while positioned under the camera. Substantially immediately after injection, an imaging of up to about 6 minutes is taken, with an energy window of between 3 and 15%. The advantage of this protocol is that it is fast.

Protocols for Imaging of Dynamic Processes

22. Cardiac perfusion (thallium rest) protocol: this protocol is used for imaging of cardiac perfusion under rest conditions. The perfusion is described by quantitative parameters (ml/min/gr), coronary flow reserve and parametric quantitation. A patient is injected with up to about 4 mCi Tl-201 thallous chloride, with the camera running, and imaging is begun immediately. Imaging is taken for a time of from about 2 to about 20 minutes, with an energy window of between 3 and 15%. This protocol enables the study of fluid flow, rate of tracer uptake (passive or active), tracer accumulation and redistribution, tracer metabolism, and secretion and/or washout (active or passive) of tracer/metabolites.

23. Cardiac perfusion (thallium stress) protocol: this protocol is used for imaging of cardiac perfusion under stress conditions. The perfusion is described by quantitative parameters (ml/min/gr), coronary flow reserve and parametric quantitation. A patient subjected to a pharmacological stress, for example, for example, by the administration of adenosine or to a physical stress, for example by exercising on a treadmill. At the peak stress level, the patient is injected with up to about 4 mCi Tl-201 thallous chloride, with the camera running, and imaging is begun immediately. Imaging is taken for a time of from about 2 to about 20 minutes, with an energy window of between 3 and 15%. This protocol enables the study of fluid flow, rate of tracer uptake (passive or active), tracer accumulation and redistribution, tracer metabolism, and secretion and/or washout (active or passive) of tracer/metabolites.

24. Cardiac perfusion (teboroxime rest) protocol: this protocol is used for imaging of cardiac perfusion under rest conditions. The perfusion is described by quantitative parameters (ml/min/gr), coronary flow reserve and parametric quantitation. A patient is injected with up to about 30 mCi teboroxime, with the camera running, and imaging is begun immediately. Imaging is taken for a time of up to 15 minutes, with an energy window of between 3 and 15%. This protocol enables the study of fluid flow, rate of tracer uptake (passive or active), tracer accumulation and redistribution, tracer metabolism, and secretion and/or washout (active or passive) of tracer/metabolites.

25. Cardiac perfusion (teboroxime stress) protocol: this protocol is used for imaging of cardiac perfusion under stress conditions. The perfusion is described by quantitative parameters (ml/min/gr), coronary flow reserve and parametric quantitation. A patient subjected to a pharmacological stress, for example, for example, by the administration of adenosine or to a physical stress, for example by exercising on a treadmill. At the peak stress level, the patient is injected with up to about 4 mCi teboroxime, with the camera running, and imaging is begun immediately. Imaging is taken for a time of up to 15 minutes, with an energy window of between 3 and 15%. This protocol enables the study of fluid flow, rate of tracer uptake (passive or active), tracer accumulation and redistribution, tracer metabolism, and secretion and/or washout (active or passive) of tracer/metabolites.

26. Cardiac perfusion (sestamibi rest) protocol: this protocol is used for imaging of cardiac perfusion under rest conditions. The perfusion is described by quantitative parameters (ml/min/gr), coronary flow reserve and parametric quantitation. A patient is injected with up to about 30 mCi Tc-99m-sestamibi, with the camera running, and imaging is begun immediately. Imaging is taken for a time of up to 15 minutes, with an energy window of between 3 and 15%. This protocol enables the study of fluid flow, rate of tracer uptake (passive or active), tracer accumulation and redistribution, tracer metabolism, and secretion and/or washout (active or passive) of tracer/metabolites.

27. Cardiac perfusion (sestamibi stress) protocol: this protocol is used for imaging of cardiac perfusion under stress conditions. The perfusion is described by quantitative parameters (ml/min/gr), coronary flow reserve and parametric quantitation. A patient subjected to a pharmacological stress, for example, for example, by the administration of adenosine or to a physical stress, for example by exercising on a treadmill. At the peak stress level, the patient is injected with up to about 30 mCi Tc-99m-sestamibi, with the camera running, and imaging is begun immediately. Imaging is taken for a time of up to 15 minutes, with an energy window of between 3 and 15%. This protocol enables the study of fluid flow, rate of tracer uptake (passive or active), tracer accumulation and redistribution, tracer metabolism, and secretion and/or washout (active or passive) of tracer/metabolites.

28. Cardiac perfusion (tetrofosmin rest) protocol: this protocol is used for imaging of cardiac perfusion under rest conditions. The perfusion is described by quantitative parameters (ml/min/gr), coronary flow reserve and parametric quantitation. A patient is injected with up to about 30 mCi tetrofosmin, with the camera running, and imaging is begun immediately. Imaging is taken for a time of up to 15 minutes, with an energy window of between 3 and 15%. This protocol enables the study of fluid flow, rate of tracer uptake (passive or active), tracer accumulation and redistribution, tracer metabolism, and secretion and/or washout (active or passive) of tracer/metabolites.

29. Cardiac perfusion (tetrofosmin stress) protocol: this protocol is used for imaging of cardiac perfusion under stress conditions. The perfusion is described by quantitative parameters (ml/min/gr), coronary flow reserve and parametric quantitation. A patient subjected to a pharmacological stress, for example, for example, by the administration of adenosine or to a physical stress, for example by exercising on a treadmill. At the peak stress level, the patient is injected with up to about 30 mCi tetrofosmin, with the camera running, and imaging is begun immediately. Imaging is taken for a time of up to 15 minutes, with an energy window of between 3 and 15%. This protocol enables the study of fluid flow, rate of tracer uptake (passive or active), tracer accumulation and redistribution, tracer metabolism, and secretion and/or washout (active or passive) of tracer/metabolites.

30. Cardiac perfusion (Q12 rest) protocol: this protocol is used for imaging of cardiac perfusion under rest conditions. The perfusion is described by quantitative parameters (ml/min/gr), coronary flow reserve and parametric quantitation. A patient is injected with up to about 30 mCi Tc-99m-sestamibi, with the camera running, and imaging is begun immediately. Imaging is taken for a time of up to 15 minutes, with an energy window of between 3 and 15%. This protocol enables the study of fluid flow, rate of tracer uptake (passive or active), tracer accumulation and redistribution, tracer metabolism, and secretion and/or washout (active or passive) of tracer/metabolites.

31. Cardiac perfusion (Q12 stress) protocol: this protocol is used for imaging of cardiac perfusion under stress conditions. The perfusion is described by quantitative parameters (ml/min/gr), coronary flow reserve and parametric quantitation. A patient subjected to a pharmacological stress, for example, for example, by the administration of adenosine or to a physical stress, for example by exercising on a treadmill. At the peak stress level, the patient is injected with up to about 30 mCi Tc-99m-sestamibi, with the camera running, and imaging is begun immediately. Imaging is taken for a time of up to 15 minutes, with an energy window of between 3 and 15%. This protocol enables the study of fluid flow, rate of tracer uptake (passive or active), tracer accumulation and redistribution, tracer metabolism, and secretion and/or washout (active or passive) of tracer/metabolites.

32. BMIPP (rest) protocol: this protocol is used for imaging of cardiac perfusion under rest conditions. The perfusion is described by quantitative parameters (ml/min/gr), coronary flow reserve and parametric quantitation. A patient is injected with up to about 30 mCi Tc-99m-sestamibi, with the camera running, and imaging is begun immediately. Imaging is taken for a time of up to 5 minutes, with an energy window of between 3 and 15%. This protocol enables the study of fluid flow, rate of tracer uptake (passive or active), tracer accumulation and redistribution, tracer metabolism, and secretion and/or washout (active or passive) of tracer/metabolites.

33. BMIPP (stress) protocol: this protocol is used for imaging of cardiac perfusion under stress conditions. The perfusion is described by quantitative parameters (ml/min/gr), coronary flow reserve and parametric quantitation. A patient subjected to a pharmacological stress, for example, for example, by the administration of adenosine or to a physical stress, for example by exercising on a treadmill. At the peak stress level, the patient is injected with up to about 30 mCi Tc-99m-sestamibi, with the camera running, and imaging is begun immediately. Imaging is taken for a time of up to 5 minutes, with an energy window of between 3 and 15%. This protocol enables the study of fluid flow, rate of tracer uptake (passive or active), tracer accumulation and redistribution, tracer metabolism, and secretion and/or washout (active or passive) of tracer/metabolites.

34. A protocol utilizing any of the above combinations: this protocol is used for imaging of cardiac perfusion under either stress or rest conditions. The perfusion is described by quantitative parameters (ml/min/gr), coronary flow reserve and parametric quantitation. A patient is injected with any of the above radiopharmaceuticals, with the camera running, and imaging is begun immediately. Imaging is taken for a time of up to 10 minutes, with an energy window of between 3 and 15%. This protocol enables the study of fluid flow, rate of tracer uptake (passive or active), tracer accumulation and redistribution, tracer metabolism, and secretion and/or washout (active or passive) of tracer/metabolites.

35. A protocol utilizing all PET radiopharmaceuticals within the currently used PET protocols used with our SPECT camera: this protocol is used for imaging of cardiac perfusion under stress or rest conditions. The perfusion is described by quantitative parameters (ml/min/gr), coronary flow reserve and parametric quantitation. A patient is injected with any PET radiopharmaceutical, as discussed above, with the camera running, and imaging is begun immediately. Imaging is taken for a time of up to 15 minutes, with an energy window of between 3 and 15%. This protocol enables the study of fluid flow, rate of tracer uptake (passive or active), tracer accumulation and redistribution, tracer metabolism, and secretion and/or washout (active or passive) of tracer/metabolites.

36. Cancer—tumor perfusion protocol—evaluation of tumors by single isotope SPECT with Teboroxime Tc-99m or Tc-99m-sestamibi, or Tl-201, or Tc-99m tetrofosmin: this protocol is used for imaging of cardiac perfusion under rest or stress conditions. Image tumor blood supply with Tl-201 thallous chloride in combination with Tc-99m-sestamibi Teboroxime or Tc-99m tetrofosmin uptake and washout which is affected by the MDR complex showing therapeutic response to chemo. The perfusion is described by quantitative parameters (ml/min/gr) and parametric quantitation. A patient is injected with up to about 30 mCi Tc-99m-sestamibi, with the camera running, and imaging is begun immediately. Imaging is taken for a time of up to 5 minutes, with an energy window of between 3 and 15%. This protocol enables the study of fluid flow, rate of tracer uptake (passive or active), tracer accumulation and redistribution, tracer metabolism, and secretion and/or washout (active or passive) of tracer/metabolites.

37. Cancer—tumor perfusion protocol—evaluation of tumors by simultaneous dual isotope SPECT with Tl-201 thallous chloride and Tc-99m-sestamibi: this protocol is used for imaging of cardiac perfusion under rest or stress conditions. Tumor imaging; Image tumor blood supply with Tl-201 thallous chloride in combination with Tc-99m-sestamibi washout which is affected by the MDR complex showing therapeutic response to chemo. The perfusion is described by quantitative parameters (ml/min/gr) and parametric quantitation. About 4 mCi Tl-201 thallous chloride and up to 30 mCi Tc-99m-sestamibi is injected with the camera running, and imaging is begun immediately. Imaging is taken for a time of up to 15 minutes, with an energy window of between 3 and 15%. This protocol enables the study of fluid flow, rate of tracer uptake (passive or active), tracer accumulation and redistribution, tracer metabolism, and secretion and/or washout (active or passive) of tracer/metabolites.

38. Kidney—renal function (111-In-DTPA and Tc99m-MAG3) protocol: this protocol is used for assessment of filtration and tubular secretion, perfusion and secretion described by quantitative parameters (ml/min/gr), and parametric quantitation. A patient is injected with up to about 1 mCi of 111-In-DTPA and 10 mCi of Tc-MAG3, with the camera running, and imaging is begun immediately. Imaging is taken for a time of up to 10 minutes, with an energy window of between 3 and 15%. This protocol enables the study of fluid flow, rate of tracer uptake (passive or active), tracer accumulation and redistribution, tracer metabolism, and secretion and/or washout (active or passive) of tracer/metabolites.

39. Kidney—renal function (111-In-DTPA and Hippuran I-123) protocol: this protocol is used for assessment of filtration and tubular secretion, under rest or stress conditions. The perfusion is described by quantitative parameters (ml/min/gr) and parametric quantitation. The patient is injected with up to 1 mCi of 111-In-DTPA and up to 1 mCi of Hippuran I-123, with the camera running, and imaging is begun immediately. Imaging is taken for a time of up to 15 minutes, with an energy window of between 3 and 15%. This protocol enables the study of fluid flow, rate of tracer uptake (passive or active), tracer accumulation and redistribution, tracer metabolism, and secretion and/or washout (active or passive) of tracer/metabolites.

40. Brain perfusion protocol: this protocol is used for perfusion mapping under rest or stress conditions. The perfusion is described by quantitative parameters (ml/min/gr), cerebral flow reserve (in stress protocols using pharmacological stress agents), parametric quantitation, and disease signature (Alzheimer's, depression, schizophrenia, etc.). A patient is injected with up to about 20 mCi HMPAO, 99m labeled Tc-99m ECD (neurolite), and up to 5 mCi spectamine I-123, with the camera running, and imaging is begun immediately. Imaging is taken for a time of up to 30 minutes, with an energy window of between 3 and 15%. This protocol enables the study of fluid flow, rate of tracer uptake (passive or active), tracer accumulation and redistribution, tracer metabolism, and secretion and/or washout (active or passive) of tracer/metabolites.

41. Brain perfusion protocol: this protocol is used for perfusion mapping under rest or stress conditions. The perfusion is described by quantitative parameters (ml/min/gr), cerebral flow reserve (in stress protocols using pharmacological stress agents), parametric quantitation, and disease signature (Alzheimer's, depression, schizophrenia, etc.). The patient is injected with up to about 20 mCi teboroxime, with the camera running, and imaging is begun immediately. Imaging is taken for a time of up to 30 minutes, with an energy window of between 3 and 15%. This protocol enables the study of fluid flow, rate of tracer uptake (passive or active), tracer accumulation and redistribution, tracer metabolism, and secretion and/or washout (active or passive) of tracer/metabolites.

42. Hepatobiliary Tc-99m sulfur colloid protocol: this protocol is used for looking at the liver structure (hemangiomas, abcesses, liver enlargement, etc.) under rest or stress conditions. A patient is injected with up to about 5 mCi Tc-99m sulfur colloid, with the camera running, and imaging is begun immediately. Imaging is taken for a time of up to 10 minutes, with an energy window of between 3 and 15%. This protocol enables the study of fluid flow, rate of tracer uptake (passive or active), tracer accumulation and redistribution, tracer metabolism, and secretion and/or washout (active or passive) of tracer/metabolites.

43. Liver function study protocol: this protocol is used for imaging under rest or stress conditions. The patient is injected with up to about 10 mCi Tc-99m disida (disulfenine), choletec, HIDA, (all bind to bilirubin sites), with the camera running, and imaging is begun immediately. Imaging is taken every 5 minutes, for a time of 5 minutes, for up to an hour, with an energy window of between 3 and 15%. If no activity is seen in the intestine, a pharmacological agent is used for gall bladder contraction. This protocol enables the study of fluid flow, rate of tracer uptake (passive or active), tracer accumulation and redistribution, tracer metabolism, and secretion and/or washout (active or passive) of tracer/metabolites.

44. Dual phase gastric emptying study protocol: this protocol is used for determining the rate that the stomach empties of food. With the camera running, imaging is begun immediately before the patient injests solid food that is labeled with Tc99m-S-colloid or liquid food that is labeled with In-111-DTPA labeled. The study continues until the stomach is approximately empty of all tracer.

45. Cardiac vulnerable plaque study protocol: this protocol is used for finding plaques that may be released into the blood stream and as a result initiate a CVA or cardiac infarct. A patient is injected with up to 5 mCi of Annexin radiopharmaceutical labeled with 111-In imaging isotope and up to 5 mCi of AccuTec radiopharmaceutical labeled with Tc-99m-sestamibi and waits for 24 hours and imaging begins. AccuTec attaches to activated platelets and shows thrombus. Annexin attaches to apoptotic cells; apoptotic cells being human neutrophils that have died and broken up, demonstrating inflammatory infiltrate. This protocol enables the study of dynamic plaques that are associated with cardiac plaque tissue damage and repair.

46. Prostate imaging study protocol: this protocol is used for determining the presence and/or extent of metastatic and/or primary cancer in the prostate. A patient is injected with up to 5 mCi of Prostascint radiopharmaceutical, containing 111-In-DTPA imaging isotope and waits for 24-72 hours and imaging begins. This protocol enables the study of dynamic plaques that are associated with tissue damage and repair.

47. SST-receptor imaging study protocol: this protocol is used for determining the presence and/or extent of SST-receptor expressing tumors, whether metastatic and/or primary cancerous tumors. A patient is injected with up to 5 mCi of Octreotide radiopharmaceutical, containing 111-In-DTPA imaging isotope and waits for 24-72 hours and imaging begins. This protocol enables the study of SST-receptor expressing tumors metastatic and/or primary cancerous tumors.

48. Neuroendocrine tumors imaging study protocol: this protocol is used for determining the presence and/or extent of metastatic and/or primary Neuroendocrine tumors by binding to associated Somatostatin receptors. A patient is injected with up to 20 mCi of Neotec radiopharmaceutical, containing Tc-99m-sestamibi imaging isotope and waits for up to one hour and imaging begins. This protocol enables the study of Neuroendocrine tumors.

49. Thrombus detection imaging study protocol: this protocol is used for imaging DVT and intratererial thrombus in coronary and carotid arteries, by binding to GP IIb/IIIa receptors on platelets. A patient is injected with up to 20 mCi of Acutect radiopharmaceutical, containing Tc-99m-sestamibi imaging isotope and waits for 0-20 minutes and imaging begins. This protocol enables the study of Thrombus detection, including DVT and intratererial thrombus in coronary and carotid arteries.

50. Pheochromocytoma and or Myocardial failure imaging study protocol: this protocol is used for imaging pancreatic adrenergic tissue uptake and presynaptic adrenergic receptors, adrenergic being associated with adrenaline, by binding to GP IIb/IIIa receptors on platelets. A patient is injected with up to 5 mCi of MIBG Radiopharmaceutical, containing I-123 iofetamine hydrochloride imaging isotope and waits for 24 hours and imaging begins. This protocol enables the study of tissue and receptors that are associated with adrenergic uptake.

51. A gated cardiac stress imaging protocol: a dynamic study to investigate the effects of stress, for example adenosine, ice-water, and/or vasodilatation agents, on blood flow kinetics. A patient is injected with about 4 mCi of Th-201-thallous chloride, some time prior to the imaging. After a waiting period of 0-2 minutes, a rest imaging of about 2-5 minutes is taken. The patient is then administered adenosine, and/or vasodilatation agents or hand is emerged into ice-water. After a waiting period of about 0-5 minutes an imaging of about 2-10 minutes is taken.

52. A Kidney function imaging protocol: a dynamic study to investigate the effects of stress on blood flow kinetics (captopril; fusides etc) of the kidneys. A patient is injected with about 2-4 mCi Indium and/or Tc-MAG3, while remaining substantially at rest. A rest imaging of about 10-30 minutes is taken. After a waiting period of about 10-30 minutes, imaging of about 2 minutes is taken.

53. A Bexaar dosimetry imaging protocol: a study to determine the dose required to inject in order to administer an effective dose of 75 REM. A patient is injected with about 5 mCi/35 mg protein of, I-123 iofetamine hydrochloride, some time prior to each scan; each scan having an energy window anywhere between 3-15% and lasting approximately five minutes. Three acquisitions are acquired during the week to produce a graph of metabolism.

Protocols for Multiple Radiopharmaceuticals

A combination of at least two radiopharmaceuticals may be used for specific imaging protocols. Such a combination may be used, for example, to obtain information regarding both a pathology and an anatomy, such that the location of an imaged pathology within the body is identified; or to identify multiple pathologies in different sections of the body of a subject; or to study different pathological processes within a single organ of a subject.

The individual radiopharmaceuticals may be administered sequentially or substantially simultaneously. Preferably, the radiopharmaceuticals are administered as a single composition.

Combinations for the Study of a Pathology and an Anatomy:

1. Thallium-201-thallous chloride (a parathyroid avid agent) and Tc-99m-pertechnetate (a thyroid agent) may be administered in combination for parathyroid adenoma imaging, and anatomical differentiation of the parathyroid from the thyroid. A patient is injected up to about 1 mCi Thallium-201-thallous chloride, and up to about 15 mCi a dose of Te-99m. After a waiting time of about 10 minutes, imaging is taken for a period of about 5 minutes, with an energy window of between 2 and 10 percent.

2. Tc-99m-methoxyisobutylisonitrile (sestamibi) (a parathyroid avid agent) and I-123 (a thyroid agent) may be administered in combination for parathyroid adenoma imaging, and anatomical differentiation of the parathyroid from the thyroid. A patient is injected with up to about 15 mCi Tc-99m-sestamibi and up to about 100 μCi I-123. After a waiting time of about 10 minutes, imaging is taken for a period of about 5 minutes, with an energy window of between 2 and 10 percent.

3. I-123 and Tc-99m-labeled red blood cells or Tc-99m-dihydrogen methylenediphosphate (medronate MDP) may be administered in combination for imaging of thyroid cancer and identification of the location of the thyroid cancer. Tc99m-MDP is a bone-imaging agent, which enables visualization of the skeleton to provide anatomical landmarks. Tc99m-labeling of red blood cells enables the larger blood vessels to be visualized to provide anatomical landmarks.

A patient is injected with up to about 4 mCi thallium-201-thallous chloride, and up to about 10 mCi of MDP. After a waiting time of up to about 2 hours, imaging is taken for a period of up to about 30 minutes, with an energy window of between 2 and 10 percent.

4. In-111-L-Cysteinamide, D-phenylalanyl-L-cysteinyl-L-phenylalanyl-D-tryptophyl-L-lysyl-L-threonyl-N-[2-hydroxy-1-(hydroxy-methyl)propyl]-, cyclic 7)-disulfide (In-111-octreotide) and Tc-99m-MDP may be administered in combination to optimally localize certain endocrine tumors. In-111-Octreotide is a tumor imaging agent for somastatin-receptor expressing tumors. Tc99m-MDP is a bone-imaging agent, which enables visualization of the skeleton to provide anatomical landmarks.

A patient is injected with up to about 4 mCi In-111-octreotide, and up to about 15 mCi of Tc-99m-MDP. Within 3 days of injection of In-111-octreotide, but not more than 2 hours after injection of Tc-99m-MDP, imaging is taken for a period of up to about 30 minutes, with an energy window of between 2 and 10 percent. Hence, for example, the two radiopharmaceuticals may be administered substantially simultaneously, and imaging taken within 2 hours of injection. Alternatively, In-111-octreotide may be injected first, and imaging taken within 3 days of this injection, with Tc-99m-MDP injected at a later time point, no more than 2 hours prior to imaging.

5. In-111-capromab pentetide and Tc-99m-labeled red blood cells (RBCs) may be administered for delineating vascular structures of the pelvis or abdomen, and enabling the clinician to distinguish the blood vessels from the lymph nodes by pathologic uptake of antibodies. In-111-capromab pendetide is a monoclonal anti-tumor antibody to prostate specific membrane antigen (PMSA).

A patient is injected with up to about 3 mCi In-111-capromab pentetide, and up to about 15 mCi of Tc-99m-RBCs. Within 3 days of injection of In-111-capromab pentetide, but not more than 2 hours after injection of Tc-99m-RBCs, imaging is taken for a period of up to about 30 minutes, with an energy window of between 2 and 10 percent.

6. Tc-99m-colloid and In-111-white blood cells (WBCs) may be administered in combination for the identification and localization of bone infection. A patient is injected with up to about 15 mCi Tc-99m-colloid, and up to about 3 mCi of In-111-WBCs. Within 3 days of injection of In-111-WBC, but not more than 2 hours after injection of Tc Tc-99m-colloid, imaging is taken for a period of up to about 30 minutes, with an energy window of between 2 and 10 percent.

7. Tl-201-thallous chloride (a tumor imaging agent) and Tc-99m-MDP (a bone scan agent) may be administered in combination to evaluate the invasion of bone or cartilage by head or neck cancer. A patient is injected with up to about 2 mCi thallium-201-thallous chloride, and up to about 15 mCi of MDP. After a waiting time of up to about 2 hours, imaging is taken for a period of up to about 30 minutes, with an energy window of between 2 and 10 percent.

Combinations for the Study of Multiple Pathologies:

8. Tl-201-thallous chloride, Te-99m-sestamibi, and In-111-white blood cells may be administered in combination for the assessment of various pathological conditions, including cardiac conditions, tumors, and infection. A patient is injected with up to about 2 mCi In-111-WBCs and after 24 hours injected with up to about 1 mCi Tl-201-thallous chloride, up to about 10 mCi of Te-99m-sestamibi. After a waiting time of up to about 3 min following last injection, imaging is taken for a period of up to about 30 minutes, with an energy window of between 2 and 10 percent.

9. Tl-201-thallous chloride, Te-99m-MDP, and In-111-white blood cells may be administered in combination for the assessment of various pathological conditions, including cardiac conditions, tumors, and infection. A patient is injected with up to about 2 mCi In-111-WBCs and after 24 hours injected with up to about 1 mCi Tl-201-thallous chloride, up to about 10 mCi of Te-99m-sestamibi. After a waiting time of up to about 3 min following last injection, imaging is taken for a period of up to about 30 minutes, with an energy window of between 2 and 10 percent.

Combinations for the Study of Different Pathological Processes of the Same Organ:

10. Tl-201-thallous chloride. Tc-99m-teboroxime or Tc-99m-sestamibi, and I-123-beta-methyl-p-iodophenylpentadecanoic acid (BMIPP) may be administered in combination for the study of acute myocardial ischemia. A patient is injected with up to about 2 mCi I-123-beta-methyl-p-iodophenylpentadecanoic acid (BMIPP) and after 48 hours injected with up to about 1 mCi Tl-201-thallous chloride, up to about 10 mCi Tc-99m-teboroxime or Tc-99m-sestamibi. Almost immediately following last injection imaging is taken for a period of up to about 30 minutes, with an energy window of between 2 and 10 percent.

11. Tc-99m-Fanoselomab and In-111-white blood cells may be administered in combination to study fever of unknown origin. A patient is injected with up to about 2 mCi In-111-white blood cells and after 24 hours injected with up to 15 mCi 99m-Fanoselomab. Almost immediately following last injection, imaging is taken for a period of up to about 30 minutes, with an energy window of between 2 and 10 percent.

12. I-123-iodobenzamide (IBZM) and Tc-99m-Exametazine (HMPAO) may be administered in combination to study schizophrenia or Parkinson's disease. A patient is injected with up to 2 mCi I-123-iodobenzamide (IBZM) and after 24 hours injected with up to about 15 mCi Tc-99m-Exametazine (HMPAO). Almost immediately following last injection, imaging is taken for a period of up to about 30 minutes, with an energy window of between 2 and 10 percent.

13. In-111-labeled antibody, Tc-99m-sestamibi or Tc-99m-Arcitumomab and Tl-201-thallous chloride may be administered in combination for tumor identification and characterization by perfusion studies. A patient is injected with up to about 1 mCi I-111-labeled antibody, and after 24 hours the patient is injected with up to about 10 mCi Tc-99m-sestamibi or Tc-99m-Arcitumomab, and up to about 1 mCi Tl-201-thallous chloride. After a waiting time of up to 5 min from last injection, imaging is taken for a period of up to about 30 minutes, with an energy window of between 2 and 10 percent.

14. In-111-diethylene triamine pentaacetate (DTPA) and Tc-99m-mercaptoacetyltriglycine (MAG3) may be administered in combination for dynamic flow studies for the investigation of renal function. A patient is injected with up to about 2 mCi In-111-diethylene triamine pentaacetate (DTPA) and after 24 hours is injected with up to about 15 mCi Tc-99m-mercaptoacetyltriglycine (MAG3). After a waiting time of up to 5 min from last injection, imaging is taken for a period of up to about 30 minutes, with an energy window of between 2 and 10 percent.

15. Tl-201-thallous chloride and Tc-99m-teboroxime or Tc-99m-sestamibi may be administered in combination for the study of tumor perfusion and therapeutic response. A patient is injected with up to about 1 mCi Tl-201-thallous chloride and up to about 15 mCi Tc-99m-teboroxime or Tc-99m-sestamibi. After a waiting time of up to about 1 hour, imaging is taken for a period of up to about 30 minutes, with an energy window of between 2 and 10 percent.

16. Tc-99m-sulfur colloid and In-111-WBCs may be administered in combination to differentiate between infection and bone marrow activation. A patient is injected with up to about 2 mCi In-111-WBCs. After a waiting time of up to about 24 hours the patient is injected with about 15 mCi Tc-99m-sulfur colloid and almost immediately injected after last injection, imaging is taken for a period of up to about 30 minutes, with an energy window of between 2 and 10 percent.

17. Tc-99m-MDP and In-111-WBCs may be administered in combination to differentiate between acute and chronic acute osteomyelitis. A patient is injected with up to about 2 mCi In-111-WBCs and after a waiting time of up to about 24 hours the patient is injected with up to about 15 mCi Tc-99m-MDP. The patient is imaged almost immediately following the second injection and imaging is taken for a period of up to about 30 minutes, with an energy window of between 2 and 10 percent.

18. Gallium-67 and In-111-WBCs may be administered in combination to differentiate between acute and chronic inflammation. A patient is injected with up to about 5 mCi gallium-67 and up to about 2 mCi In-111-WBCs. After a waiting time of up to about 72 hours, imaging is taken for a period of up to about 30 minutes, with an energy window of between 2 and 10 percent.

19. Tc-99m-teboroxime or Tl-201-thallous chloride and In-111-annexin may be administered in combination to study myocardial perfusion and apoptosis. A patient is injected with up to about 2 mCi In-111-annexin and after about 24 hours the patient is injected with up to about 15 mCi Tc-99m-teboroxime or up to about 2 mCi Tl-201-thallous chloride. Almost immediately after second injection, imaging is taken for a period of up to about 30 minutes, with an energy window of between 2 and 10 percent.

20. Tl-201-thallous chloride and Tc-99m-pyrophosphate may be administered in combination to investigate myocardial perfusion and infarct. A patient is injected with up to about 2 mCi Tl-201-thallous chloride and up to about 15 mCi Tc-99m-pyrophosphate. After a waiting time of up to about 1 hour, imaging is taken for a period of up to about 30 minutes, with an energy window of between 2 and 10 percent.

21. Cardiac vulnerable plaque and myocardial perfusion study protocol: this protocol is used for finding plaques that may be released into the blood stream and as a result initiate a CVA or cardiac infarct and determining the perfusion defect if any that it causes. A patient is injected with up to 5 mCi of Annexin radiopharmaceutical labeled with 111-In imaging isotope and after 24 hours the patient is injected with up to 5 mCi of AccuTec radiopharmaceutical labeled with Tc-99m-sestamibi and up to 1 mCi Tl201. Immediately following the second injection imaging is carried out for up to 30 min. AccuTec attaches to activated platelets and shows thrombus. Annexin attaches to apoptotic cells; apoptotic cells being human neutrophils that have died and broken up, demonstrating inflammatory infiltrate. This protocol enables the study of dynamic plaques that are associated with cardiac plaque tissue damage and repair.

Protocols for Non-Coincidence Imaging Using PET Radiopharmaceuticals

The following imaging protocols use non-coincidence imaging using PET radiopharmaceuticals, as is further described in the Tables shown in FIGS. 30-38:

1. Use of F-18-Fluorodeoxyglucose (FDG), as a substrate for hexokinase in glucose metabolism, for the study of glucose metabolism of cells including tumor, heart and brain cells.

2. Use of F-18-Fluoromisonidazole for imaging of hypoxia and oxidative metabolism, with the clinical application of radiotherapy treatment planning.

3. Use of F-18-3'-Fluoro-3'-deoxythymidine (FLT) for the study of DNA synthesis.

4. Use of F-18-Fluoromethyl choline (FCH) as a choline precursor for cell membrane synthesis, for the study of choline metabolism of tumors.

5. Use of F-18-4-Fluoro-m-tyrosine (FMT) as a precursor for dopamine synthesis and as a substrate for aromatic amino acid decarboxylase (AAAD), with the clinical application of imaging brain tumors.

6. Use of F-18-6-Fluoro-L-DOPA as a precursor for dopamine synthesis and as a precursor for AAAD, with the clinical applications of imaging and grading Parkinson's disease and imaging neuroendocrine tumors.

7. Use of F-18-FP-β-CIT for binding to the dopamine transporter in dopaminergic axons, with the clinical application of imaging and grading Parkinson's disease and imaging neuroendocrine tumors.

8. Use of F-18-Pencyclovir (FHBG) to target thymidine kinase, with the clinical application of imaging reporter gene expression.

9. Use of F-18-Fluoroestradiol (FES) to target estrogen receptors, with the clinical application of breast tumor imaging.

10. Use of C-11-Methionine to target amino acid synthesis, with the clinical application of imaging brain tumors.

11. Use of Tc-99m-P280, Acutect® to target GP IIb/IIIa receptors on platelets, with the clinical applications of detection of thrombosis, such as deep vein thrombosis (DVT) and intratererial thrombosis in coronary and carotid arteries.

17. Use of C-11-Raclopride to target dopamine D2 receptors, for brain imaging of dopamine D2 receptors in schizophrenia, and assessment of dose for neuroleptics.

18. Use of I-123-iodobenzamide (IBZM) to target dopamine D2 receptors, for brain imaging of dopamine D2 receptors in schizophrenia, and assessment of dose for neuroleptics.

19. C-11-carfentanil to target Mu opioid receptors in brain, with the clinical application of imaging drug addiction.

20. Use of C-11-α-methyl-L-tryptophan as a precursor for α-methyl serotonin synthesis and as a substrate for AAAD enzyme, with the clinical application of imaging depression.

21. Use of C-115-Hydroxytryptophan as a precursor for serotonin synthesis with the clinical application of imaging neuroendocrine tumors.

22. Use of F-18-MPPF to bind to 5-HT1A (5-hydroxytryptamine-1A) serotonin receptors, with the clinical application of imaging depression and epilepsy.

23. Use of F-18-Altanserin to bind to 5-HT2A serotonin receptors with the clinical application of imaging depression and epilepsy.

24. Use of C-11-Acetate for the study of tricarboxylic acid cycle activity and oxidative metabolism with the clinical application of studying myocardial oxygen metabolism.

25. Use of C-11-Palmitate as a precursor for fatty acid metabolism with the clinical application of imaging myocardial metabolism.

26. F-18-Fluorodopamine to target presynaptic adrenergic receptors

Protocols for Beta Emitting Radiopharmaceuticals

The following beta emitting radionuclides may be used for diagnostic studies, using a dose of about 1 mCi, using the camera of the present invention: Sm-153 ($T_{1/2}$ 1.95 days), I-131 ($T_{1/2}$ 8.04 days), Cu-67 ($T_{1/2}$ 2.58 days), Lu-177 ($T_{1/2}$ 6.7 days), and Sn-117m ($T_{1/2}$ 13.6 days). These include both long-lived radiopharmaceuticals and radiopharmaceuticals with low abundance gamma.

Protocols for Long-Lived Radiopharmaceuticals

Long-lived radiopharmaceuticals suitable for use with the camera of the present invention include I-131 and Sn-117m.

Protocols for Radiopharmaceuticals with Low Abundance Gamma

Cu-67, Lu-177 and Sm-153

It is expected that during the life of this patent many relevant radiopharmaceuticals, radiological imaging devices and two and three dimensional imaging systems will be developed and the scopes of the corresponding terms herein, are intended to include all such new technologies a priori.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed:

1. A non-transitory tangible medium comprising
at least one radiopharmaceutical identity;
SPECT measured values of at least one radiopharmaceutical kinetic parameter of a flow rate across a tissue membrane, for the radiopharmaceutical, and
a set of instructions for associating the at least one radiopharmaceutical kinetic parameter with a disease signature.

2. The non-transitory tangible medium of claim 1, wherein the disease signature is indicative of perfusion.

3. The non-transitory tangible medium of claim 1, the disease signature is indicative of blood flow quality.

4. The non-transitory tangible medium of claim 1, wherein the disease signature is indicative of a metabolic rate.

5. Apparatus for performing automatic diagnosis, based on SPECT data, comprising at least one computer usable non-transitory tangible medium having a computer readable program code embodied therein, said computer readable program code adapted to be executed to implement a set of instructions for:
providing pathological signatures, each characterized by a unique combination of at least two patient parameters, at least one of which relating to behavior of a radiopharmaceutical in vivo, as measured by SPECT;
measuring the at least two patient parameters, wherein the at least one patient parameter relating to the behavior of the radiopharmaceutical in vivo is measured by SPECT imaging; and
automatically diagnosing a pathology by automatically matching the at least two patient parameters and the pathological signatures.

6. The apparatus of claim 5, wherein automatically diagnosing a pathology comprises automatically diagnosing based on a database of values for normal and diseased populations.

7. The apparatus of claim 6, wherein automatically diagnosing includes determining a degree of a pathology.

8. The apparatus of claim 5, wherein measuring includes measuring at least one radiopharmaceutical kinetic parameter of a flow rate across a tissue membrane.

9. The apparatus of claim 5, wherein the set of instructions further comprises determining a preferred administration dose of a pharmaceutical agent for at least one future administration to the body according to the pathology.

10. The apparatus of claim 9, wherein the future administration is of a radiopharmaceutical agent.

11. The method of claim 9, wherein the future administration is of a therapeutic agent.

12. The apparatus of claim 9, wherein the future administration takes into account a member of a group consisting of: toxicity, radiation dose, clearance rate, uptake rate by an organ, and a measurement provided by a previous administration to weigh benefit and potential harm.

13. The apparatus of claim 5, wherein at least one of the pathological signatures is indicative of perfusion.

14. The apparatus of claim 5, wherein at least one of the pathological signatures is indicative of blood flow quality.

15. The apparatus of claim 5, wherein at least one of the pathological signatures is indicative of a metabolic rate.

16. A non-transitory tangible medium comprising a set of instructions for:
providing pathological signatures, each characterized by a unique combination of at least two patient parameters, at least one of which relating to behavior of a radiopharmaceutical in vivo, as measured by SPECT;
measuring the at least two patient parameters, wherein the at least one patient parameter relating to the behavior of the radiopharmaceutical in vivo is measured by SPECT imaging; and
automatically diagnosing a pathology by automatically matching the at least two patient parameters and the pathological signatures.

17. The non-transitory tangible medium of claim 16, wherein automatically diagnosing a pathology comprises automatically diagnosing based on a database of values for normal and diseased populations.

18. The non-transitory tangible medium of claim 16, wherein measuring includes measuring at least one radiopharmaceutical kinetic parameter of a flow rate across a tissue membrane.

19. The apparatus of claim 16, wherein the automatically diagnosing further comprises automatically determining the degree of the pathology.

20. The non-transitory tangible medium of claim 16, wherein the at least two patient parameters comprises a distribution of the radiopharmaceutical in the body.

21. The non-transitory tangible medium of claim 16, wherein at least one of the at least two patient parameters is relating to a combination of at least two radiopharmaceuticals.

22. The non-transitory tangible medium of claim 16, wherein at least one of the at least two patient parameters is relating to a combination of at least two radiopharmaceuticals.

* * * * *